(12) United States Patent
Heilshorn et al.

(10) Patent No.: US 9,399,068 B2
(45) Date of Patent: *Jul. 26, 2016

(54) HETERO-ASSEMBLING, TUNABLE, AND INJECTABLE HYDROGELS FOR CELL ENCAPSULATION

(71) Applicant: The Board of Trustees of the Leland Stanford Junior University, Palo Alto, CA (US)

(72) Inventors: Sarah C. Heilshorn, Mountain View, CA (US); Widya Mulyasasmita, Mountain View, CA (US); Lei Cai, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/690,589

(22) Filed: Apr. 20, 2015

(65) Prior Publication Data

US 2015/0290329 A1 Oct. 15, 2015

Related U.S. Application Data

(63) Continuation-in-part of application No. 12/455,996, filed on Jun. 9, 2009, now Pat. No. 9,011,914.

(60) Provisional application No. 61/060,144, filed on Jun. 10, 2008, provisional application No. 61/989,577, filed on May 7, 2014.

(51) Int. Cl.
*A61K 47/42* (2006.01)
*A61K 9/00* (2006.01)
*C12N 5/00* (2006.01)

(52) U.S. Cl.
CPC ............ *A61K 47/42* (2013.01); *A61K 9/0019* (2013.01); *A61K 9/0024* (2013.01); *C12N 5/0012* (2013.01); *C12N 2533/30* (2013.01); *C12N 2533/50* (2013.01)

(58) Field of Classification Search
None
See application file for complete search history.

(56) References Cited

U.S. PATENT DOCUMENTS

| | | | |
|---|---|---|---|
| 6,090,911 A * | 7/2000 | Petka | A61L 15/32 424/445 |
| 6,129,761 A | 10/2000 | Hubbell | |
| 7,229,634 B2 | 6/2007 | Tirrell | |
| 7,371,719 B2 | 5/2008 | Stupp | |
| 9,011,914 B2 * | 4/2015 | Wong Po Foo | A61K 9/0024 424/484 |
| 2004/0242469 A1 | 12/2004 | Lee | |
| 2007/0099840 A1 | 5/2007 | Ulijn | |
| 2008/0145934 A1 | 6/2008 | Harris | |

OTHER PUBLICATIONS

Petka et al., Science, 1998, 281, 389-392.*
Kanelis et al., Nature Structural Biology, 2001, 8, 407-412.*
Ramachandran et al., Biomacromolecules, 2005, 6, 1316-1321.*
Guler et al. (2006). Presentation of RGDS Epitopes on Self-Assembled Nanfibers of Branched Peptide Amphiphiles. Biomacromolecules 2006-7(6):1855-1863.
Schneider et al. (2002) Responsive Hydrogels from the Intramolecular Folding and Self-Assembly of a Designed Peptide. J. Am. Chem. Soc. 2002-124(50):15030-15037.
Petka et al. (1998). Reversible Hydrogels from Self-Assembling Artificial Proteins. Science (1998)-281:389-392.
Shen et al. (2007). Structure and mechanical properties of artificial protein hydrogels assembled through aggregation of leucine zipper peptide domains. Soft Matter 2007-3:99-107.
Kanelis et al. (2001). Solution structure of a Nedd4 WW domain-ENaC peptide complex. Nature Structural Biology 2001-8(5):407:412.
Russ et al. (2005). Natural-like function in artificial WW domains. Nature 2005-437:579:583.
Shen et al. (2006). Tuning the erosion rate of artificial protein hydrogels through control of network topology.nature materials vol. 5 Feb. 2006 www.nature.com/naturematerials. 153-158.

* cited by examiner

*Primary Examiner* — James H Alstrum Acevedo
*Assistant Examiner* — Roy Teller
(74) *Attorney, Agent, or Firm* — Lumen Patent Firm

(57) ABSTRACT

A viscoelastic hydrogel based on a protein hetero-assembled with a polymer is provided. The protein cannot self-assemble with itself and the polymer cannot self-assemble with itself. The protein has a first association sequence (1stA) and a first spacer (1stSp). The polymer has a second association sequence (2ndA) and a second spacer (2ndSp). The first association sequence and the second association sequence are physically cross-linked to interact with each other with a 1:1 known and specific stoichiometry to form a three dimensional scaffold. The protein is represented by $\{1stA(1stSp)\}_x 1stA$, where x is $\geq 2$, and the polymer is represented by $\{2ndA(2ndSp)\}_y 2ndA$, where $y \geq 2$.

11 Claims, 32 Drawing Sheets

Protein A
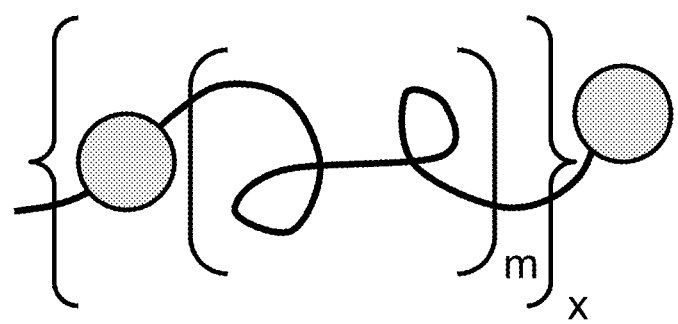
Protein B
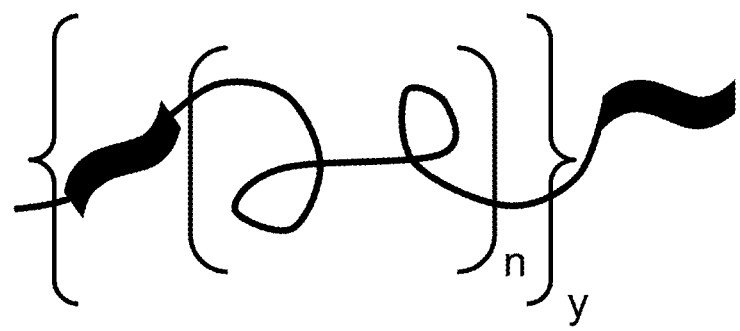
FIG. 1

| Domains | Schematic Representation | Amino Acid Sequences |
|---|---|---|
| WW Domain CC43 | | RLPAGWEQRMDVKGRPYYDVTKSTTWEDPRPE |
| WW Domain N39 | | PLPPGWEERTHTDGRVFFINHNIKKTQWEDPRMQ |
| Polyproline-rich Peptide PPxY | | EY▒Y▒▒▒Y▒SG |
| Hydrophilic Spacer 1 with Cell-Binding Site | | [AGAGAGPEG]$_2$[RGDSAGPEG][AGAGAGPEG]$_3$ OR [AGAGAGPEG]$_2$[YIGSRGPEG][AGAGAGPEG]$_3$ |
| Hydrophilic Spacer 2 | | [AGAGAGPEG]$_{n=2}$ |
| N-terminal 6xHis Tag | | |

| Hydrogel Components | | |
|---|---|---|
| C[x+2] | | ▒▒▒▒▒▒▒▒▒▒▒▒▒▒[RLPAGWEQRMDVKGRPYY VDVTKSTTWEDPRPE]GTLDEL[AGAGAGPEG]$_2$[RGDSAGPEG][AGAGA GPEG]$_3$ELLDGT([RLPAGWEQRMDVKGRPYYVDVTKSTTWEDPRPE]GTL DEL[AGAGAGPEG]$_2$[RGDSAGPEG][AGAGAGPEG]$_3$ELLDGT)$_x$[RLPAGW EQRMDVKGRPYYVDVTKSTTWEDPRPE]GTLE |
| N[y+2] | | ▒▒▒▒▒▒▒▒▒▒▒▒▒▒[PLPPGWEERTHTDGRVFF INHNIKKTQWEDPRMQ]GTLDEL[AGAGAGPEG]$_2$[RGDSAGPEG][AGAGA GPEG]$_3$ELLDGT([PLPPGWEERTHTDGRVFFINHNIKKTQWEDPRMQ]GTL DEL[AGAGAGPEG]$_2$[RGDSAGPEG][AGAGAGPEG]$_3$ELLDGT)$_y$[PLPPGW EERTHTDGRVFFINHNIKKTQWEDPRMQ]GTLE |
| P[z+2] | | ▒▒▒▒▒▒▒▒▒▒▒▒▒▒[EY▒Y▒▒▒Y▒SG]GTLDEL[AGAGAGPEG]$_2$ELLDGT([EY▒Y▒▒▒Y▒SG]GTLDEL[AGAGAGPEG]$_2$ELLDGT)$_z$[EY▒Y▒▒▒Y▒SG]GTLE |

FIG. 3

| Peptide | Schematic | Amino Acid Sequence |
|---|---|---|
| C7 | 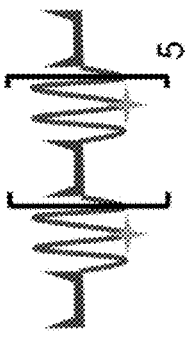 | MGSSHHHHHHSSGLVPRGSSGHIDDDDKVDGT [RLPAGWEQRMDVKGRPYFVDHVTKSTTWEDPRPE]GTLDEL [AGAGAGPEG]₂RGDSAGPEG[AGAGAGPEG]₂ELLDGT ([RLPAGWEQRMDVKGRPYFVDHVTKSTTWEDPRPE]GTLDEL[AG AGAGPEG]₂RGDSAGPEG[AGAGAGPEG]₂ELLDGT)₃ [RLPAGWEQRMDVKGRPYFVDHVTKSTTWEDPRPE]GTLE |
| P1 | • | EYPPYPPPPYPSG |
| P2 |  | EYPPYPPPPYPSGGGGGEYPPYPPPPYPSG |

FIG. 9

FIG. 13A
FIG. 13B
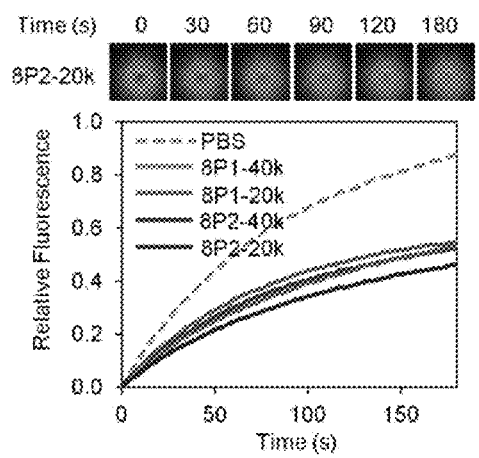
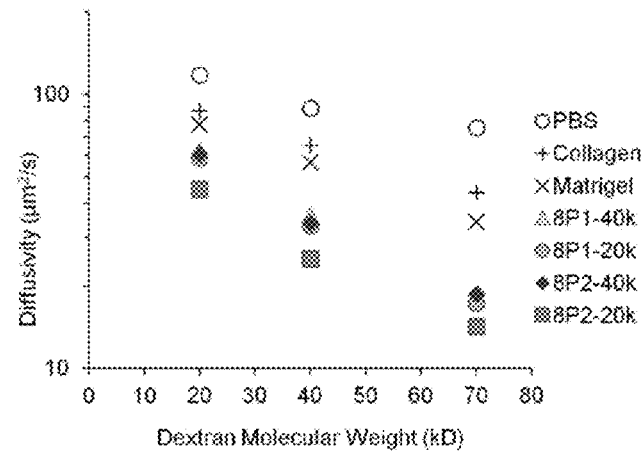
| | Diffusivity (µm²/s) | | |
|---|---|---|---|
| | 20 kD dextran | 40 kD dextran | 70 kD dextran |
| 8P2-20k | 45.1 ± 3.8 | 25.1 ± 2.0 | 14.2 ± 1.8 |
| 8P2-40k | 60.3 ± 3.4 | 33.9 ± 3.4 | 18.7 ± 3.5 |
| 8P1-20k | 58.4 ± 5.2 | 33.1 ± 1.5 | 17.3 ± 1.9 |
| 8P1-40k | 62.5 ± 8.1 | 36.2 ± 2.7 | 17.7 ± 3.5 |
| Collagen (2.5 mg/ml) | 87.3 ± 8.9 | 55.1 ± 2.8 | 43.8 ± 4.3 |
| Matrigel | 77.6 ± 5.8 | 56.5 ± 4.8 | 34.4 ± 2.0 |
| PBS | 117.6 ± 6.4 | 89.1 ± 7.0 | 75.5 ± 7.8 |
FIG. 13C

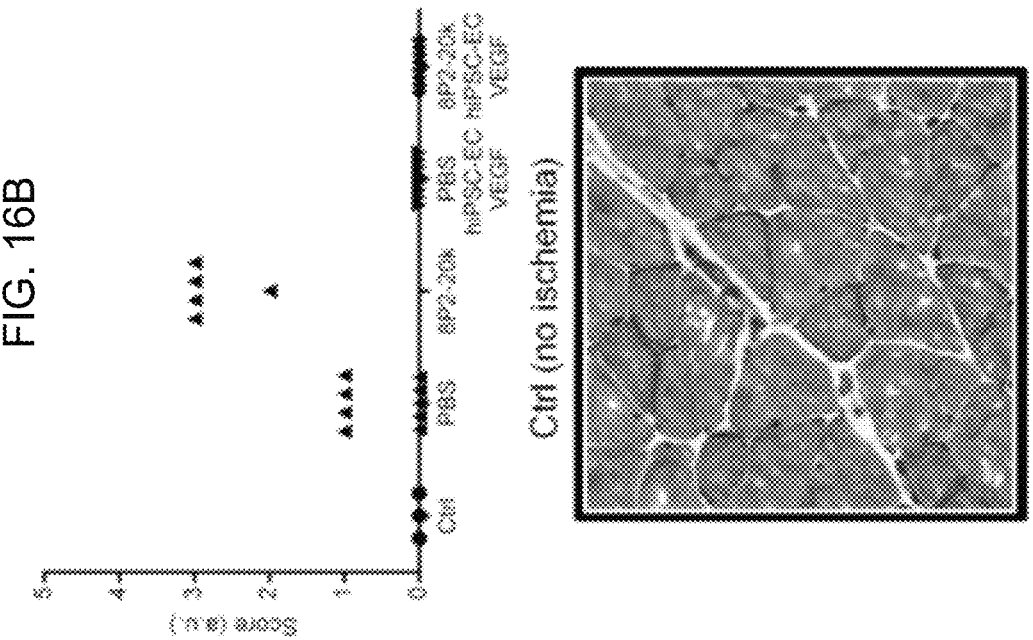
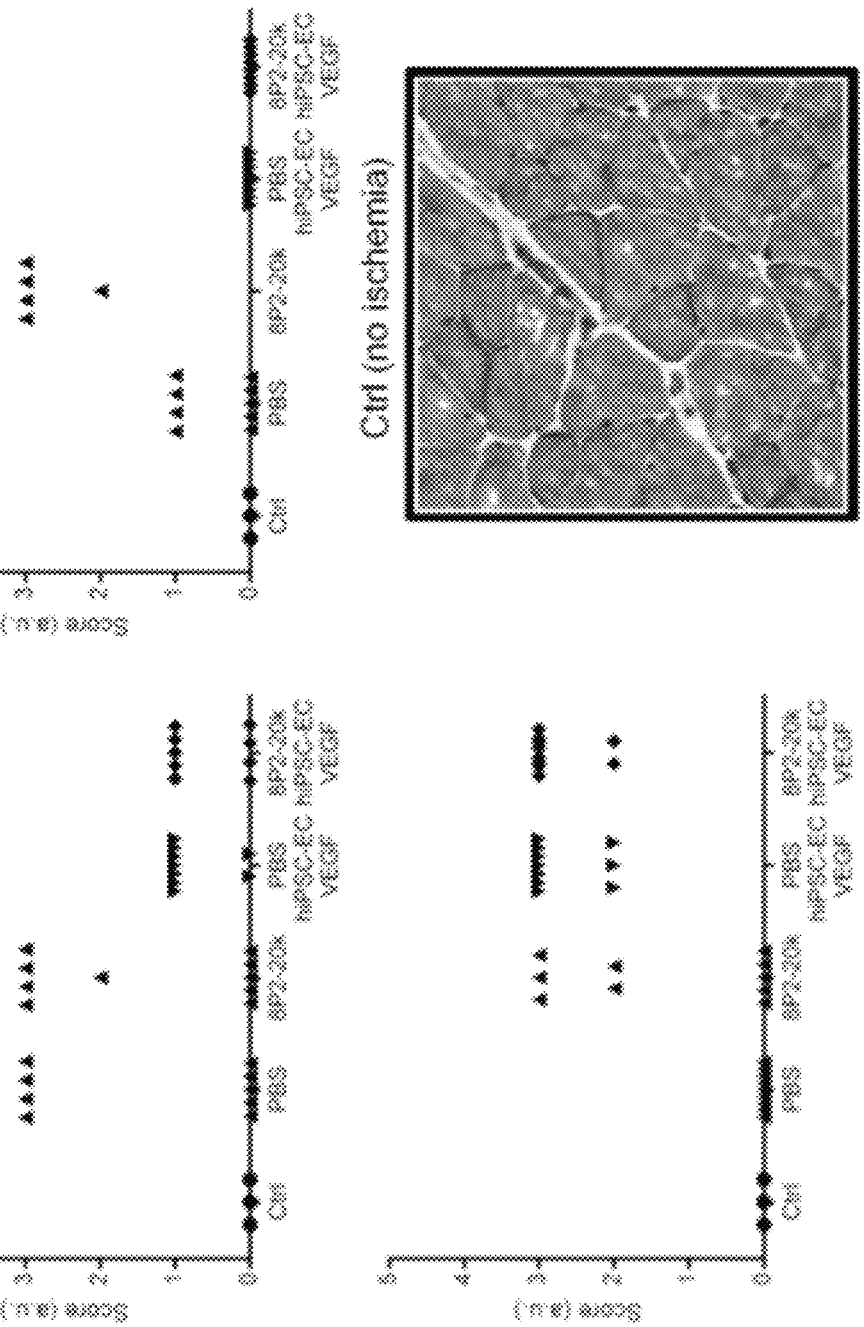
FIG. 16A  FIG. 16B  FIG. 16C  FIG. 16D

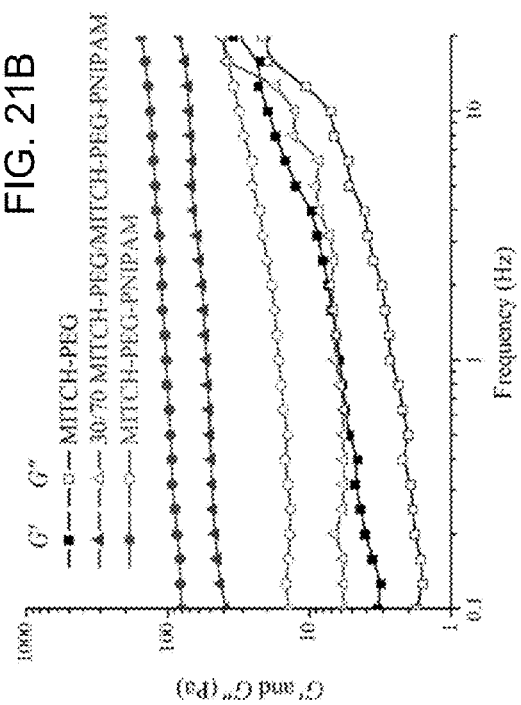
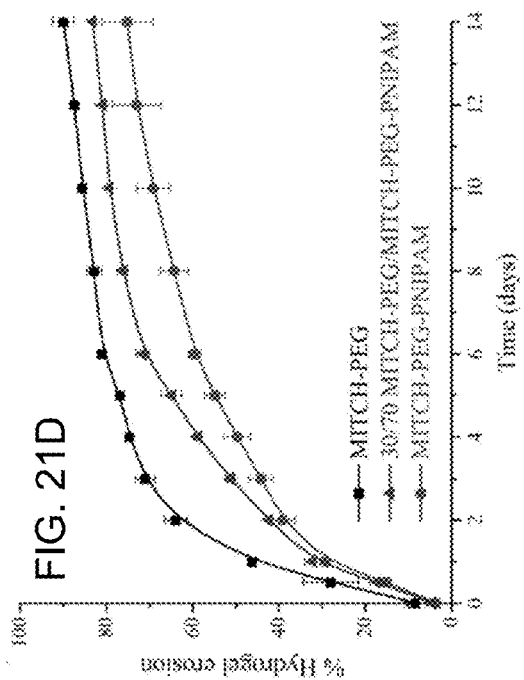
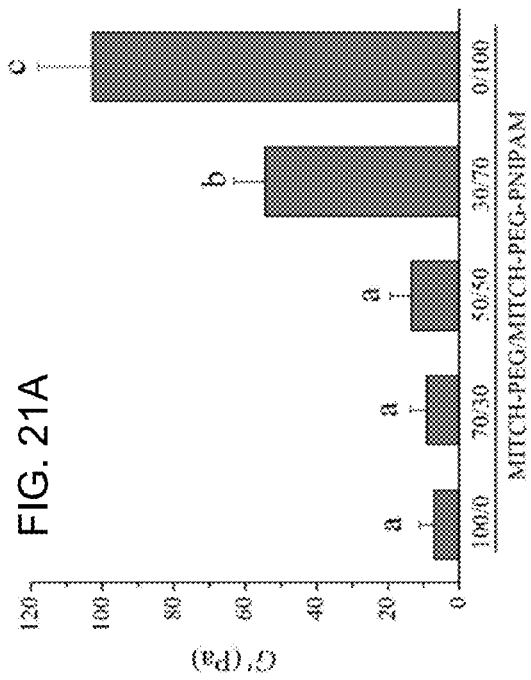
FIG. 21A
FIG. 21B
FIG. 21C
| Hydrogel System | Diffusivity (µm²/sec) |
|---|---|
| MITCH-PEG | 33.1 ± 1.5 |
| 30/70 MITCH-PEG/ MITCH-PEG-PNIPAM | 19.4 ± 2.8 |
| MITCH-PEG-PNIPAM | 14.9 ± 2.4 |
| Collagen | 54.1 ± 2.4 |
| Matrigel | 48.0 ± 1.0 |
| PBS (saline) | 89.1 ± 7.0 |
FIG. 21D

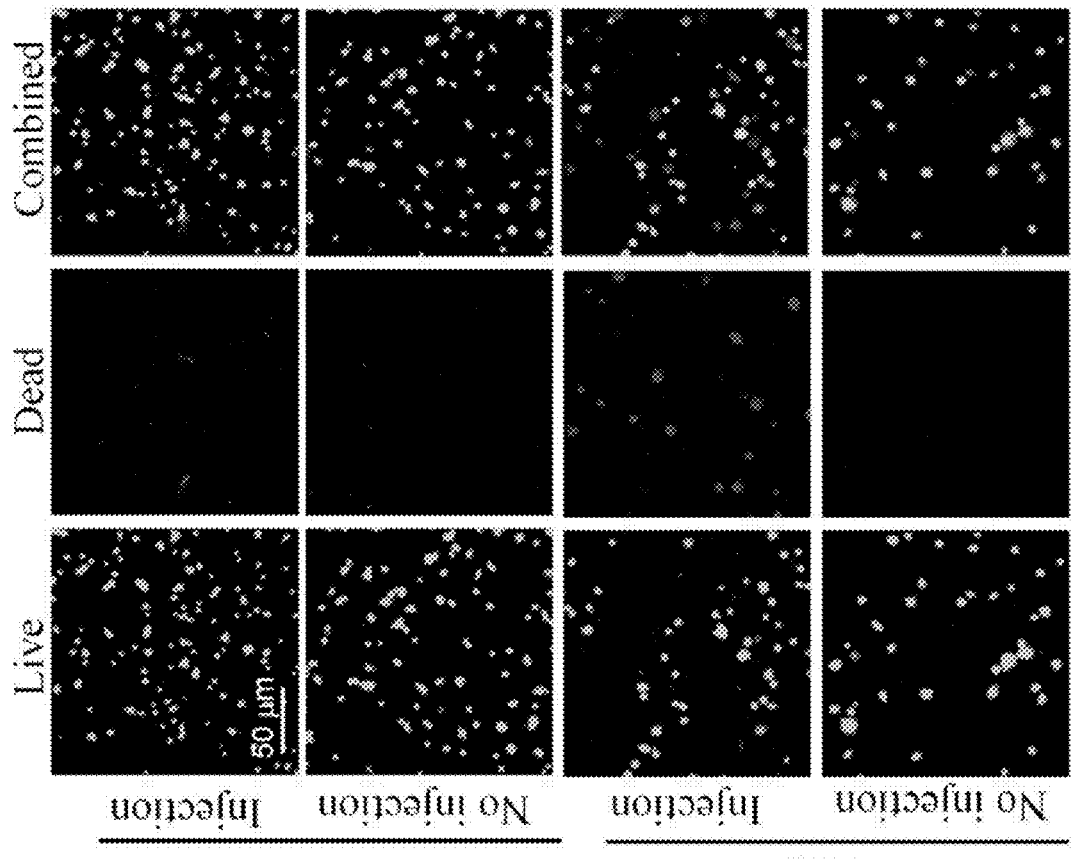
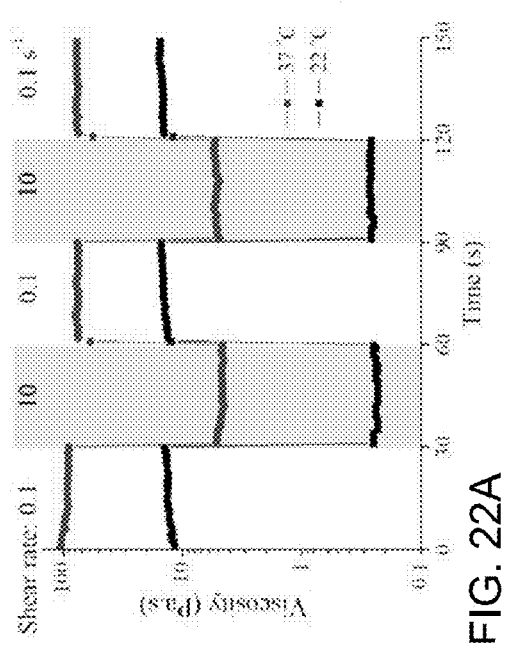
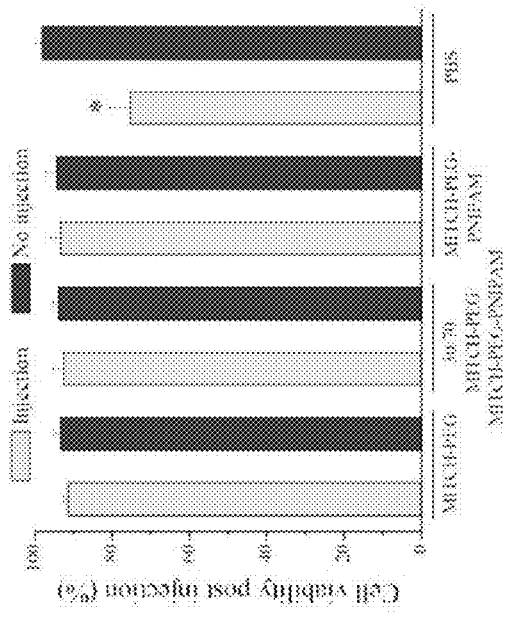
FIG. 22A
FIG. 22B
FIG. 22C

A: MITCH-PEG
B: 30/70 MITCH-PEG/MITCH-PEG-PNIPAM
C: MITCH-PEG-PNIPAM

A: PBS
B: MITCH-PEG
C: 30/70 MITCH-PEG/MITCH-PEG-PNIPAM
D: MITCH-PEG-PNIPAM

HETERO-ASSEMBLING, TUNABLE, AND INJECTABLE HYDROGELS FOR CELL ENCAPSULATION

CROSS-REFERENCE TO RELATED APPLICATIONS

This application claims priority from U.S. Provisional Patent Application 61/989,577 filed May 7, 2014, which is incorporated herein by reference. This application is a continuation-in-part of U.S. patent application Ser. No. 12/455,996 filed Jun. 9, 2009 (U.S. Pat. No. 9,011,914), which is incorporated herein by reference.

STATEMENT OF GOVERNMENT SPONSORED SUPPORT

This invention was made with Government support under contract nos. R01-DK085720, DP2-OD006477 awarded by the National Institutes of Health, and under contract no. DMR-0846363 awarded by the National Science Foundation. The Government has certain rights in the invention.

SEQUENCE LISTING

This application includes a sequence listing submitted in written form and in computer readable form on a compact disc.

FIELD OF THE INVENTION

The invention relates generally to hydrogels. In particular, the invention relates to viscoelastic hydrogels, methods of making viscoelastic hydrogels and methods of encapsulating cells, drugs, tissue, organs and the like in the viscoelastic hydrogels, and method of growing cells, tissue, organs and the like with the viscoelastic hydrogels.

BACKGROUND OF THE INVENTION

Cell transplantation is a proven method of treatment for certain immunological disorders and has shown promising effects for a variety of medical conditions including Parkinson's, Huntington's, stroke, spinal cord injury, myocardial infarction, and bone repair. Although a variety of transplanted progenitor cells and stem cells have had some degree of success in improving functional recovery, cell survival after transplantation is often poor and unpredictable, and has been directly correlated with functional outcome of the treatment in animal models. Therefore, there is a strong need to develop more reliable and efficient cell transplantation procedures.

Hydrogels are ideal materials for implantation because they introduce very low levels of foreign matter into the body and promote maximum diffusion of biomolecules throughout the scaffold due to their high water content. Hydrogel crosslinks can be either chemical, or physical. Since many chemical crosslinkers are toxic and result in non-injectable gels, physical hydrogels are preferred for many biomedical applications. Due to their unique structure, many physical hydrogels are shear-thinning, allowing them to be injected easily, an important criterion for non-invasive cell and drug delivery.

However, the assembly of polymers into physical hydrogels for cell encapsulation has mostly been governed by the use of external triggers. In these systems, cells are mixed with precursor macromolecules in the solution phase under specific environmental conditions. Following this, cells are encapsulated by exposure to a sudden change in pH, temperature, or ionic concentration to induce a solution to gel phase transition either in vitro or in situ. For example, common triggers for cell encapsulation by physical hydrogels include temperature sweeps from 4° C. to 37° C. for collagen and Matrigel; pH shifts from 2.0-2.5 to 7.4 for PuraMatrix and leucine-zipper systems; and cation concentration increases ranging from 20 to 200 mM for alginate and self-assembled peptide amphiphiles. These materials are generally designed to be in the gel phase at physiological conditions, requiring that cells be momentarily exposed to non-ideal environmental conditions in the sol phase (often a combination of low pH and temperature). Upon injection, the material equilibrates to physiological conditions and undergoes a phase change to the gel state. Because transplanted cells are highly sensitive to these non-physiological conditions, these triggers can be irreversibly detrimental to the encapsulated cells and accompanying proteins; and furthermore, these environmental conditions can be difficult to reproducibly control in a clinical setting. Therefore, current injection techniques within physical hydrogels can result in substantial loss of transplanted viable cells. This is of importance because cell viability and reproducibility in clinical settings have been directly correlated to the successful outcomes of these cell transplantation procedures. The present invention addresses at least some of the current problems and advances the art by introducing a physical hydrogel capable of encapsulating cells, drugs and proteins without subjecting them to variations in pH, temperature, or ionic strength.

SUMMARY OF THE INVENTION

A viscoelastic hydrogel based on a protein hetero-assembled with a polymer is provided. The protein cannot self-assemble with itself and the polymer cannot self-assemble with itself. The protein has a first association sequence (1stA) and a first spacer (1stSp). The polymer has a second association sequence (2ndA) and a second spacer (2ndSp). The first association sequence and the second association sequence are physically cross-linked to interact with each other with a 1:1 known and specific stoichiometry to form a three dimensional scaffold. The protein is represented by $\{1stA(1\ stSp)\}_x1stA$, where x is $\geq 2$, and the polymer is represented by $\{2ndA\ (2ndSp)\}_y2\ ndA$, where $y \geq 2$.

In one aspect, the protein is represented by $\{1stA(1stSp)_m\}_x1stA$, where m is 1 to 50, and x is 2 to 15; and the polymer is represented by $\{2ndA(2ndSp)\}_y2\ ndA$, where y is 2 to 64. In another aspect, the first association sequence is a WW protein sequence.

In yet another aspect, the second association sequence is 1, 2, 3 or 4 repeats of a polyproline-rich peptide sequence in series.

In yet another aspect, the second spacer is a branched polyethylene glycol.

In yet another aspect, the second spacer is a linear polyethylene glycol.

In yet another aspect, the second spacer has a molecular range in the order of 10-200 kDa.

In yet another aspect, the second spacer is a polypeptide or a polysaccharide.

In yet another aspect, the second spacer is a biopolymer alginate.

In yet another aspect, the polymer comprises a copolymer block of a stimuli-responsive polymer.

In still another aspect, the polymer comprises a copolymer block, wherein the copolymer block is a poly(n-isopropylacrylamide) and the resulting hydrogel contains 0-10 wt/vol % of poly(n-isopropylacrylamide).

BRIEF DESCRIPTION OF THE FIGURES

FIG. 1 shows an example of a two-component hydrogel system according to an embodiment of the invention.

FIG. 3 shows an example of the design, construction, and expression of WW Block Copolymers (C[x+2] or N[y+2]) and PolyProline-Rich Peptide Chains (P[z+2]) according to an embodiment of the invention. The figure shows the amino acid sequences of the two WW domains, a polyproline-rich peptide, and the hydrophilic spacers used in the design and construction of Components 1 and Components 2 of our physical hydrogel.

(FIG. 6A) Mean-squared displacement of micron-sized fluorospheres embedded within individual solutions of C7 or P9 (6 wt %) or within a hydrogel made from a 1:1 mixture, C7:P9 (6 wt %) plotted on a log-log scale confirms that the individual components cannot self-assemble into hydrogels. (FIG. 6B, FIG. 6C) Mean-squared displacement of micron-sized fluorospheres embedded within 5 to 10 wt % hydrogels made from a 1:1 mixture of C7:P9 or N7:P9, respectively. Tuning the association energy through choice of WW domain directly alters the viscoelastic properties of the gel.

(FIGS. 9A-B) Total DNA quantification shows PC-12 and adult NPC proliferation on control substrates and C7:P9 and N7:P9 films for 5d. Data are shown as mean±standard deviation, N=6; * represents statistically significant differences (p<0.001); ANOVA followed by Tukey post-test.

FIG. 9 shows amino acid sequences of C7, P1, and P2 according to an exemplary embodiment of the invention.

(FIG. 11A) Conjugation reaction scheme by Michael addition. (FIG. 11B) $^1$H NMR spectra of the 8-arm PEG-VS precursors and the 8-arm PEG-peptide conjugate products. The disappearance of the vinyl ($CH_2$=CH—) peaks from the precursors and the appearance of tyrosine doublets in the products (inset) confirm the conjugation reaction. Conjugation efficiency was calculated from the tyrosine:PEG backbone peak ratio. (FIG. 11C) Polyacrylamide gel electropherogram of the precursor peptides and the purified 8-arm PEG-peptide conjugates. Only one band is detected for each sample at various molecular weights, indicating purity and success of conjugation. Due to non-denaturing conditions, bands appear at positions different from those expected from the ladder standards.

(FIG. 12A) Binding isotherms obtained from isothermal titration calorimetry (ITC) injections of C1 peptide into P1 or P2. Table shows binding enthalpy and stoichiometry derived from fitting binding isotherms to an independent site model, demonstrating that C1 can only access a single P domain in either P1 or P2, thus maintaining a 1:1 stoichiometry. (FIG. 12B) Storage moduli (G', closed symbols) and loss moduli (G", open symbols) of MITCH-PEG variants as a function of frequency. (FIG. 12C) Linear shear viscosity measured under alternating shear rates, showing shear-thinning and self-healing behavior.

FIGS. 13A-C show Fluorescence Recovery After Photobleaching (FRAP) characterization of dextran diffusivity within MITCH-PEG variants according to an exemplary embodiment of the invention. (FIG. 13A) Representative time-lapse fluorescence images of a photobleached area (upper left panel) and the corresponding fluorescence recovery curves obtained from 40 kDa dextran (bottom). (FIG. 13B) Diffusivity constants derived from fluorescence recovery curves are plotted on a semi-logarithmic graph and reported in the table (FIG. 13C). Values obtained from encapsulation in common biomatrices (collagen and Matrigel) and Phosphate-Buffered Saline (PBS) are included for comparison.

(FIG. 14A) Cumulative release curves of 20 kDa dextran from MITCH-PEG into bulk PBS medium. Solid lines represent curve-fits for Fick's $2^{nd}$ law of diffusion from thin slabs. (FIG. 14B) Cumulative fraction of hydrogel material eroded into bulk PBS medium. (FIG. 14C) Quantification of $VEGF_{165}$ cumulative release by ELISA.

(FIG. 15B) Three-dimensional (3D) culture of hiPSC-ECs in 8P2-20k variant of MITCH-PEG. Visualization of cell morphology at day 4 of encapsulation by confocal immunofluorescence. Cell nuclei shown by DAPI staining in blue, F-actin cytoskeleton by phalloidin staining in green, and CD31 endothelial cell marker immunostaining in red (color represented by gray scale).

FIG. 16A-H show according to an exemplary embodiment of the invention histology scores of (FIG. 16A) inflammation, (FIG. 16B) necrosis, and (FIG. 16C) regeneration for a mouse hindlimb ischemia injury model. Scores were evaluated according to the criteria listed in the Methods. (FIG. 16D-H) Photomicrographs of cryosectioned samples of skeletal muscles 14 days after femoral artery ligation-induced ischemia. Hematoxylin and eosin (H&E) stained images of muscle tissue explants for (FIG. 16D) control tissue with no ischemia and ischemic tissue injected with (FIG. 16E) PBS, (FIG. 16F) 8P2-20k, (FIG. 16G) hiPSC-ECs and VEGF in PBS, and (FIG. 16H) hiPSC-ECs and VEGF in 8P2-20k. Inflammation, characterized by expansion of the connective tissues between myofibers, is marked with a blask asterisk in panels (FIG. 16E) and (FIG. 16F). Inflammatory cells in the connective tissues are marked with a white asterisk in panel (FIG. 16G).

FIGS. 21A-D show according to an exemplary embodiment of the invention rheological properties, diffusivity, and stability. (FIG. 21A) Shear storage moduli (G) of MITCH-PEG, MITCH-PEG-PNIPAM, and mixtures (ratios of 70/30, 50/50, 30/70) at 37° C. and 1 Hz. Different lower case letters denote samples with statistically significant differences ($p<0.05$, n=3). (FIG. 21B) Storage (G') and loss moduli (G") of MITCH-PEG, MITCH-PEG-PNIPAM, and a mixture (30/70) as a function of frequency at 37° C. (FIG. 21C) FRAP characterization of dextran (MW=40 kDa) diffusivity within hydrogels and phosphate buffered saline (PBS) at 37° C. (FIG. 21D) Hydrogel erosion kinetics represented by cumulative fraction of the hydrogel material eroded into bulk PBS medium over 14 days.

FIGS. 22A-C show according to an exemplary embodiment of the invention cell protective properties. (FIG. 22A) Shear thinning and self-healing of MITCH-PEG-PNIPAM under alternating shear rates of 0.1 and 10 $s^{-1}$ at 22 and 37° C. (FIG. 22B) Acute hASC viability following in vitro injection through a 28 G syringe needle at 1.0 mL/min. * $p<0.05$. (FIG. 22C) Fluorescence images of hASCs stained with LIVE/DEAD assay (green/red, respectively) within MITCH-PEG-PNIPAM or PBS post-injection.

(FIG. 24A) Fluorescence images of hydrogels conjugated with near-infrared dye at 0, 3, 7, 14, and 21 days post-injection. (FIG. 24B) Fluorescence imaging quantification of material retention relative to day 0. Different lower case letters denote samples with statistically significant differences ($p<0.05$, n=5).

(FIG. 25A) Bioluminescence images (BLI) of hASCs at 0, 3, 7, and 14 days post-injection. (FIG. 25B) BLI quantification of viable cell retention relative to day 0. Different lower case letters denote samples with statistically significant differences ($p<0.05$, n=4).

DETAILED DESCRIPTION

Figure 2:
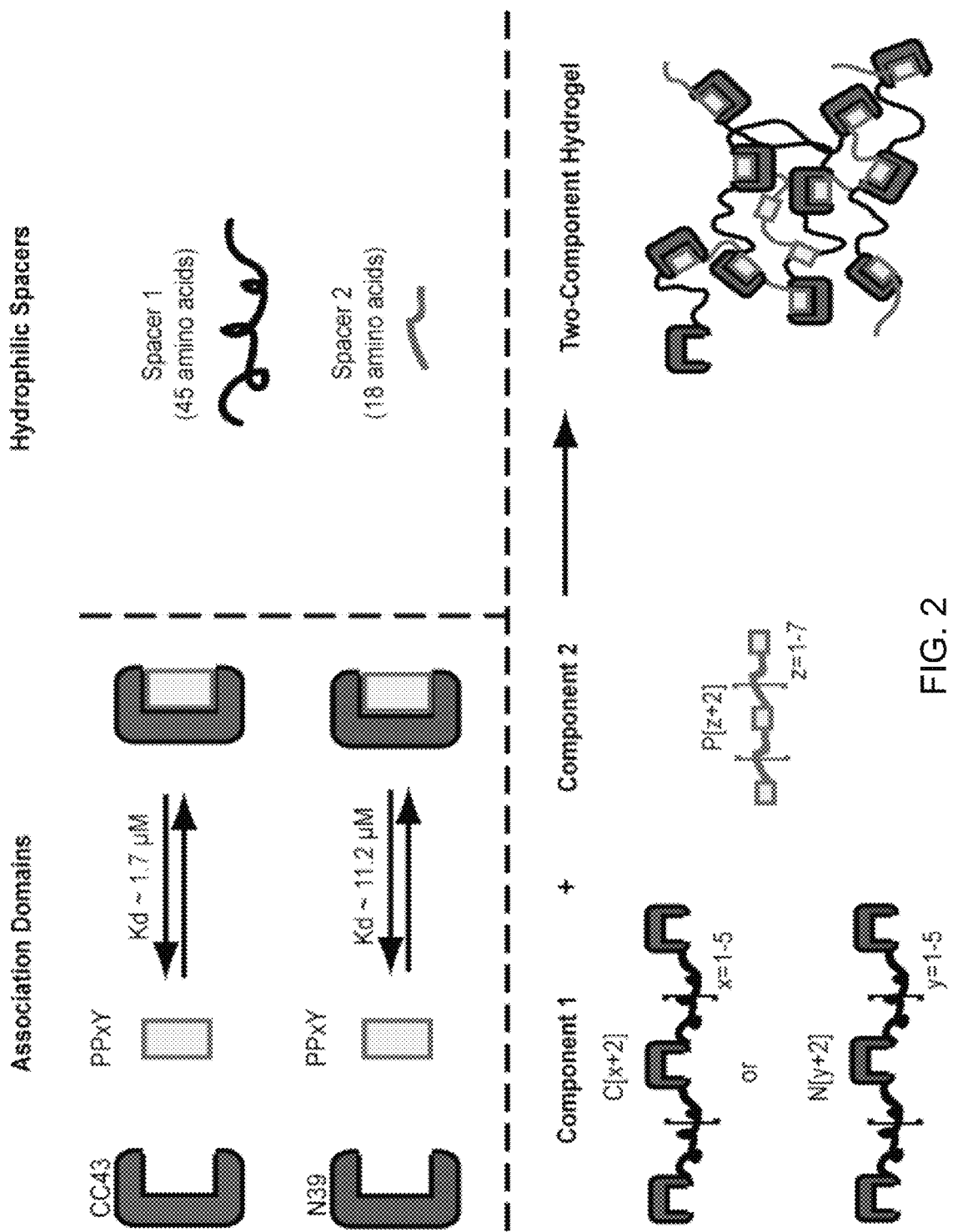
FIG. 2 shows an example of a design of the two-component, molecular-recognition hydrogel. Upper left panel: Modular association domains that assemble through molecular recognition. Both WW domains (CC43 and Nedd4.3) bind the same polyproline peptide (PPxY). Upper right panel: Hydrophilic spacers of varying lengths are used to link multiples repeats of WW domains (Spacer 1) or polyproline peptides (Spacer 2). Lower panel: Three engineered protein families: C[x+2], N[y+2], and P[z+2], made of multiple repeats of CC43, Nedd4.3, and PPxY, respectively. Mixing Component 1 (either C[x+2] or N[y+2]) with Component 2 at constant physiological conditions results in hydrogel formation via specific molecular-recognition interactions.

The embodiments presented in this invention relate to viscoelastic hydrogels (or "viscoelastic hydrogel scaffolds"), methods for making viscoelastic hydrogels, methods of encapsulating cells, drugs, tissue, organs, and the like, in the viscoelastic hydrogel, methods of growing cells, tissue, organs, and the like. Embodiments of this invention can be maintained in vivo, in vitro (e.g. in laboratory studies or diagnostics) as well as implanted in a host.

After fulfilling the purpose as the viscoelastic hydrogel, the viscoelastic hydrogel can dissolve or degrade, leaving nothing behind except the delivered drugs, proteins, or cells and/or the regenerated new cells, tissues, or organs. The methods of the invention permit the formation and preparation of structurally homogeneous viscoelastic hydrogels under physiological conditions. The mechanical and physical properties of the viscoelastic hydrogels can be controlled by controlling one or more parameters of the components used to form the viscoelastic hydrogel, which will be discussed in more detail infra.

The phrase "physiological conditions" refers to the range of solution conditions commonly encountered by cells, tissues, and organs in living hosts. For example, for humans, physiological conditions commonly refer to 37° C., a pH of about 7.4, and atmospheric pressure. These conditions will be specific to each particular host and may also vary for particular cells, tissues, and organs. The phrase "physiological buffer" refers to a buffered solution at physiological conditions. Examples of physiological buffers include, but are not limited to, phosphate-buffered saline (PBS) and Dulbecco's modified Eagle's medium (DMEM).

In general, embodiments of the viscoelastic hydrogel include a first protein and a second protein. The first protein and the second protein are each independently free flowing in a buffer solution or other solution at physiological conditions. The first protein includes a first association sequence and a first spacer. The second protein includes a second association sequence and a second spacer. When the two are mixed at physiological conditions, the first association sequence and the second association sequence bind together through non-covalent bonds (e.g., hydrogen bonds, van der Waal bonds, electrostatic bonds) to form physical crosslinks to form a three dimensional scaffold. In this regard, the first protein and the second protein hetero-assemble when mixed together. The term hetero-assembly is used to denote spontaneous assembly of different associating parts. Equivalent terms to hetero-assembly are bi-assembly or coupled-assembly to more specifically indicate that only two groups are associating as taught in the present invention.

The first protein and the second protein can be mixed together in a buffer solution or in another environment. In contrast to other hydrogels, embodiments of this invention can form a viscoelastic hydrogel without the need for crosslinkers, ultraviolet radiation, a catalyst, and/or sudden shifts in pH, ionic strength, and/or temperature. Embodiments of this invention can form a viscoelastic hydrogel in or at constant physiological conditions (e.g., in a physiological buffer solution having physiological conditions or in a host). The term "constant" in this context is used to distinguish from other hydrogel systems that change the pH, temperature, and the like to cause formation of the hydrogel.

Embodiments of this invention are advantageous over traditional synthetic chemistry for at least the following reasons. First, protein-based viscoelastic hydrogel scaffolds are composed entirely of amino acids and are therefore biodegradable and have displayed good biocompatibility. Second, using genetic templates to synthesize the viscoelastic hydrogel scaffold material affords absolute control over the molecular-level design, allowing systematic optimization of the scaffold properties. Third, peptide sequences derived from the extracellular matrix are directly incorporated into the viscoelastic hydrogel scaffold to mimic the natural extracellular matrix of cells, enhancing cell adhesion, viability, and migration. Unlike currently available hydrogels for cell culture experiments and medical therapies, embodiments of the viscoelastic hydrogel system do not require chemical crosslinkers or shifts in environmental conditions to induce gelation. Embodiments of the viscoelastic hydrogel can encapsulate cells, tissues, organs, drugs, and proteins at constant physiological conditions, therefore, embodiments of the present disclosure are highly biocompatible.

Embodiments of the viscoelastic hydrogels of this invention are useful in any situation in which a hydrogel is useful. In an embodiment, the viscoelastic hydrogel can be used to encapsulate and/or grow cells or cell cultures of a single type or multiple types, tissues, and/or organs. In an embodiment, the cells may be integrated with the viscoelastic hydrogel using a variety of methods. For example, the viscoelastic hydrogel may be submersed in an appropriate growth medium for the cells of interest, and then directly exposed to the cells. The cells are allowed to proliferate on the surface and migrate into and through the viscoelastic hydrogel. The viscoelastic hydrogel is then removed from the nutrient medium (which can vary depending on cell type), washed if necessary, and implanted.

In another embodiment, the cells of interest are dispersed into an appropriate solution (e.g., a growth medium or buffer) that contains either the first protein or the second protein; the solution will be a freely flowing liquid. Then, the other of the first protein or the second protein is added to the solution, causing the formation of a three dimensional, viscoelastic hydrogel. This hydrogel cell construct can be directly injected into a host using a syringe or implanted into the host.

In another embodiment, the cells of interest are dispersed into an appropriate solution (e.g., a growth medium or buffer) that contains either the first protein or the second protein. This freely flowing solution can be loaded into a syringe (either single barrel or double barrel) and injected into the host as a freely flowing solution. Injection of the other of the first protein or the second protein can be simultaneous (through use of a double barrel syringe) or subsequent (through use of a second single barrel syringe) to induce gelation within the host.

The cells that may be incorporated on or into the viscoelastic hydrogel include, but are not limited to, stem cells, precursor cells, smooth muscle cells, skeletal myoblasts, myocardial cells, endothelial cells, endothelial progenitor cells, bone-marrow derived mesenchymal cells, genetically modified cells, neurons, and the like.

In another embodiment, the viscoelastic hydrogels of this invention can be used to make implantable medical devices where the viscoelastic hydrogel portion(s) of the device includes biologically active molecules (e.g., compositions useful for treating a disease in a mammal, compositions useful for ensuring acceptance of the device, and the like). In an embodiment, the biologically active molecules are released from the viscoelastic hydrogel after the device is implanted into a living body. Thus, these embodiments of implantable medical devices can be used, for example, as drug delivery devices that release a specific dosage of a drug that is effective to ameliorate the symptoms of a disease in a living body, such as a mammalian body (e.g., a human body).

An embodiment of this invention provides for methods for forming a viscoelastic hydrogel at a site of application. The methods for forming a viscoelastic hydrogel at a site of application include combining a first component and a second component at the site of application to form a viscoelastic hydrogel at physiological conditions. In an embodiment, the viscoelastic hydrogel is formed at the site of a wound in a living body, such as a host (e.g., a human body). The viscoelastic hydrogel may fill in, or repair, a missing or damaged portion of tissue, and/or may deliver biologically active molecules (e.g., therapeutic agents) to a damaged portion of a living body, thereby promoting wound healing. In some embodiments, the methods may be used to apply stem cells (or other cells), included within one or both of the first component or the second component used to form the viscoelastic hydrogel or disposed after formation of the viscoelastic hydrogel, to a damaged portion of a living body. The stem cells thereafter divide and differentiate to form cells, tissue, or the like, that repair the damaged portion of the living body.

Viscoelastic Hydrogel Components and Structure

As noted above, the viscoelastic hydrogel includes a first protein and a second protein. The first protein and the second protein are each independently free flowing in a buffer solution at physiological conditions. The first protein includes a first association sequence and a first spacer. The second protein includes a second association sequence and a second spacer. When the two are mixed at physiological conditions, the first association sequence and the second association sequence bind through secondary, physical bonds (e.g., hydrogen bonds, electrostatic interactions, dipole-dipole bonds) with a specified stoichiometry. These associating sequences form physical crosslinks that link the proteins into a network that form a three-dimensional viscoelastic hydrogel. In this regard, the first protein and the second protein hetero-assemble to form the viscoelastic hydrogel when mixed together. The first protein and the second protein can be mixed together in a buffer solution or in another environment.

In an embodiment of the present disclosure, a cell-binding peptide can be associated with (attached directly or indirectly) the viscoelastic hydrogel or with the first protein and/or the second protein prior to forming the viscoelastic hydrogel. In an embodiment, the cell-binding peptide is incorporated into the first spacer and/or the second spacer. Table 1 includes a listing of some exemplary cell-binding peptides and their putative receptors.

In an embodiment, the cell-binding peptide can be used to bind to the cells integrated in the viscoelastic hydrogel. In another embodiment, the cell-binding peptide can be used to bind to cells or tissue at the place of introduction to the host. In yet another embodiment, the viscoelastic hydrogel can include multiple types of cell-binding peptides having different purposes or resulting in synergistic effects.

The first protein is represented by $\{1stA(1stSp)_n\}_x 1stA$, where:
1stA is the first association sequence,
1stSp is the first spacer, and
m is 1 to 50, and x is 2 to 15.

The second protein is represented by $\{2ndA(2ndSp)_n\}_y 2ndA$, where:
2ndA is the second association sequence,
2ndSp is the second spacer, and
n is 1 to 50, and y is 2 to 15.

For both x and y, 2 is the minimum number required to form an interconnected network. The subscripts m and n are non-integer multiples of one another. FIG. 1 is a schematic of an embodiment of the first protein (shown as protein A) and the second protein (shown as protein B). The circle is the first association sequence and the looped line in the parentheses with the subscript m is the first spacer. The tilde symbol is the second association sequence and the looped line in the parentheses with the subscript n is the second spacer.

Table 2 illustrates a number of variables that can affect one or more properties of embodiments of the viscoelastic hydrogel. In addition, Table 2 illustrates the effects that each variable has on the viscoelastic hydrogel. It should be noted that one or more of the variables can be adjusted for an embodiment of the viscoelastic hydrogel to vary one or more of the properties of the viscoelastic hydrogel.

TABLE 1

Examples of cell-binding peptides for inclusion in hetero-assembling hydrogels. List modified from Table I in "Functional peptide sequences derived from the extracellular matrix glycoproteins and their receptors: Strategies to improved neuronal regeneration" by Sally Meiners, Mary Lynn T. Mercado and published in Molecular Neurobiology 2003-27(2): 177-195.

| Peptide | Molecular Origin | Domain or Region | Putative Receptor |
|---|---|---|---|
| VFDNFVLK | Tenascin-C | fnD | α7β1 integrin |
| EIDGIELT | | fzn3 | α9β1 integrin |
| RGD | | fn3 | α8β1, αvβ3 integrins |
| RGD | Fibronectin | fn10 | α3β1, α5β1, α7β1, α8β1, αvβ1, αvβ3, αvβ6 integrins |
| LDV | | IIICS-CS I | α4β1 integrin |
| REDV | | IIICS-CS V | α4β1 integrin |
| EDGIHEL | | EDA | α4β1, α9β1 integrins |
| RDIAEIIKDI | Laminin-1 | γ 1 chain | Unidentified G-protein coupled receptor |
| IKVAV | | α 1 chain | β-amyloid precursor protein (APP) |
| YIGSR | | β 1 chain | 67 kDa YIGSR-binding protein |
| IKLLI | | α 1 chain | α3β1 integrin |
| RGD | | α 1 chain | α6β1, αvβ3 integrins |
| RKRLQVQLSIRT | | α 1 chain | |
| KNRLTIELEVRT | Laminin-2 | α 1 chain | |
| LRE | s-Laminin | α 2 chain | |

TABLE 2

Examples of variables affecting the properties of the hetero-assembling hydrogels.

| Component | Variables | Effect on Hydrogel Properties |
|---|---|---|
| Protein A and B association domains | A:B or B:A stoichiometry | Increasing the A:B or B:A stoichiometry above 1:1 yields stiffer gels |
| | A:B kinetic association on-rate, $k_{on}$ | Larger $k_{on}$ (ie, faster association rates) yield faster gelation times |
| | A:B kinetic association off-rate, $k_{off}$ | Larger $k_{off}$ (ie, faster dissociation rates) yield faster relaxation and erosion times |
| | A:B thermodynamic dissociation constant, $K_d$ | Smaller $K_d$ (where $K_d = k_{off}/k_{on}$) yields stiffer gels with more equilibrium cross-links and slower erosion times |
| | Number of A and B association domains per molecule (x + 1 and y + 1) | More association domains per molecule yield stiffer hels with slower erosion times |
| Hydrophylic spacer domains | Length of spacer sequence in component A (m) | Longer chains promote chain entanglement and slower relaxation and erosion times |
| | Length of spacer sequence in component B (n) | Longer chains promote chain entanglement and slower relaxation and erosion times |

TABLE 2-continued

Examples of variables affecting the properties of the hetero-assembling hydrogels.

| Component | Variables | Effect on Hydrogel Properties |
|---|---|---|
| | Relative ratio of spacer sequences (m/n) | Non-integer ratios promote efficient gelation by preventing multiple cross-links between the exact same two molecular chains |
| Cell-binding peptides (can be included within the hydrophilic spacers of Component A and/or Component B) | Identity of binding peptide | Determines which cell types can bind to the gel and the strength of binding |
| | Number of binding peptides including in each spacer domain | Alters the cell signaling |
| | Location of binding peptides included in each spacer domain | Alters the cell signaling |

Embodiments of the first association sequence or the second association sequence are selected from proteins that at physiological conditions can associate (hetero-assemble) with one another through non-covalent bonds (e.g., hydrogen bonds, van der Waal bonds, electrostatic bonds) to form physical crosslinks to form a three dimensional scaffold. In general, the first association sequence and the second association sequence have sequences that allow them to fold into a specific conformation and to interact with each other physically through specific, non-covalent secondary bonds. Both the first and second association sequences should not be able to hetero-associate with themselves. Both the first and second association sequences must be suitable for synthesis using recombinant molecular biology techniques.

Other variables to be considered when choosing appropriate association sequences are listed in Table 2 along with their effects on the hydrogel properties. The first and second association sequences may bind together with 1:1 stoichiometry; increasing the stoichiometry ratio will increase the relative stiffness of the resulting hydrogel. Association sequences with varying kinetics and thermodynamics of binding will tune the resulting viscoelastic properties of the hydrogel. For example, association sequences with larger on-rates, $k_{on}$, will have faster association rates and yield materials with faster gelation times. Association sequences with larger off-rates, $k_{off}$, will have faster dissociation rates and yield materials with faster relaxation and erosion times. Association sequences with smaller thermodynamic equilibrium dissociation constants, $K_D$ (where $K_D=k_{off}/k_{on}$), will yield stiffer gels with more equilibrium crosslinks and slower erosion times.

In an embodiment, one of the first association sequence or the second association sequence can be a WW block copolymer and the other of the first association sequence or the second association sequence can be a polyproline-rich peptide (See Example for more details). These two association sequences were selected for one or more of the following criteria: i) The interactions between the WW domain and the polyproline-rich peptide are well understood and can be tuned across a range of dissociation constants. The reversible association of these two sequences when mixed together will provide the transient physical crosslinks that allow the scaffold to form a hydrogel. ii) The WW domain forms a robust fold (a short triple-stranded anti-parallel beta-sheet secondary structure) and has been successfully expressed in and purified from *E. coli* fermentation. iii) These domains naturally occur intracellularly therefore, they are not expected to interfere with external cellular signaling if they are presented to the cells as part of an extracellular hydrogel scaffold.

Separately, these two components form free flowing solutions in physiological buffer; however, upon mixing, the WW domains will associate with the polyproline-rich peptides through hydrogen bonding to form physical crosslinks between chains. By varying the dissociation constant between the two proteins, the number of repeating WW or PP blocks per chain, or the length of the hydrophilic spacer, we are able to tune the time-dependent hydrogel rheology. Additional details are described in Examples.

Embodiments of the first spacer and the second spacer can be selected from hydrophilic spacer protein sequences. The first spacer and the second spacer are not required to be the same protein domains (but can be the same if desired, just repeated a different number of times). In an embodiment, one of the first spacer and second spacer may be longer than the other to accommodate the different length and/or folding of the first association sequence and/or the second association sequence. In an embodiment, the first spacer and/or second spacer can be selected to modify one or more of the characteristics of the viscoelastic hydrogel scaffold. In another embodiment, the first spacer and/or second spacer can include a cell-binding peptide, such as those noted above.

In general, the selection of the first spacer and/or second spacer can be conducted to accommodate the formation of the viscoelastic hydrogel scaffold. Choosing longer spacer sequences will promote chain entanglement and slower relaxation and erosion times (FIG. 1 and Table 2).

In an embodiment, the length of the first spacer was chosen to form a random coil with an estimated diameter equal to 1.5 times the length of a folded WW domain, AGAGAGPE-GAGAGAGPEG (e.g. see FIG. 3, SEQ ID No:6). The second spacer was chosen to be a non-integer multiple in length (5/2 times the length of the first spacer) to prevent multiple association sites on one molecule of component A from interacting with multiple association sites on one molecule of component B (i.e., to prevent two molecules from "zipping" up). In this same example, the RGD amino acid cell-binding peptide was included in the second spacer.

In an embodiment, any other known cell-binding peptide can be included in either the first and/or second spacers. Examples of known cell-binding peptides are listed in Table 1.

In an embodiment, multiple cell-binding peptides can be included in a single spacer domain or in various combinations of the spacer domains. Varying the number and identity of cell-binding peptides in the spacer domains can be used to control the density of cell-binding events that can occur between the hydrogel and an integrated cell.

The hydrophilic spacer can be any sequence known to form a random coil that links together multiple association domains and promotes water solubility. An alternative example of a hydrophilic spacer sequence is repeats of the peptide sequence GGGS. The overall number of repeats of the association domain and the hydrophilic spacer sequence can also be tuned for both components (Table 2 and FIG. 1). Including more repeats of an association domain per single molecular chain will yield stiffer gels with slower erosion times.

Methods of Making the Viscoelastic Hydrogel

The invention includes methods of making viscoelastic hydrogels. In general, the first protein and the second protein can be mixed under physiological conditions to form a viscoelastic hydrogel.

In an embodiment, the first protein and the second protein can be mixed under physiological conditions in a buffer solution that is at physiological conditions. Embodiments of the buffer solution include, but are not limited to, phosphate buffered saline, Dulbecco's modified Eagle's medium, and other known mammalian cell culture media. The first protein and the second protein can be mixed in the buffer solution and are about 1-20% by weight of the mixture.

In another embodiment, the first protein and the second protein can be mixed in a host or at a position within a host, where the conditions for the mixture are at physiological conditions. In an embodiment, the first protein and the second protein can be mixed at the site of an injury or procedure (e.g., operation).

In an embodiment, one or more types of cells can be added to the viscoelastic hydrogel after it is formed, while in another embodiment, one or more types of cells can be added to one or both of the first protein or the second protein prior to forming the viscoelastic hydrogel. In an embodiment, one or more cells can be added prior to and after the formation of the viscoelastic hydrogel.

In an embodiment, appropriate nutrients can be added to the viscoelastic hydrogel before or after formation of the viscoelastic hydrogel and/or before or after addition of one or more types of cells.

Kits

The invention also provides the first protein and the second protein, and directions of use. In addition, embodiments of the present disclosure can include buffers and other components to assist in using embodiments of the present invention.

EXAMPLES

Now having described the embodiments of the invention, in general, the following example describes some additional embodiments. While embodiments of the invention are described in connection with the example and the corresponding text and figures, there is no intent to limit embodiments of the invention to these descriptions. On the contrary, the intent is to cover all alternatives, modifications, and equivalents included within the spirit and scope of embodiments of the present disclosure.

In this example, we utilized the concept of protein-protein interactions between specific peptide domains to design a two-component, molecular-recognition physical hydrogel system. The two components each contain separate peptide domains that associate together upon mixing under constant physiological conditions (FIG. 2). Therefore, this two-component hetero-assembly strategy is tailor-made to encapsulate cells and proteins without subjecting them to variations in pH, temperature, or ionic strength. This assembling strategy should make the system easy to use and clinically friendly as the gel will form simply upon mixing of the two components, similar to the formation of two-component polymeric epoxies.

Three criteria were used to select the association domains for our engineered proteins. First, their amino acid sequences must be short to allow multiple domains to be repeated in a single polymer that expresses well in a recombinant host. Second, the domains must be naturally found intracellularly so as not to interfere with external cell signaling when presented as part of a hydrogel matrix. Third, the domain association should be stable and tunable. The WW domain and the proline-rich peptide, two small peptide domains that associate together, were found to meet these criteria. The WW domain (~31-40 amino acids) adopts an anti-parallel, triple-stranded β-sheet conformation and has shown surprising specificity and affinity for proline-rich peptides despite its non-conserved sequences. Many WW domain sequences have been identified in nature and derived computationally. In this example, we chose two WW domains, the computationally-derived CC43 (Russ, W. P., Lowery, D. M., Mishra, P., Yaffe, M B. & Ranganathan, R. (2005) *Natural-like function in artificial WW domains. Nature* 437:579-83) and the wild-type sequence Nedd4.3 (Kanelis, V., Rotin, D. & Forman-Kay, J. D. (2001) *Solution structure of a Nedd4 WW domain-ENaC peptide complex. Nat Struct Biol* 8:407-12; Russ, W. P., Lowery, D. M., Mishra, P., Yaffe, M. B. & Ranganathan, R. (2005) *Natural-like function in artificial WW domains. Nature* 437:579-83) (Protein Data Bank 1I5H), reported to differ by an order of magnitude in their association constants with group I proline-rich peptides (PPxY). Multiple repeats of each association domain were linked together with random coil hydrophilic spacers to form three separate families of engineered recombinant proteins with varying chain lengths (FIGS. 2-3). The hydrophilic spacers were hypothesized to add flexibility to the protein chains, thereby facilitating accessibility and binding between the WW and PPxY domains. We designed the length of hydrophilic spacer 1, which links multiple WW domains, to be equal to or greater than the length of a single WW domain (~25 Å based on X-ray crystallography) assuming the spacer has a self-avoiding random coil configuration. The length of hydrophilic spacer 2, which links multiple PPxY domains, was chosen to be a non-integer multiple (2/5) of spacer 1 to minimize the possibility of several physical crosslinks forming between a single component 1 chain and a single component 2 chain, i.e., "zipping up" of pairs of molecules, which would prevent formation of a fully linked network.

Results

Figure 4A:
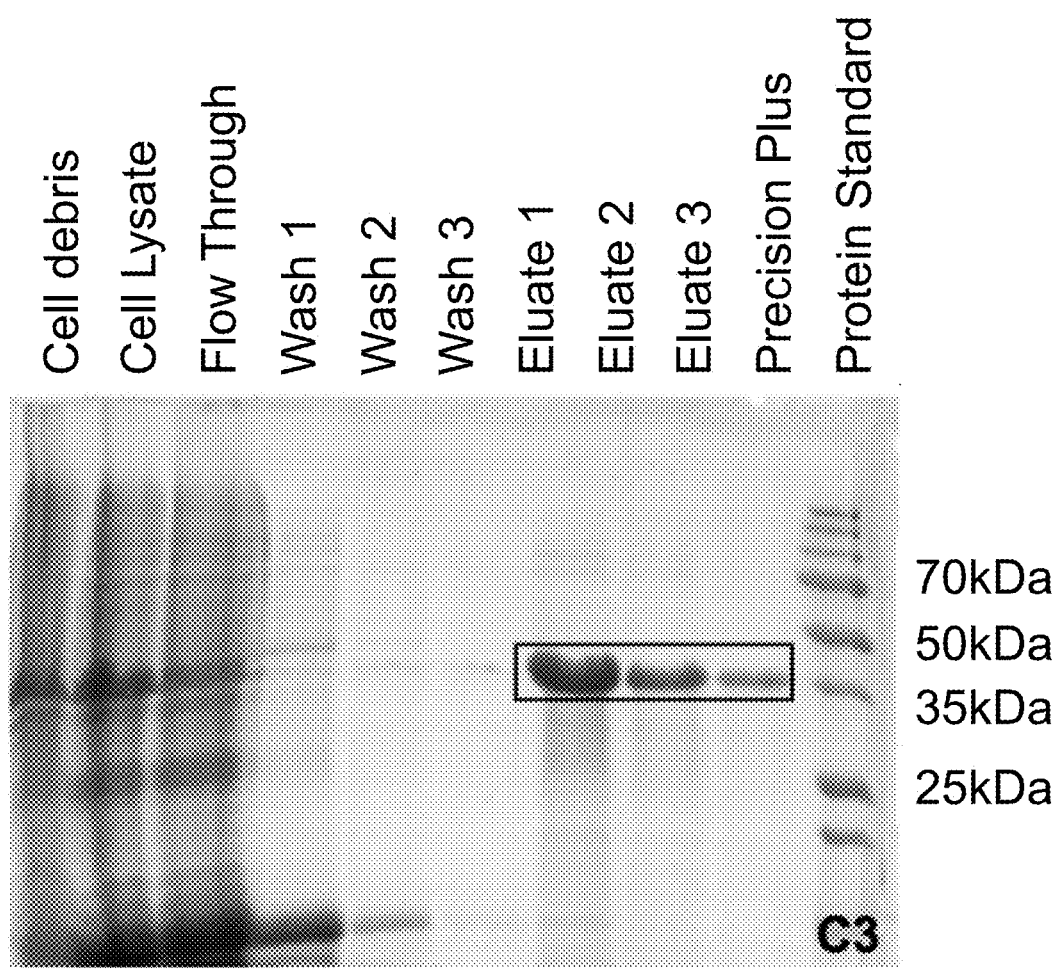
FIGS. 4A-C show examples of SDS PAGE electrophoresis showing the expression and purification of C3 (FIG. 4A), N3 (FIG. 4B), and P3 (FIG. 4C). C[x+2], N[y+2], and P[z+2] that were successfully expressed in *Escherichia coli* BL21(DE3) host strain (Novagen, San Diego, Calif.) upon induction with 0.5 mM isopropyl β-D-1-thiogalactopyranoside (IPTG). The recombinant proteins were purified via specific binding of their 6×His tag to Ni-NTA resin (Qiagen, Valencia, Calif.). The apparent molecular weights as observed by SDS gel electrophoresis are significantly larger than the actual molecular weights. The low mobility of these proteins can be explained by the highly acidic and hydrophilic nature of the spacers, which bind the anionic surfactant SDS weakly, resulting in a reduced overall effective charge in the electrophoretic separation process. Molecular weights were confirmed by MALDI-MS.
Figure 4B:
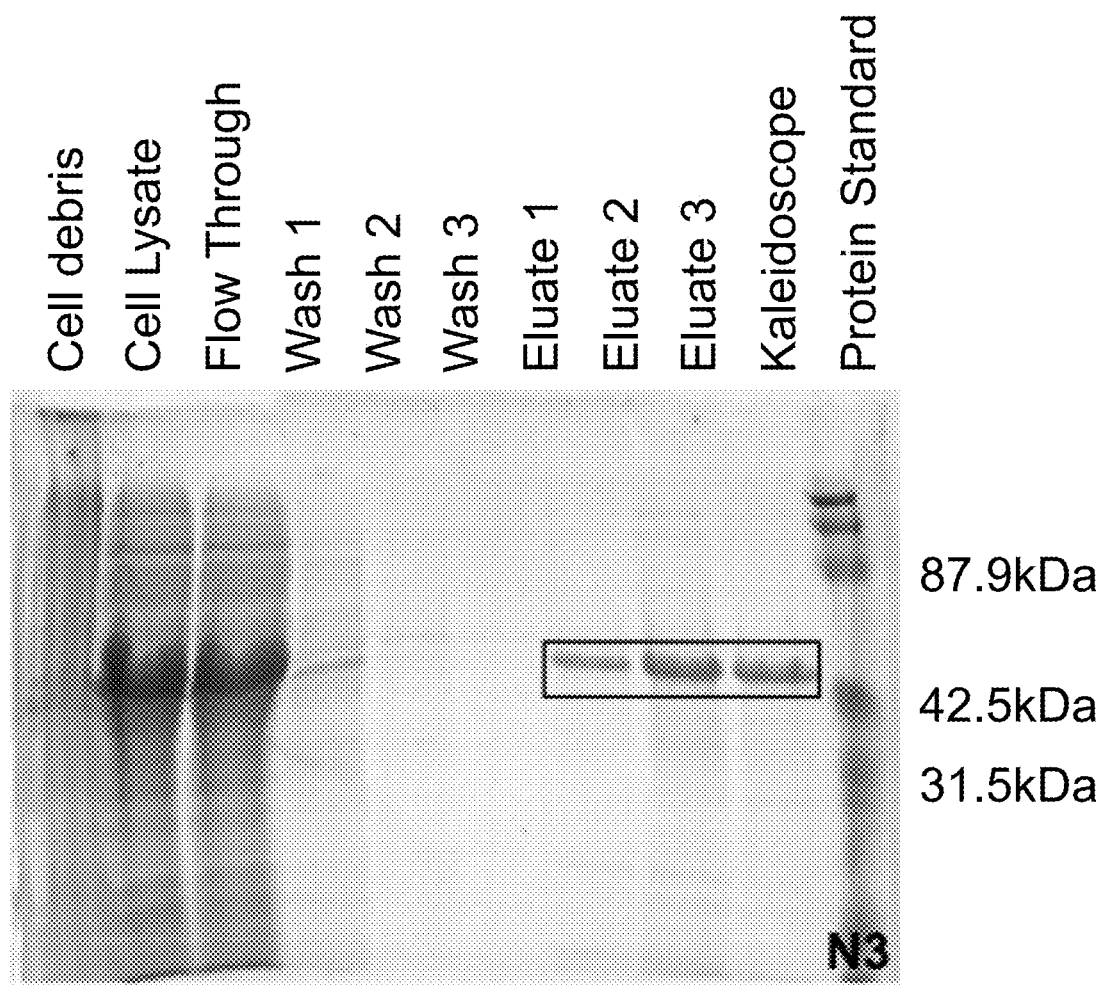
Figure 4C:
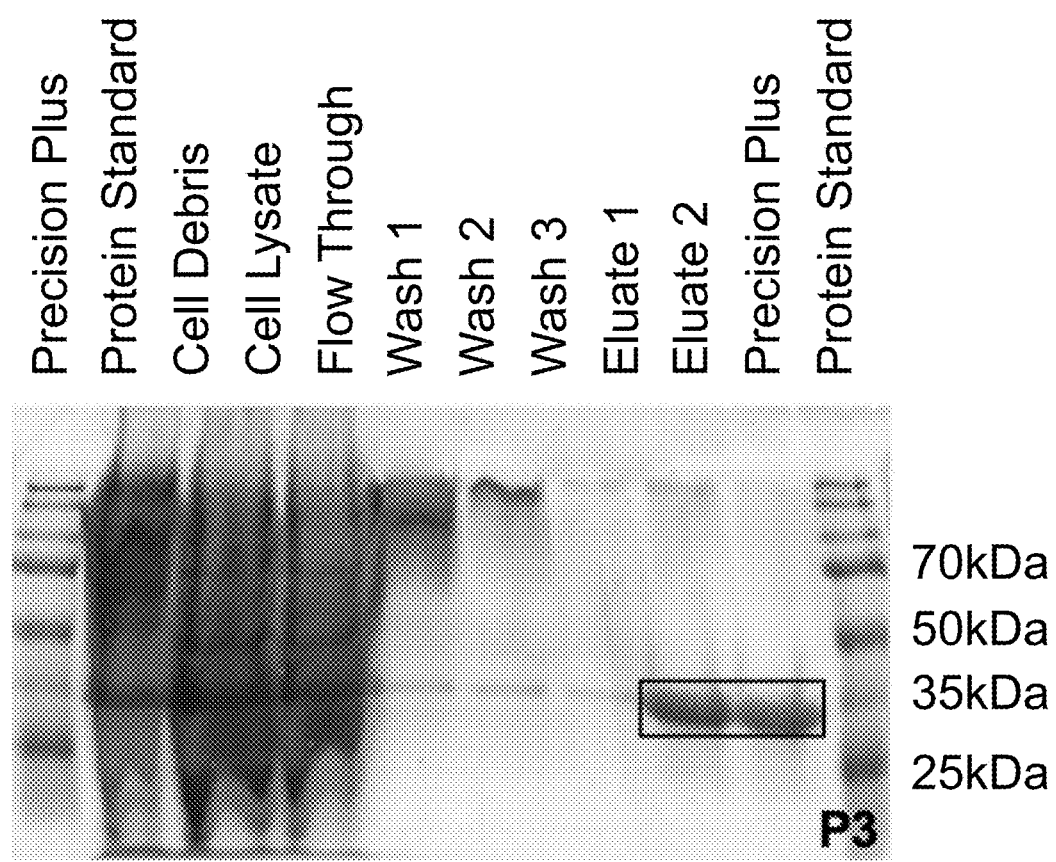
Figure 5A:
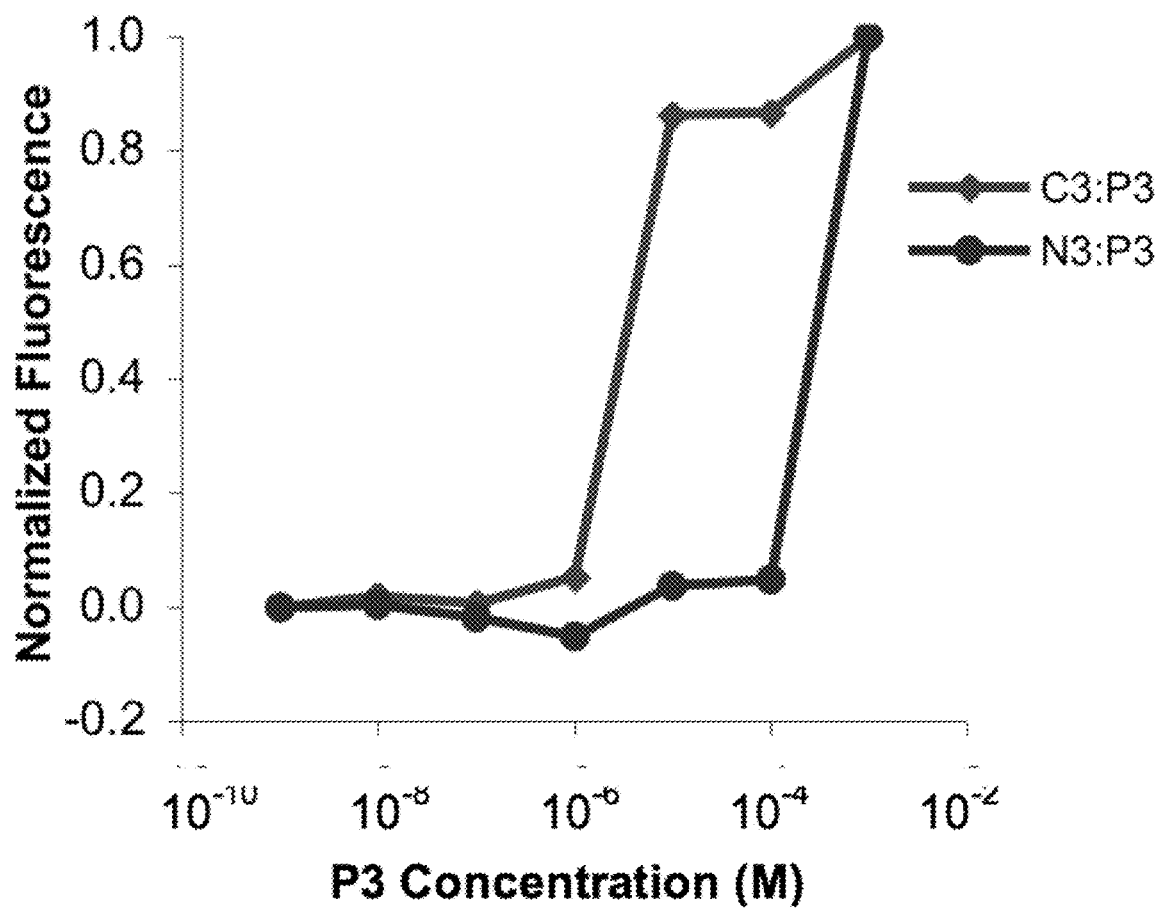
FIGS. 5A-C show examples of assays for binding affinity of engineered protein components according to an embodiment of the invention. Binding isotherms for Component 1 variants, C3 ($K_d$=4.6±0.01 μM) or N3 ($K_d$=62±4.6 μM) with Component 2 variant P3 assayed by (FIG. 5A) tryptophan fluorescence quenching and (FIG. 5B, FIG. 5C) by isothermal titration calorimetry. Linkage of the association domains by hydrophilic spacers does not prevent molecular recognition, and choice of WW domain can tune the association energy.
Figure 5B:
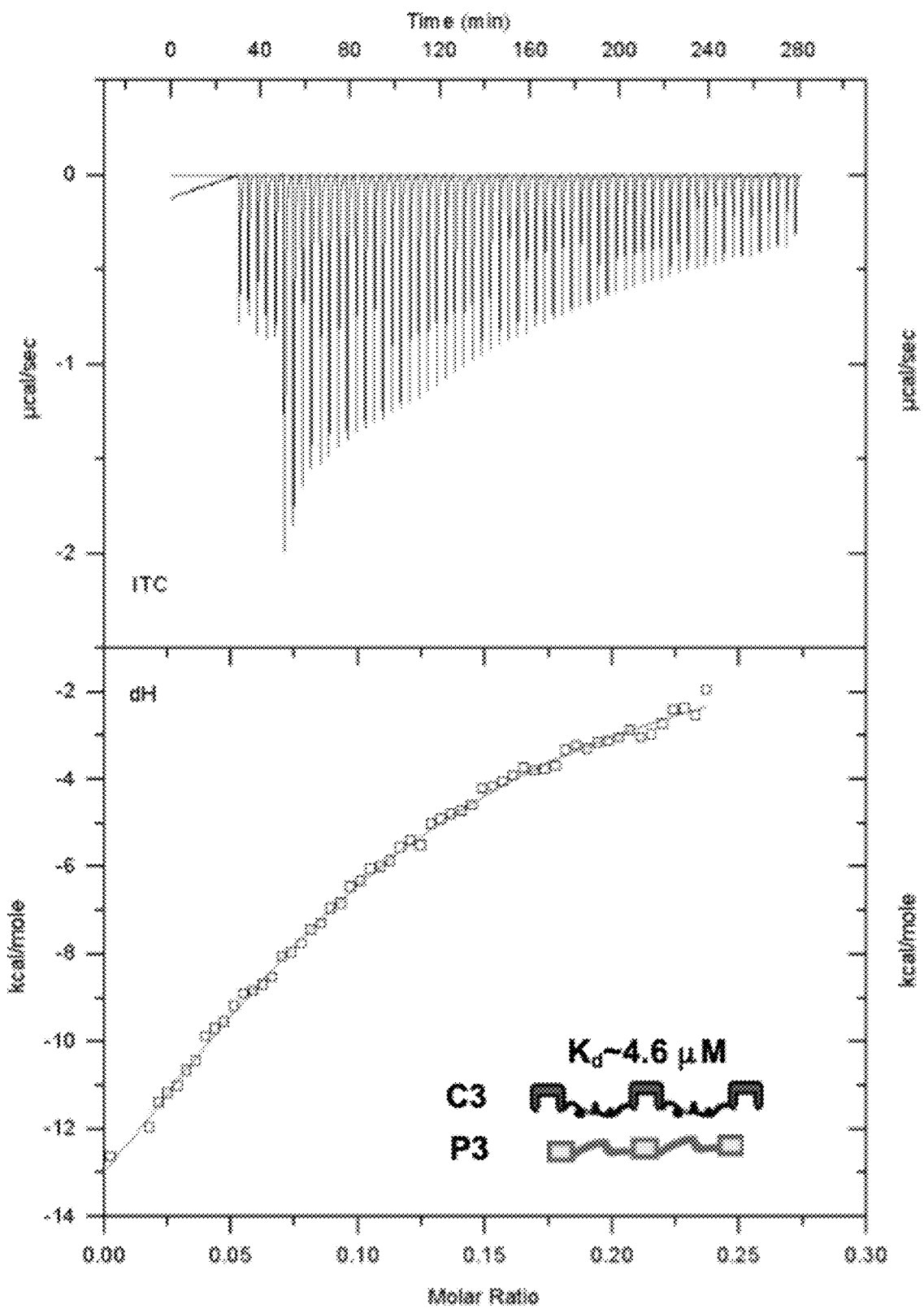
Figure 5C:
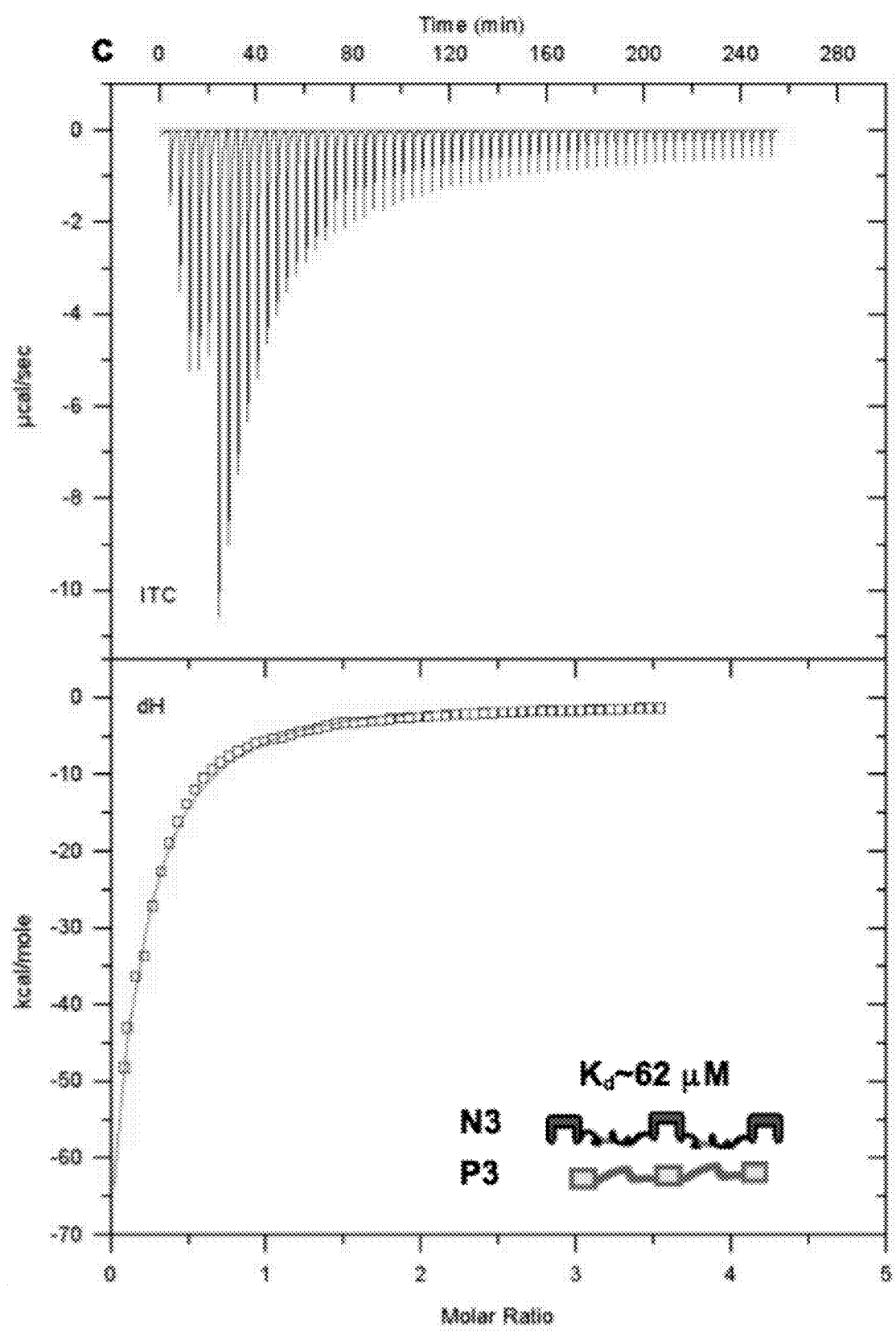

The synthesis of these precisely designed polymers was achieved using recombinant protein technology to encode each primary sequence in an exact modular genetic construct. The engineered proteins were successfully expressed in *Escherichia coli* and purified via affinity chromatography (FIGS. 4A-C). To verify that the association domains properly fold and bind when fused to hydrophilic spacers on their C- and N-termini, secondary structure and binding analyses were performed on protein-polymers with three repeats of each domain (C3, N3, and P3). Circular dichroism of C3 and N3 showed the characteristic features associated with the anti-parallel, triple-stranded β-sheet fold of a WW domain. Binding affinities were measured by isothermal titration calorimetry and tryptophan fluorescence quenching experiments (FIGS. 5A-C). P3 binds to C3 and N3 with apparent dissociation constants of $4.6 \pm 0.01$ μM and $62 \pm 4.6$ μM, respectively, consistent with previous observations of monomeric units of CC43 and Nedd4.3 bound to a model group I polyproline peptide (apparent dissociation constants of $1.7 \pm 0.1$ μM and $11.2 \pm 1.2$ μM, respectively) (FIGS. 5B-C). These assays demonstrate that the modular approach to protein engineering allows for the systematic design of families of proteins that physically bind through precise molecular-recognition interactions with tunable association energies.

While the three-peat polymers (C3, N3, and P3) did not form gels upon association, we argued that increasing the number of potential physical crosslinks per chain by synthesizing polymers with higher numbers of repeats (C7, N7, and P9) would result in the formation of bulk hydrogels. Simple mixing of a solution of C7 (6 wt %) with a solution of P9 (6 wt %) at constant physiological pH, temperature, and ionic strength leads to the formation of a viscoelastic hydrogel, C7:P9, as confirmed via particle tracking of micron-sized fluorospheres embedded within the hydrogel networks (FIG.

Figure 6A:
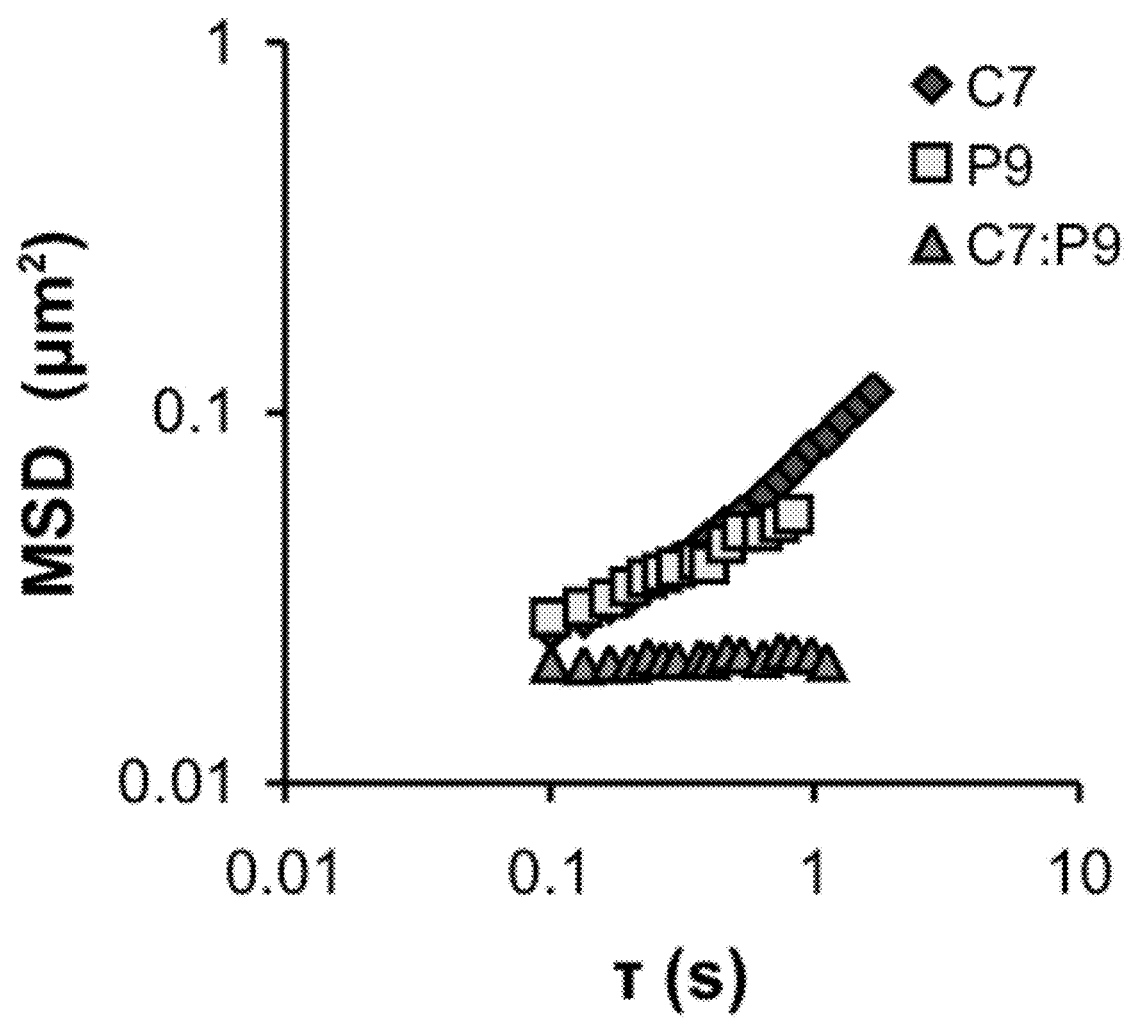
FIGS. 6A-C show examples of microrheological characterization of the two-component hydrogels according to an embodiment of the invention.
Figure 6B:
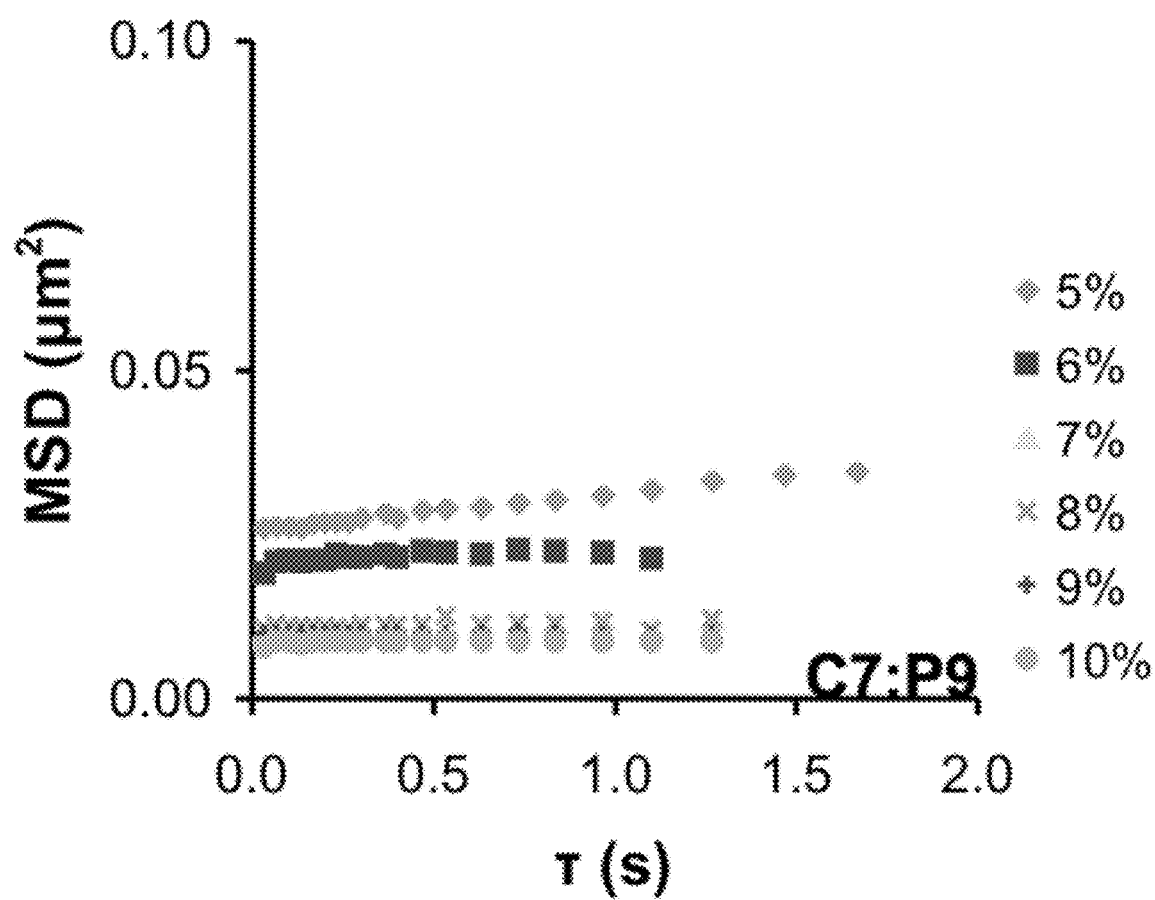
Figure 6C:
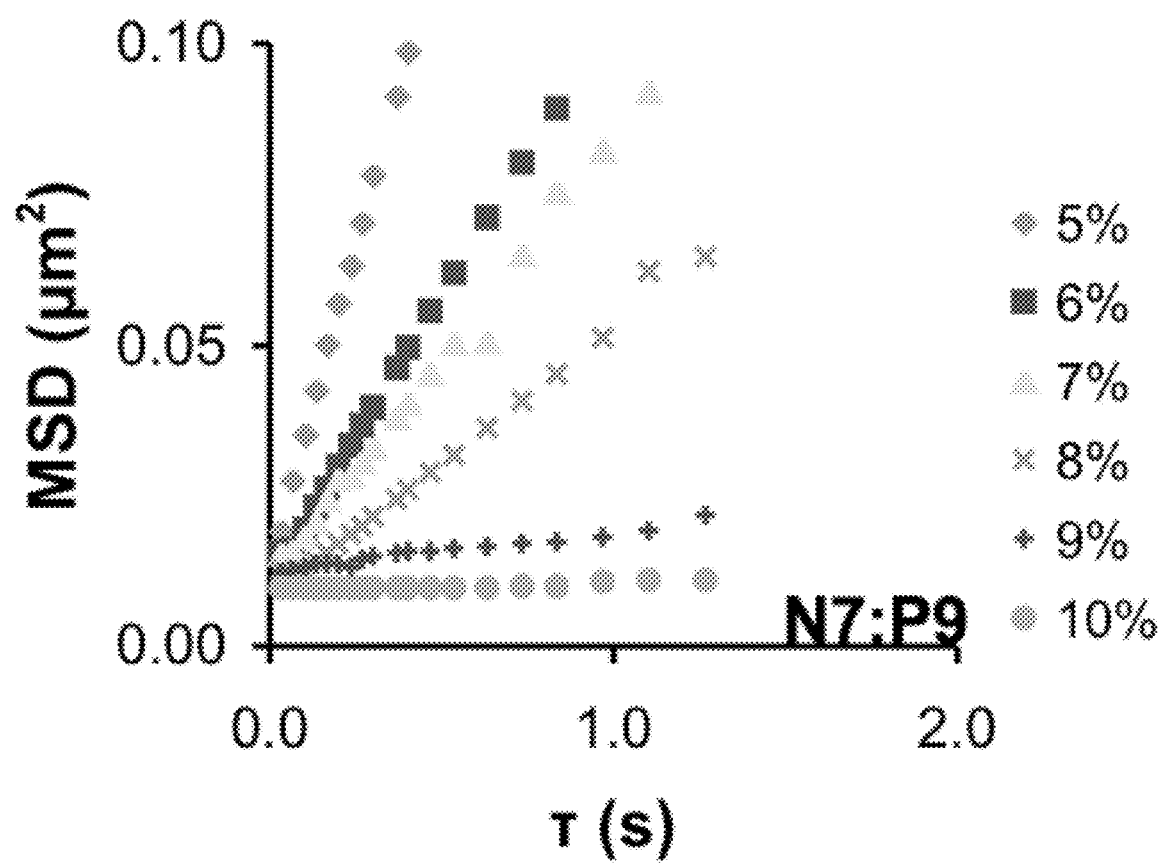

6A). The mean-squared displacement (MSD) of fluorospheres within solutions of the two individual components (C7 or P9) showed increased thermal displacement at longer time scales. This positive slope in MSD is indicative of freely flowing liquids. These results confirm the visual observation that solutions of C7 and P9 are freely flowing liquids when kept separate from one another (FIG. 6A). In contrast, fluorosphere displacement was found to be independent of time once the two components were mixed together, indicative of formation of a hydrogel network. As the weight percent of the solution was increased from 5 to 10%, the onset of gelation was significantly faster (data not shown, all gels formed within ~10 seconds) and the resulting hydrogels demonstrated greater bead confinement, consistent with stiffer gels (FIG. 6B). The ideal viscoelastic properties of hydrogels for cell transplantation applications are not yet well understood; however the gel should result in uniform cell suspensions and the properties may need to be optimized for specific cell types. It is now well documented that cell morphology, adhesion, differentiation, and gene expression are altered in response to biomechanical cues. Therefore, the ability to systematically tune the hydrogel viscoelastic properties is critical. Our modular design strategy would allow systematic control over the hydrogel viscoelasticity through selection and molecular-level arrangement of the individual association domains. As demonstrated, by substituting the C7 component with the weaker binding N7 component, the resulting hydrogels were significantly more compliant (FIGS. 6B-C). Therefore, a higher weight percent of N7:P9 (>8%) is required to form a gel compared to C7:P9 (5%) (FIGS. 6B-C). These results demonstrate that judicious selection of the molecular-level peptide building blocks can be used to predictably tune the macroscopic hydrogel viscoelastic properties.

Figure 7A:
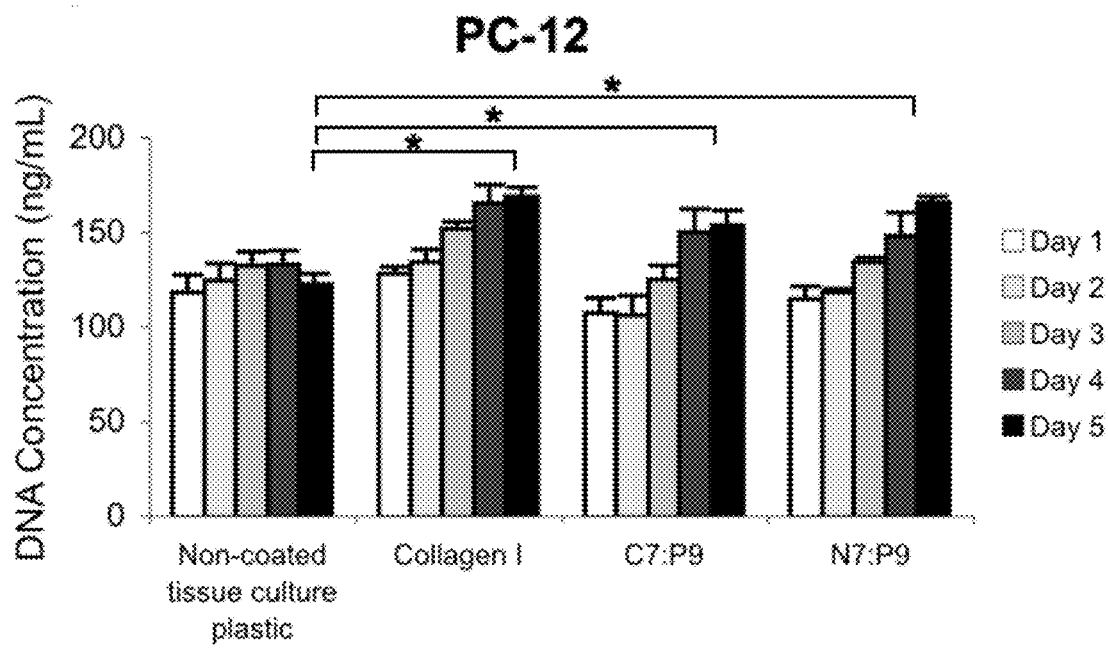
FIGS. 7A-B shows examples of PC-12 and adult NPC viability and differentiation on 2D films according to an embodiment of the invention.
Figure 7B:
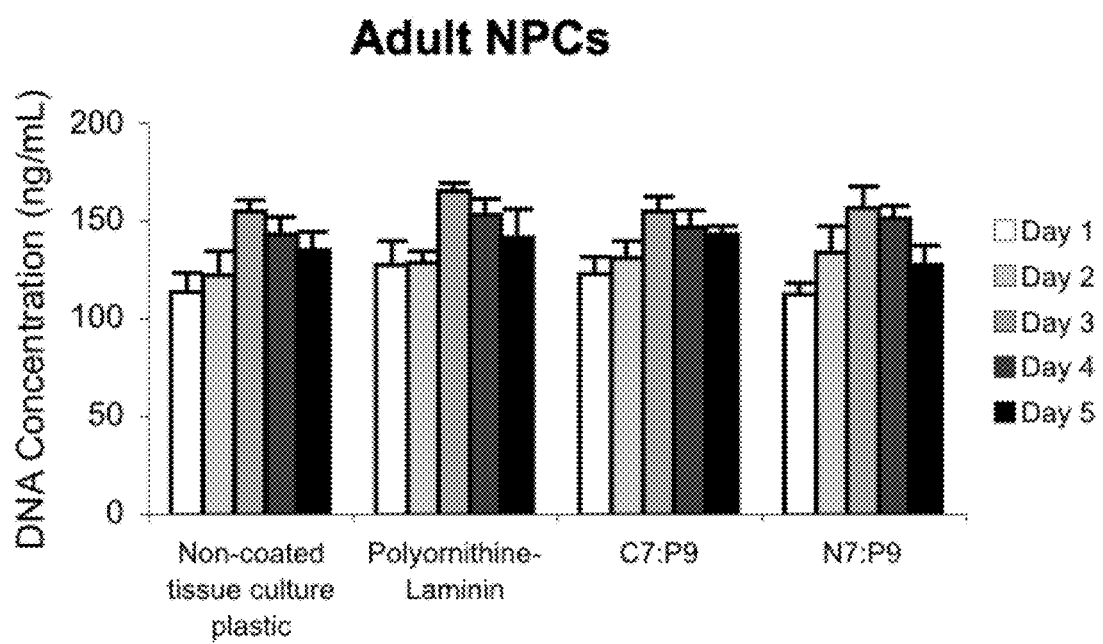

The bioactivity and biocompatibility of the physical hydrogels were initially assessed on 2D films of the C7:P9 and N7:P9 hydrogels using a neuronal-like PC-12 cell line and adult murine neural progenitor cells (NPC). Making use of the precision of protein engineering, we incorporated biofunctionality into the hydrogels by introducing a fibronectin-derived RGDS cell-adhesion sequence within hydrophilic spacer 1 (FIG. 2). PC-12 cell proliferation on C7:P9 and N7:P9 films, as monitored by DNA quantification, was found to be comparable to that on a positive control collagen I substrate and enhanced over non-coated tissue culture plastic, a common negative control material for adherent PC-12 cells (FIGS. 7A-B). For NPCs, which do not require substrate adhesion for viability, DNA quantification on all substrates was similar (FIGS. 7A-B). Additionally, NPCs grown on C7:P9 and N7:P9 hydrogel films were able to maintain their neural multipotency as observed via nestin-positive immunocytochemistry when cultured in proliferation medium. Cultures of both PC-12 and NPCs on C7:P9 and N7:P9 hydrogel films adopted typical neural morphologies after differentiation, with PC-12 cells showing long neuronal extensions and NPCs displaying glial (GFAP-positive) and neuronal (MAP2-positive) phenotypes.

Figure 8A:
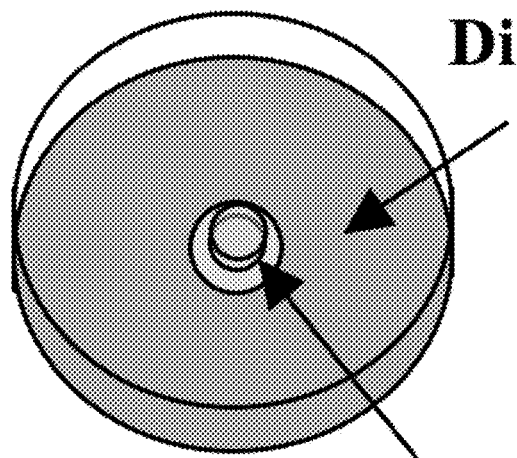
FIG. 8A-B show examples of a 3D cell encapsulation of adult NPC within hydrogel according of an embodiment of the invention (Schematic in FIG. 8A and Cell Image in FIG. 8B). 3D encapsulation of dissociated adult NPC was achieved by first mixing the cells (5×10$^6$ cells/ml) with the 10 μl solutions of 5% w/v C7 or N7 component before adding 10 μl of 5% w/v P9 component within a Teflon mold (Rainin Instrument, Oakland, Calif.) glued to the cover slip glass bottom of a 60-mm tissue culture plate (In Vitro Scientific, Sunnyvale, Calif.). The plate was then filled with either growth media or differentiation media.
Figure 8B:
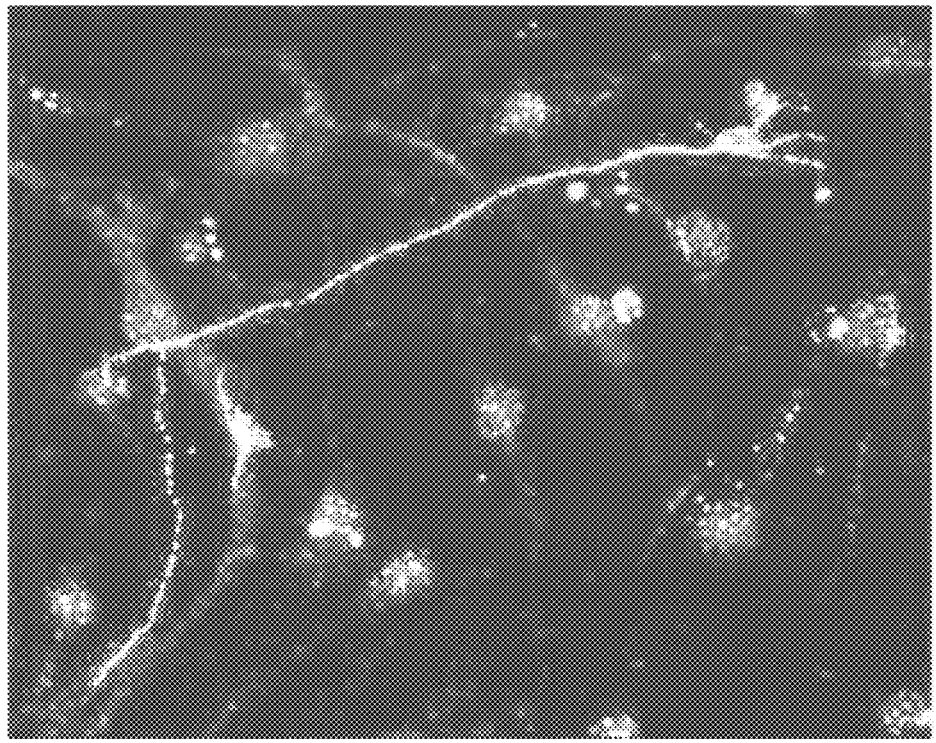

The two-component physical hydrogels presents the ability to encapsulate cells in 3D at constant physiological conditions. To demonstrate this, in one example, PC-12 and NPCs were pre-mixed with solutions of C7 or N7 prior to the addition of P9 to induce gelation (FIG. 8A-B). Confocal imaging of LIVE/DEAD stained samples showed high cell viability and uniform cell distribution five days after encapsulation, confirming the cytocompatibility of the encapsulation method of this invention and the lack of cytotoxicity of these physical hydrogels. Furthermore, the gelation mechanism based on specific molecular-recognition interactions for 3D encapsulation of cells, was unaffected by the presence of serum and other proteins such as growth factors, indicating that the other components present in the mixture did not interfere in the gelation process of our two-component system. This uniform cell distribution further confirms the fast gelation kinetics of our hydrogels, which form during mixing (<10 sec). These results are consistent with previous peptide assembly studies that reported decreasing the gelation time from 1 hour to 40 seconds resulted in homogeneous distributions of cells. Immunostaining of the 3D cultures of adult NPCs differentiated within C7:P9 and N7:P9 gels showed NPC differentiation into both neuronal and glial phenotypes, demonstrating that NPCs maintain their neural multipotency upon encapsulation and that scaffolds can support cell spreading, neurite outgrowth, and neurite branching.

These results clearly demonstrate a new strategy to easily encapsulate cells within injectable physical hydrogels. Gelation is based solely on the cumulative effects of specific molecular-recognition interactions between WW domains and polyproline-rich peptides repeated within the sequences of two distinct engineered components. The design of the individual components with spacers connecting multiple association domains was not observed to negatively affect the folding of the WW domains into the triple-stranded β-sheet conformation essential for interactions with polyproline-rich peptides. Through engineering of the molecular-level design, the number of repeating domains per chain and the dissociation constant between the two components were precisely altered. These design parameters at the molecular-level provide direct control of the macroscopic hydrogel viscoelastic properties. The two-component gelation strategy allows simple and gentle 3D cell encapsulation without compromising cell viability and without the use of any environmental triggers. In addition, the fast gelation kinetics observed allows for uniform cell distribution and makes our hydrogel an attractive candidate for cell transplantation in vivo. The hydrogel material was shown to be non-cytotoxic and capable of promoting cell proliferation, differentiation, and neurite extension.

The adult central nervous system (CNS), unlike many other tissues, has a limited capacity for self-repair, and endogenous neural stem cells are restricted in their ability to generate new functional neurons in response to injury or disease. A promising treatment for spinal cord injuries includes the transplantation of stem cell populations into the injured site to promote axonal and neural tissue regeneration. Both adult neural progenitor and embryonic stem cells have produced partial functional recovery in animal models with a wide spectrum of lesions, varying in severity and level of injury. However, cells are mostly injected in medium alone during transplantation and often result in low viability following implantation, e.g., up to 85% of the cells die during or shortly after the implantation procedure, and trial outcomes are often unpredictable. Cell viability is thought to be a critical component of successful cell transplantation therapy and has been shown to directly correlate to functional outcome. Therefore, there is a strong need to develop new efficient methods of delivery of transplanted cells to the lesioned or diseased tissue of the central nervous system. We argue that this two-component system may substantially enhance neuronal cell survival during direct cell injection.

The precision of protein engineering allows both components to be easily modified to incorporate other selective cell-binding domains into the hydrophilic spacers to target the growth of specific cell types as well as the release of specific growth factors and is currently under way. This biosynthetic strategy further enables exact molecular-level design of the repeating polymers, which will provide insights into the relationship between network structure and macroscopic hydrogel properties. This new approach to forming a physical hydrogel that facilitates cell encapsulation under normal physiological conditions without the use of external environmental triggers will enhance cell viability, be easily transferred to surgical procedures, and contribute to the success of cell transplantation therapies.

Materials and Methods

Protein Engineering

WW domain block copolymers (N3-7 and C3-7) and polyproline peptide chains (P3-9) were cloned into the pET-15b vector (Novagen, San Diego, Calif.), expressed in BL21 (DE3) *Escherichia coli* host strain (Novagen), and purified via specific binding of an N-terminal His-Tag sequence to Ni-NTA resin (Qiagen, Valencia, Calif.).

Binding Assays

Tryptophan fluorescence-based peptide binding assays were conducted on a SpectraMax Gemini EM spectrofluorometer (Molecular Devices, Sunnyvale, Calif.), monitoring the intrinsic fluorescence emission of the tryptophan residues at 340 nm (excitation at 295 nm). Binding assays for 1 μM C3 and N3 were conducted in triplicate at 25° C. in buffer TN (100 mM TrisHCL, 100 mM NaCl, pH 8.0) with $10^{-9}$ to $10^{-3}$ M P3.

Isothermal titration calorimetry measurements were made using a MicroCal VP-ITC microcalorimeter (Microcal, Inc., Northhampton, Mass.) in buffer TN at 25° C., starting with 150 μM C3 or N3 recombinant proteins in the sample cell and titrating 1.5 to 2.2 mM P3, sixty-three injections. Data were fitted using a one-site binding model with MicroCal Origin software.

Particle Tracking

Microrheology particle tracking experiments were performed using 0.2 micron-sized tracer fluorescent particles (Molecular Probes, Carlsbad, Calif.) added to 10 μl solutions of 10 to 5% w/v C7, 10 to 5% w/v N7, and 10 to 5% w/v P9 in buffer TN. 10 μl samples were pipetted between a microscope slide and a cover slip separated by a 120 μm thick SecureSeal Imaging Spacer (Grace Biolabs, Bend, Oreg.). Particle tracking was conducted using a Zeiss microscope equipped with an ANDOR iXON DV897 camera (ANDOR Technology, South Windsor, Conn.). The Brownian dynamics of 20-50 embedded beads were followed simultaneously under a 40× oil objective with a temporal resolution of ~30 Hz for ~15 seconds. Stacks of tiff images were analyzed following the methods and macros developed by Crocker and Grier (27) (1996) using IDL software version 7.0.

Cell Culture and Differentiation

PC-12 cells were cultured on BD Primaria tissue culture plastic dishes using F-12 Kaighn's modified media with L-glutamine, containing 10% heat-inactivated horse serum, 5% fetal bovine serum, and 100 U/ml, 100 μg/ml penicillin-streptomycin (P/S) solution. For differentiation, cells were seeded at a density of $1\times10^4$ cells/cm$^2$ and primed for 1 day in PC-12 culture media before differentiating for 7 days in F-12K media containing 100 U/ml, 100 μg/ml P/S solution and 50 ng/ml recombinant human beta nerve growth factor (R&D Systems, Minneapolis, Minn.).

Murine adult neural progenitor cells (NPC) were isolated as previously described and cultured as neurospheres in tissue culture plastic flasks using Neurobasal-A media supplemented with 1% glutamax, 2% B27 vitamin, 20 ng/ml epidermal growth factor (EGF) and 20 ng/ml fibroblast growth factor (FGF). For differentiation, cells were seeded at a density of $1\times10^4$ cells/cm$^2$ and primed for 1 day in adult NPC growth media before changing to differentiation medium (low FGF concentration—5 ng/ml) for 2 days and finally, replacing with Neurobasal-A media supplemented with 1% glutamax and 2% B27 vitamin only for 3 days. Adult NPC were cultured as a single cell monolayer in polyornithine-laminin coated tissue culture plastic flasks.

Cell Proliferation Assay

PC-12 and adult NPC cell proliferation on various substrates (tissue culture plastic, collagen I, polyornithine-laminin, C7:P9 films, and N7:P9 films) was assessed by total DNA quantification using the PicoGreen assay (Molecular Probes, Carlsbad, Calif.). Cells were seeded in quadruplicate at $1\times10^4$ cells/cm$^2$ on the different substrates cast into the wells of 24-well plates and incubated at 37° C. and 5% CO$_2$. After 1 to 5 days, the media in each well was removed and the cells disrupted by adding 1 ml of lysis buffer (0.2% Triton-X and 5 mM MgCl$_2$) to each well and incubating in the dark for 48 h. The lysates were centrifuged at 3000 g and RT for 10 min. The supernatant was mixed with diluted PicoGreen solution (PicoGreen dimethylsulfoxide stock solution diluted 200× in TE assay buffer) according to the manufacturer's protocol. After thorough mixing, 100 μl of the solution was transferred to a 96-well assay plate and fluorescence measurements were taken at $\lambda_{ex}$ and $\lambda_{em}$ of 480 and 528 nm, respectively, using a SpectraMax M2 Spectrophotometer (Molecular Devices, Sunnyvale, Calif.). Statistical analysis was performed using SPSS Statistics v16.0 software (Chicago, Ill.). One-way analysis of variance (ANOVA) was performed followed by Tukey post-test and statistically significant differences with $p<0.05$, $p<0.01$ and $p<0.001$ were noted (only statistically significant differences with $p<0.001$ are shown on the bar graphs).

Cell Encapsulation 3D encapsulation of PC-12, adult NPC neurospheres, and dissociated adult NPC was achieved by first mixing the cells ($5\times10^6$ cells/ml) with the 10 μl solutions of 5% w/v C7 or N7 component before adding 10 μl of 5% w/v P9 component within a Teflon mold (Rainin Instrument, Oakland, Calif.) glued to the cover slip glass bottom of a 60-mm tissue culture plate (In Vitro Scientific, Sunnyvale, Calif.). The plate was then filled with either growth media or differentiation media.

LIVE/DEAD Assay

Cell viability within hydrogels was assessed with a LIVE/DEAD kit, a fluorescence-based membrane integrity assay (Molecular Probes, Carlsbad, Calif.). PC-12 cells and mouse adult NPC neurospheres encapsulated within hydrogels, were cultured for 5 days in growth media before incubating in PBS containing 1.0 μM calcein-AM and 2.0 μM ethidium homodimer for 30 to 45 min and were directly visualized by laser confocal microscopy. All images were captured using a Leica Laser Scanning Microscope equipped with an Axiovert microscope, 40× oil immersion objective (Zeiss Achroplan 10, numerical aperture 0.3, working distance 3.1 mm).

Immunocytochemical Staining

Cultures were fixed in 4% paraformaldehyde in 0.1 M phosphate buffer (PBS, pH 7.4) for 15-30 minutes. After washes with PBS, cells were blocked with 10% normal goat serum (Invitrogen, Carlsbad, Calif.) containing 0.1% v/v Triton X-100 in phosphate-buffered saline (PBST). Primary antibodies were diluted in 0.1% PBST solution containing 5% normal goat serum and incubated overnight. After washes with 0.1% PBST, secondary antibodies were diluted in 0.1% PBST and the cells were incubated for 2 h at room temperature.

The following primary antibodies and dilutions were used: rabbit anti-neuronal class III 1-tubulin (TuJ1) 1:500 (Covance, Berkeley, Calif.); mouse anti-nestin 1:500 (BD Pharmingen, San Jose, Calif.); rabbit anti-microtubule-associated protein 2 (MAP2) 1:1000 (Chemicon, Temecula, Calif.); guinea pig anti-GFAP 1:300 (Advanced Immunochemicals, Long Beach, Calif.). Fluorescently coupled secondary antibodies were raised in goat (Alexafluor® 488, 546 and 633 and used at 1:500. DAPI was used as a nuclear counterstain (Roche, Indianapolis, Ind.). A Zeiss Axiovert 200M fluorescence microscope with a 40× oil objective (Carl Zeiss Microimaging, Thornwood, N.Y.) and a Leica TCS/SP2 confocal microscope (Leica, Bensheim) were used to evaluate fluorescent stainings.

ALTERNATE EMBODIMENTS

In an alternate embodiment, the present invention pertains to the design of a polymer-protein two-component hydrogel system that is highly tunable and injectable for the encapsulation and delivery of growth factors, peptides, drugs and cells.

For FIGS. 9-16, Component 1 in the alternate embodiment is identical to one embodiment of Component 1 described in FIG. 2. For FIGS. 17-25, Component 2 in the alternate embodiment is identical to one embodiment of Component 1 described in FIG. 2.

Hydrogels are space-filling materials composed of more than 90% water. Their unique structure makes them easily injectable (either pre- or post-gelation) and promotes maximum diffusion of biomolecules throughout the scaffold, two important criteria for cell encapsulation for both primary cell biology studies as well as cell transplantation for regenerative medicine.

In the earlier embodiments, described supra, we discussed a Mixing-Induced Two-Component Hydrogel (MITCH) system, which can encapsulate cells simply by mixing two components together at physiological conditions without needing any external triggers, such as chemical crosslinkers, ultraviolet irradiation, or sudden shifts in pH, ionic strength, or temperature.

To further develop the hydrogel properties, we provide herein two designs to our MITCH: MITCH-PEG and MITCH-PEG-PNIPAM. MITCH-PEG is identical in its ability to enhance cell viability for cell encapsulation, and has as one of its components a multi-armed polyethylene glycol (PEG) polymer, which is FDA-approved for use in medical implants. MITCH-PEG offers better tunability of hydrogel mesh size, viscosity, and shear thinning properties, which are highly pertinent to the mechanical protection of cells during injection. MITCH-PEG-PNIPAM further enhances mechanical properties of the hydrogels by forming a secondary poly (N-isopropylacrylamide) (PNIPAM) network, which can also sequester growth factors and increase material retention time.

In one embodiment, the MITCH-PEG hydrogel system includes a single, linear, engineered protein (termed C7) and an 8-arm, peptide-modified PEG. The C7 protein is the same as a component from the original MITCH and expressed using recombinant protein engineering technology. The C7 protein contains seven repeats of a computationally derived WW domain interspersed with a hydrophilic, random coil peptide sequence. PEG is a highly hydrophilic, FDA-approved polymer that is readily decorated with peptides via covalent bioconjugation. An 8-arm PEG was reacted with either a single proline-rich peptide (termed P1) or a double repeat of the proline-rich peptide (P2). Isothermal titration calorimetry confirmed that the P1 and P2 domains both bind to only a single C domain at a given time. The P2 domain should have a higher effective binding strength compared to the P1 domain due to avidity. A Michael-type addition was chosen to bioconjugate the P1 or P2 peptides onto vinyl sulfone-terminated, 8-arm PEG (PEG-VS). Reaction of cysteine-terminated P1 or P2 peptides with either 20 kDa or 40 kDa 8-arm PEG-VS generated four variants of 8-arm-PEG-peptide conjugates. Therefore, mixing of C7 with these four formulations creates four MITCH-PEG hydrogel variants with tunable material properties. All four PEG variants were able to undergo a sol-gel phase transition when mixed with the linear C7 protein at constant physiological conditions due to noncovalent hetero-dimerization between the C and P domains. Due to the dynamic nature of the C-P physical crosslinks, all four gels were observed to be reversibly shear-thinning and self-healing. The P2 variants exhibited higher storage moduli than the P1 variants. The 20 kDa PEG variants exhibited slower release of encapsulated vascular endothelial growth factor (VEGF), due to a decrease in hydrogel mesh size relative to the 40 kDa variants. Human induced pluripotent stem cell-derived endothelial cells (hiPSC-ECs) adopted a well-spread morphology within three-dimensional MITCH-PEG cultures, and MITCH-PEG provided significant protection from cell damage during ejection through a fine-gauge syringe needle. We have evaluated the in vivo biocompatibility of the hydrogel in a mouse model, with excellent inflammation scores (i.e., negligible inflammation).

In another embodiment, the MITCH-PEG-PNIPAM hydrogel system is composed of the C7 protein and the 8-arm PEG with seven arms conjugated with P1 and one arm conjugated with PNIPAM. To further enhance the hydrogel mechanical properties, the MITCH-PEG-PNIPAM hydrogel is designed to undergo two different physical crosslinking mechanisms to form a dual network hydrogel that improves cell viability during transplantation. The first crosslinking step occurs through peptide-based molecular recognition between C and P domains, while the second crosslinking step occurs at body temperature through a thermal phase transition to form a reinforcing PNIPAM network. At room temperature, the MITCH-PEG-PNIPAM physical hydrogel is shear-thinning and self-healing to facilitate gentle cell encapsulation and transplantation by syringe injection. At body temperature, the hydrogel forms a secondary network resulting in a 10-fold increase in shear modulus. Human adipose-derived stromal cells (hASCs) exposed to hand-injection through a 28-gauge syringe needle were significantly protected from disruptive mechanical forces when encapsulated within the hydrogel compared to injection of cells in saline alone (93±4% vs. 69±5% cell viability, respectively).

Advantages

The hetero-assembled MITCH-PEG hydrogel and the dual network MITCH-PEG-PNIPAM hydrogel have various advantages over the MITCH hydrogel.

First, using the multi-arm PEG component instead of the original P9 protein offers greater tunability over hydrogel properties by varying PEG molecular weight. The hydrogel mesh size can be tuned to control its mechanical properties and the release rate of encapsulated drugs or growth factors. The multi-arm PEG architecture also allows for better spatial distribution of the conjugated prolich-rich peptide compared to the linear P9 protein, thereby facilitating C-P hetero-assembly.

Second, by conjugating P1 or P2 variants to the PEG, the hydrogel properties can be tuned via biomimetic avidity, which is the combined enhancement of multiple weak affinity interactions. The avidity effect can enhance the hydrogel stiffness and decrease the diffusivity of drug molecules, thereby slowing their release kinetics.

Third, the PNIPAM segment induces formation of a secondary network that increases mechanical properties, sequesters growth factors, and slows down hydrogel erosion rates.

These advantages could improve long-term cell protection and retention at body temperature. As with the original MITCH formulation, these two hydrogel systems can encapsulate cells, drugs, and proteins at constant physiological conditions with highly tunable material properties to meet various tissue-engineering requirements.

Variations

Using common recombinant protein engineering techniques, the parameters of the scaffold can be tuned to create a family of hydrogels with tailored properties. This strategy of choosing two distinct, hetero-assembling peptide binding partners to induce physical gelation of a hydrogel at physiological conditions should be widely applicable to other peptide binding partners beyond the WW domain and polyproline peptide. The multi-arm PEG component can be varied to have a different number of arms and varying arm lengths that determine the hydrogel mesh size after hetero-assembly. The PEG component can be replaced by other hydrophilic polymers including polypeptides and polysaccharides such as the biopolymer alginate. The avidity effect can be further exploited by using more repeats of the P1 peptide (i.e., P3, P4, etc.) to further increase the effective binding affinity. Moreover, the molecular weight of the PNIPAM segment can be varied to control the hydrogel stiffness. Other types of thermo-responsive molecules such as elastin-like polypeptides can be used to replace the PNIPAM chains.

The properties of these hydrogel systems can also be tailored for a variety of in vitro and in vivo applications. Examples of in vivo target applications are: 1) cell transplantation to spinal cord defects for the treatment of spinal cord injury and 2) cell transplantation to ischemic muscle tissue for the treatment of peripheral arterial disease. Examples of in vitro target applications are: 1) the 3D culture of stem cells to guide differentiation, 2) the 3D culture of human cells to create tissue arrays for drug screening, and 3) use as a cell-compatible bio-ink for 3D printing.

Another variation is to use the material to encapsulate and deliver protein therapeutics with a pre-determined release rate. Currently, high concentrations of growth factors need to be supplemented to cell culture media during cell transplantation in animal models to account for their diffusion and degradation due to exposure to proteases. Incorporating growth factors into our hydrogel will not only enhance differentiation of the encapsulated cells, but will also provide a slow release of growth factors to the surrounding tissue. Protein diffusion is directly related to hydrogel mesh size, which can be systematically tuned and customized in our system. Therefore, the material may also find use as a delivery vehicle for growth factors, peptides and drugs that require specific release kinetics.

Applications

Embodiments of the invention can be of interest to:

Suppliers of biology laboratories as a research tool for in vitro cell culture studies.

Biomedical companies developing materials for wound healing and regenerative medicine as either a cell or biomolecule delivery vehicle.

Biomedical companies developing stem cells and progenitor cells for transplantation therapies. For example, cell transplantation shows great potential as a means to restore function to ischemic brain tissue following stroke; however, cell viability of the transplanted cells is often quite low (15-35%). This low cell viability has been directly correlated to the ultimate success of the procedure to restore functionality. We predict our material will both improve cell viability during the transplantation procedure by supplying the transplanted cells with protection from mechanical stress and by providing an instructive environment for the cells that mimics the naturally occurring extracellular matrix once implanted.

Companies producing transdermal drug delivery systems, as this hetero-assembling system is capable of encapsulating proteins and/or drugs at constant physiological conditions.

Companies involved in additive manufacturing or 3D printing of biological constructs with or without cells.

Companies developing in vitro platforms for high throughput screening of human tissue and cells. For example, this could include 3D cultures of cancerous tissue for drug screening.

DETAILED DESCRIPTION OF ALTERNATE EMBODIMENTS

1. Avidity-Controlled Hydrogels for Injectable Co-Delivery of Induced Pluripotent Stem Cell-Derived Endothelial Cells and Growth Factors Summary Building on our previous invention (e.g. U.S. patent application Ser. No. 12/455,996 filed on Jun. 9, 2009, now U.S. Pat. No. 9,011,914) designing Mixing-Induced Two-Component Hydrogels (MITCH) from engineered proteins, here we describe protein-polyethylene glycol (PEG) hybrid hydrogels, MITCH-PEG, which form physical gels upon mixing for cell and growth factor co-delivery.

MITCH-PEG is a mixture of C7, which is a linear, engineered protein containing seven repeats of the CC43 WW peptide domain (C), and 8-arm star-shaped PEG conjugated with either one or two repeats of a proline-rich peptide to each arm (P1 or P2, respectively). Both 20 kDa and 40 kDa star-shaped PEG were investigated, and all four PEG variants were able to undergo a sol-gel phase transition when mixed with the linear C7 protein at constant physiological conditions due to noncovalent hetero-dimerization between the C and P domains. Due to the dynamic nature of the C-P physical crosslinks, all four gels were observed to be reversibly shear-thinning and self-healing. The P2 variants exhibited higher storage moduli than the P1 variants, demonstrating the ability to tune the hydrogel bulk properties through a biomimetic peptide-avidity strategy. The 20 kDa PEG variants exhibited slower release of encapsulated vascular endothelial growth factor (VEGF), due to a decrease in hydrogel mesh size relative to the 40 kDa variants. Human induced pluripotent stem cell-derived endothelial cells (hiPSC-ECs) adopted a well-spread morphology within three-dimensional MITCH-PEG cultures, and MITCH-PEG provided significant protection from cell damage during ejection through a fine-gauge syringe needle.

In an animal hindlimb ischemia model of peripheral arterial disease, MITCH-PEG co-delivery of hiPSC-ECs and VEGF was found to reduce inflammation and promote muscle tissue regeneration compared to a saline control.

1. Introduction

We introduce a new family of injectable hydrogels formed through the dynamic hetero-assembly of a linear, engineered protein with a star-shaped, peptide-modified PEG molecule that takes advantage of biomimetic avidity to fine-tune the hydrogel properties. Following the first report of Mixing- Induced Two-Component Hydrogels (MITCH), which were composed entirely of linear, engineered proteins,[1] the strategy was expanded by several groups to demonstrate the successful mixing-induced gelation of star-shaped, peptide-modified PEG molecules using a variety of peptide binding domains.[2-6] In all of these systems, gelation is induced by noncovalent peptide hetero-assembly when the individual hydrogel components are mixed together. Because the mechanical properties of MITCH systems are directly related to the concentration and binding affinity of the hetero-assembled crosslinks,[1, 7] we hypothesized that presenting dimers of binding ligands in close proximity would result in a dramatic lowering of the apparent equilibrium dissociation constant, $K_{d,app}$, and hence increase the number of hetero-assembled crosslinks. This gelation mechanism mimics the evolved strategy of avidity, i.e. the combined enhancement of multiple weak affinity interactions. At a molecular level, avidity can be mechanistically explained by considering the dynamic, noncovalent binding of a single protein receptor to a single ligand within a larger array of ligands. Although the protein receptor will bind and unbind the ligand with the kinetic rate constants, $k_{on}$ and $k_{off}$, the likelihood of the unbound receptor quickly finding another ligand to rebind will increase as the ligand density increases. Therefore, the apparent $k_{on}$, also increases with ligand density, effectively lowering the apparent equilibrium dissociation constant. As a result, multiple weak binding interactions can appear to have a much higher effective binding energy. While this avidity-based, multivalent strategy has been applied in the field of nanobiotechnology for drug delivery, bioimaging, and biosensing applications,[8-10] it has yet to be explored in peptide hetero-assembled hydrogels.

We further believed that these avidity-controlled MITCH systems would be tunable carriers for the co-delivery of induced pluripotent stem cell-derived endothelial cells and growth factors. Human-induced pluripotent stem cell-derived endothelial cells (hiPSC-ECs) are ideal candidates for vascular therapy. Reprogrammed from somatic cells, iPSCs offer an abundant source of autologous cells that mitigate immunogenicity and ethical concerns.[11] In a murine hindlimb ischemia model for peripheral arterial disease, hiPSC-ECs injected into the ischemic calf muscle enhanced microvessel density and improved blood reperfusion by secreting angiogenic cytokines and incorporating into expanding endogenous microvasculature.[12] The clinical adoption of hiPSC-EC therapy is currently hampered by the rapid decline of transplanted cell viability, which necessitates multiple cell administrations for sustaining therapeutic efficacy.[12] Acutely, the number of viable cells plummets during injection due to membrane-disruptive extensional forces experienced in the syringe needle.[13] Pre-encapsulation of cells within a shear-thinning, self-healing physical hydrogel can provide significant protection from these mechanical forces;[13-15] therefore, we hypothesized that avidity-controlled MITCH systems may provide a similar protective effect.

Without the aid of a biomaterial carrier, efforts to enhance transplanted cell survival typically involve donor cell supplementation with biochemical factors that block apoptotic pathways associated with hypoxia and inflammatory insult.[16, 17] Vascular endothelial growth factor (VEGF) is a promising drug for co-delivery with hiPSC-ECs into ischemic target tissues, since VEGF is known to promote endothelial cell proliferation, survival and migration. In addition to enhancing donor cell survival, VEGF is a potent pro-angiogenic signal that could augment hiPSC-EC paracrine signaling and improve blood reperfusion by coaxing endogenous revascularization. Similar to many soluble pro-survival factors,[18] VEGF has a short in vivo circulating half-life (three minutes in mice).[19] Moreover, bolus delivery of VEGF results in a rapid dosage burst that produces leaky and aberrant vessels and off-target effects [20] instead of mature and stable vasculature. In a murine hindlimb ischemia model, optimal revascularization was achieved by a profile of high initial VEGF dosage, followed by steadily decreasing concentration over time.[20] Temporal regulation therefore underpins the safety and efficacy of cell and VEGF combinatorial therapy.

To demonstrate the suitability of our developed avidity-controlled MITCH system for co-delivery of hiPSC-ECs and VEGF, we synthesized and characterized a family of four hydrogels with tunable viscoelastic and diffusive properties. We further evaluated the lead formulation in a preclinical murine hindlimb ischemia model of peripheral arterial disease. To the best of our knowledge, this work represents the first demonstration of avidity-controlled, injectable hydrogels for applications in regenerative cell and drug combination therapy.

2. Materials and Methods

2.1. Synthesis and Purification of C7 Protein

The C7 recombinant protein polymer (see FIG. 9 for full amino acid sequence) was cloned, synthesized, and purified. [1] In brief, the DNA sequence encoding the C7 block copolymer was cloned into the pET-15b vector (Novagen) and transformed into the BL21(DE3)pLysS *Escherichia coli* host strain (Life Technologies). Protein was expressed following isopropyl β-D-1-thiogalactopyranoside (IPTG) induction, purified by affinity chromatography via the specific binding of N-terminal polyhistidine tag to Ni-nitrilotriacetic acid resin (Qiagen), buffer exchanged into phosphate-buffered saline (PBS), and concentrated by diafiltration across Amicon Ultracel filter units (Millipore) with 30 kDa Molecular Weight Cut-Off (MWCO). Protein identity and purity were confirmed by gel electrophoresis, MALDI-TOF mass spectrometry, and amino acid compositional analysis (data not shown).

C7 protein used in in vivo experiments was further subjected to lipopolysaccharide (LPS) removal by four cycles of phase separation and temperature transition extraction with Triton X-114. Residual Triton X-114 was removed by overnight incubation with Bio-Beads SM-2 Adsorbents (Biorad), and the PyroGene Recombinant Factor C Endotoxin Detection Assay kit (Lonza) was used to confirm the reduction of LPS levels to below 5 EU/mg in the final C7 protein solutions.

2.2. Conjugation of P1 and P2 Peptides to 8-Arm PEG 8-arm polyethylene glycol vinyl sulfone (8-arm-PEG-VS) with nominal molecular weights of 20 and 40 kDa were purchased from Nanocs (Boston, Mass.). Peptides P1 (EYP-PYPPPPYPSGC, 1563 Da) and P2 (EYPPYPPP-PYPSGGGGGEYPPYPPPPYPSGC, 3234 Da) were purchased through custom peptide synthesis from Genscript Corp (Piscataway, N.J., USA) and confirmed to have purity of 92-98% by HPLC. All other chemicals were purchased from Sigma-Aldrich (Milwaukee, Wis.) unless otherwise noted. A Michael-type addition of P1 or P2 to 8-arm-PEG-VS was conducted in a Schlenk tube in the presence of tris(2-carboxyethyl)phosphine (TCEP). Peptides (P1 or P2), 8-arm-PEG-VS (20 kDa or 40 kDa), and TCEP were dissolved at a molar ratio of thio:VS:TCEP=1.5:1:0.05 in 0.3 M triethanolamine (TEA) solution and pH was adjusted to 8.0. The reaction solution was then degassed, flushed with nitrogen, and maintained in a 37° C. incubator for 24 h. The solution was then lyophilized and washed with chloroform to remove unreacted PEG. The precipitate was redissolved and dialyzed into deionized water, using 10 kD MWCO dialysis tubing. A second lyophilization step yielded the final 8-arm-PEG-peptide conjugate products as white powder, with overall conjugation efficiency of ~80%.

The chemical structures of the purified 8-arm-PEG-peptide conjugates were confirmed by $^1$H Nuclear Magnetic Resonance (NMR) spectrometry, acquired on a Varian Inova 500 MHz NMR spectrometer. Deuterium oxide containing a trace amount of 4,4-dimethyl-4-silapentane-1-sulfonic acid (DSS) (Cambridge Isotope Laboratories, Andover, Mass.) was used as a solvent. Peptide conjugation efficiency was quantified from the ratio of area under the tyrosine doublets to the peak area corresponding to the PEG backbone. Compositional purity was characterized by polyacrylamide gel electrophoresis (PAGE) under non-denaturing conditions. Bands were visualized by staining with Commassie brilliant blue dye.

2.3. Isothermal Titration Calorimetry (ITC)

The differential binding affinity of P1 and P2 peptides to C1 (a single CC43 WW domain) was studied by measuring enthalpy changes using a Nano ITC instrument (TA Instruments, New Castle, Del., USA). All peptides were dissolved and dialyzed overnight (MWCO=1.0 kDa) against PBS (pH 7.4) to ensure buffer matching. 2 mM of C1 solution was loaded in the injection syringe and titrated into 0.2 mM P1 or P2 solution in the sample cell in a sequence of 16 injections of 3 µL volumes. Successive injections were delayed by 5 min to allow equilibration. All experiments were conducted at 25° C. with constant stirring at 300 rpm. The NanoAnalyze software was used to transform raw heat against injection number into enthalpy change per mole of injectant against molar ratio. The integrated isotherms were then fitted to an independent site model to obtain thermodynamic parameters of binding.

2.4. Bulk Rheological Measurement

Each WW domain in C7 is treated as one C unit. Since ITC measurements revealed that both P1 and P2 bind to C1 with 1:1 stoichiometry, each pendant peptide group (P1 or P2) in the 8-arm-PEG-peptide conjugates was treated as one P unit regardless of multivalency. Thus, in calculating C:P ratios, P2 is considered as one P unit even though it has two repeats of the proline-rich peptide domain.

Unless otherwise specified, MITCH variants 8P1-20k, 8P2-20k, 8P1-40k, and 8P2-40k refer to hydrogel mixtures of C7 and 8-arm-PEG-P1 (20 kDa), 8-arm-PEG-P2 (20 kDa), 8-arm-PEG-P1 (40 kDa), and 8-arm-PEG-P2 (40 kDa), respectively, mixed to achieve a final concentration of 10% w/v and a C:P ratio of 1:1.

Dynamic oscillatory rheology experiments were performed on a stress-controlled rheometer (AR-G2, TA instrument, New Castle, Del.) using a 25-mm diameter cone-plate geometry. Gel samples were prepared by mixing equal volumes of 10% w/v 8-arm-PEG-peptide conjugates with 10% w/v C7, at volume ratios corresponding to various C:P stoichiometric ratios. Samples were loaded immediately onto the rheometer, and a humidity chamber was secured in place to prevent dehydration. Frequency sweeps at 37° C. were performed at 5% constant strain to obtain storage modulus G' and loss modulus G".

Shear-thinning and self healing properties of the gel samples (8P1-20k, 8P2-20k, 8P1-40k, 8P2-40k, concentration=10% w/v, C:P ratio=1:1) were characterized by measuring linear viscosities Op under a time sweep mode, at alternating low and high shear rates of 0.1 s$^{-1}$ and 10 s$^{-1}$, respectively, for 30 s each and a total of 150 s.

2.5. Fluorescence Recovery after Photobleaching (FRAP) Diffusivity Measurement Fluorescence recovery after photobleaching (FRAP) measurement was performed using dextran (MW=20, 40, and 70 kD) conjugated to fluorescein isothiocyanate (FITC) (Invitrogen). Dextran was individually mixed with various MITCH-PEG formulations (8P1-20k, 8P2-20k, 8P1-40k, and 8P2-40k; gel volume=30 µL, concentration=10% w/v, C:P ratio=1:1) at a final dextran concentration of 4 mg/mL, and the total fluorescence intensity was visualized at 37° C. using a Leica TCS SP5 confocal microscope at low light intensity. Photobleaching was done by exposing a 100×100 µm spot in the field of view to high intensity laser light. A series of images were taken every three seconds for five minutes to track the recovery of fluorescence. Control experiments were also performed using PBS, rat-tail Type I collagen (2 mg/mL, BD Biosciences), and growth-factor-reduced Matrigel (BD Biosciences) as diffusion media, prepared according to manufacturers' protocols. The resulting fluorescence recovery profiles were modeled by Fickian diffusion according to a previously reported method to calculate dextran diffusivities. [21].

2.6. Kinetics of Hydrogel Erosion and Dextran and VEGF Release

MITCH-PEG formulations (8P1-20k, 8P2-20k, 8P1-40k, and 8P2-40k; gel volume=30 concentration=10% w/v, C:P ratio=1:1) were formed by mixing the PEG-peptide component and C7 in a circular silicone mold (diameter=4 mm, height=2 mm) within a 24-well plate (n≥3). The mixture was allowed to undergo sol-gel phase transition for 15 min at 37° C. in a humidified incubator, after which 1.5 mL of PBS was added to each well. Sampling volumes of 100 µL were obtained from the PBS supernatant and wells were replenished with 100 of fresh PBS over a period of 14 days. Gel erosion kinetics were studied by using absorbance spectroscopy at 280 nm (SpectraMax M2 Spectrophotometer, Molecular Devices) to measure the amount of protein released into the supernatant at each time point.

To study dextran release kinetics, 20 kD FITC-dextran (Invitrogen) was encapsulated in various MITCH-PEG formulations (8P1-20k, 8P2-20k, 8P1-40k, and 8P2-40k; gel volume=concentration=10% w/v, C:P ratio=1:1) by first mixing with the PEG-peptide component and subsequently with C7 in a circular silicone mold (diameter=4 mm, height=2 mm) within a 24-well plate (n≥3). The initial amount of dextran in each gel was 6 µg, at a concentration of 0.2 mg/mL. The mixture was allowed to gel for 15 min at 37° C. in a humidified incubator, after which 1.5 mL of PBS was added to each well. Release kinetics were followed by sampling and replenishing 100 µL of the PBS supernatant over a period of 14 days. The amount of dextran that had been released in the sampling volume was quantified using a SpectraMax M2 Spectrophotometer (Molecular Devices) to measure fluorescence at 488 nm.

Recombinant human VEGF$_{165}$ (carrier free, R&D Systems) was dissolved in PBS (supplemented with 0.1% w/v BSA) and encapsulated in various MITCH-PEG formulations (8P1-20k, 8P2-20k, 8P1-40k, and 8P2-40k; gel volume=30 µL, concentration=10% w/v, C:P ratio=1:1) by first mixing with the PEG-peptide component and subsequently with C7 in a circular silicone mold (diameter=4 mm, height=2 mm) within a 24-well plate (n≥3). The initial amount of VEGF in each gel was 3 μg, at a concentration of 0.1 mg/mL. The mixture was allowed to gel for 15 min at 37° C. in a humidified incubator, after which 1.5 mL of PBS (supplemented with 0.1% w/v BSA) was added to each well. Release kinetics were followed by sampling and replenishing 100 μL of the PBS supernatant over a period of 14 days. Samples were frozen at −80° C. immediately after collection and thawed prior to quantification. The amount of VEGF present in the supernatant at each time point was quantified using Human VEGF Quantikine ELISA Kit (R&D Systems), according to manufacturer's protocol.

2.7. Cell Culture and Maintenance

Human induced pluripotent stem cells (hiPSCs) were generated from adult dermal fibroblasts using retroviral constructs encoding Oct4, Sox2, c-Myc and Klf4 as described previously.[12] hiPSCs were cultured on mouse embryonic fibroblast feeder cells and maintained in standard WiCell human embryonic growth medium supplemented with 10 ng/ml basic fibroblast growth factor. Endothelial differentiation was initiated by incubating confluent cultures of hiPSCs with 1 mg/mL type IV collagenase for 10 min. Cells were then transferred to ultra low attachment dishes and cultured in differentiation medium (α-Minimum Eagle's Medium, 20% fetal bovine serum, L-glutamine, β-mercaptoethanol (0.05 mmol/L), 1% non-essential amino acids, bone morphogenetic protein-4 (BMP-4, 50 ng/mL, Peprotech), and vascular endothelial growth factor (VEGF-A, 50 ng/ml, Peprotech)) for 4 days to form embryoid bodies (EBs). On day 4, EBs were reattached to gelatin-coated dishes and further supplemented with VEGF-A for 10 days before purification. Differentiation medium was changed every 2 days.

On day 14 of differentiation, hiPSC-derived endothelial cells (hiPSC-ECs) were dissociated into single cells and purified by fluorescence activated cell sorting (FACS) using CD31 antibody (eBiosciences). Endothelial identity of the purified hiPSC-ECs was characterized following protocols reported in previous publications [12, 22]. To facilitate non-invasive tracking, hiPSC-ECs were lentivirally transduced with a double fusion reporter construct encoding firefly luciferase (Fluc) and enhanced green fluorescence protein (eGFP) under a ubiquitin promoter.[12] For use in cell encapsulation and injection experiments, hiPSC-ECs (Fluc+/eGFP+) were expanded in EGM-2MV medium (Lonza).

2.8. In Vitro Cell Encapsulation, Injection, and Quantification of Viability All in vitro encapsulation and injection experiments were performed with 25 μL gel volumes containing $3.3 \times 10^4$ cells. hiPSC-ECs were trypsinized and resuspended to a density of $6.7 \times 10^6$ cells/mL in EGM-2MV media. Cell suspension (5 μl) was first mixed with the 8-arm PEG-peptide conjugate solution (20% w/v in PBS) and PBS before further mixing with C7 (10% w/v in PBS). The volumes of 8-arm-PEG-peptide conjugate solution and C7 were adjusted to achieve a final C:P ratio of 1:1 at a total hydrogel concentration of 10% w/v.

For cell injection studies, the final mixing step with C7 was performed in the barrel of a 28 G insulin syringe. The mixture was allowed to gel for 5 min before injecting into a circular silicone mold (diameter=4 mm, height=2 mm) within a 24-well plate at a rate of ~0.5 mL/min (n≥4). For 3D culture studies, the C7 mixing step was performed directly in the silicone mold in a 24-well plate (n≥4), and the mixture was allowed to gel for 5 min before EGM-2MV media addition and incubation in EGM-2MV media. In both studies, cell suspension in PBS was included as control.

To assess cell viability, samples were incubated with D-luciferin (150 μg/mL), and bioluminescence imaging (BLI) was performed with an IVIS imaging system (Xenogen Corp.). The Living Image software (Xenogen Corp.) was used for data acquisition and analysis. BLI intensity was expressed in units of photons/cm$^2$/s/steradian.

Cells were fixed with 4% paraformaldehyde, permeabilized with 0.25% Triton X-100 solution in PBS, and blocked in 5% bovine serum albumin (BSA) and 0.5% Triton X-100 in PBS before incubation in anti-human CD31 primary mouse antibody (1:200, Cell Signaling Technology). All antibodies are dissolved in 2.5% BSA and 0.5% Triton X-100 in PBS. After 3 washes, samples were further incubated with Alexa Fluor 546 F(ab')2 Fragment of Goat Anti-Mouse IgG (H+L) (1:1000 dilution, Life Technologies), Alexa Fluor 633 Phalloidin (1:300 dilution, Life Technologies), and DAPI (1 μg/ml, Life Technologies) before washing and mounting in ProLong Gold Antifade (Life Technologies). Images of cell morphology were obtained using a Leica TCS SP5 confocal microscope.

2.9. Hindlimb Ischemia

Unilateral hindlimb ischemia was induced in male NOD SCID mice (12-16 weeks old) by ligating the left femoral artery, as previously reported.[12] The contralateral limb served as non-ischemic control. Surgery was performed under constant isoflurane anesthesia, and all animal procedures were approved by the Administrative Panel on Laboratory Animal Care at Stanford University. Immediately following ischemia induction, animals were randomly assigned to receive intramuscular (IM) injection in the gastrocnemius muscle (n=4 in each group), of the following payloads: 1) PBS; 2) MITCH-PEG; 3) hiPSC-ECs and VEGF in PBS; and 4) hiPSC-ECs and VEGF in MITCH-PEG. In this study, MITCH-PEG refers to the 8P2-20k gel variant (10% w/v, C:P ratio=1:1). Where applicable, $5 \times 10^5$ cells and 3 μg of human recombinant VEGF$_{165}$ (R&D systems) were delivered into each mouse.

Animals were euthanized on day 14 and the gastrocnemius tissues were isolated and flash-frozen in O.C.T. compound for cryosectioning and subsequent examination of hematoxylin and eosin (H&E) stained sections by a board-certified veterinary pathologist who was blinded to the goals of the study and the identity of the samples. Histology scores were given to each muscle tissue sample according to the criteria listed in Table 3.

TABLE 3

Histology score criteria.

| Score | Muscle Necrosis | Muscle Inflammation (Neutrophils and/or Macrophages) | Muscle Regeneration |
|---|---|---|---|
| 0 | none | none | none |
| 1 | minimal, scattered | minimal, scattered | minimal, scattered |
| 2 | mild, scattered to multifocal | mild, scattered to multifocal | mild, scattered to multifocal |
| 3 | moderate, multifocal | moderate, multifocal | moderate, multifocal |
| 4 | intense, multifocal to diffuse | intense, multifocal to diffuse | intense, multifocal to diffuse |

3. Results and Discussion

3.1. Design of an Avidity-Controlled MITCH-PEG System

Figure 10:
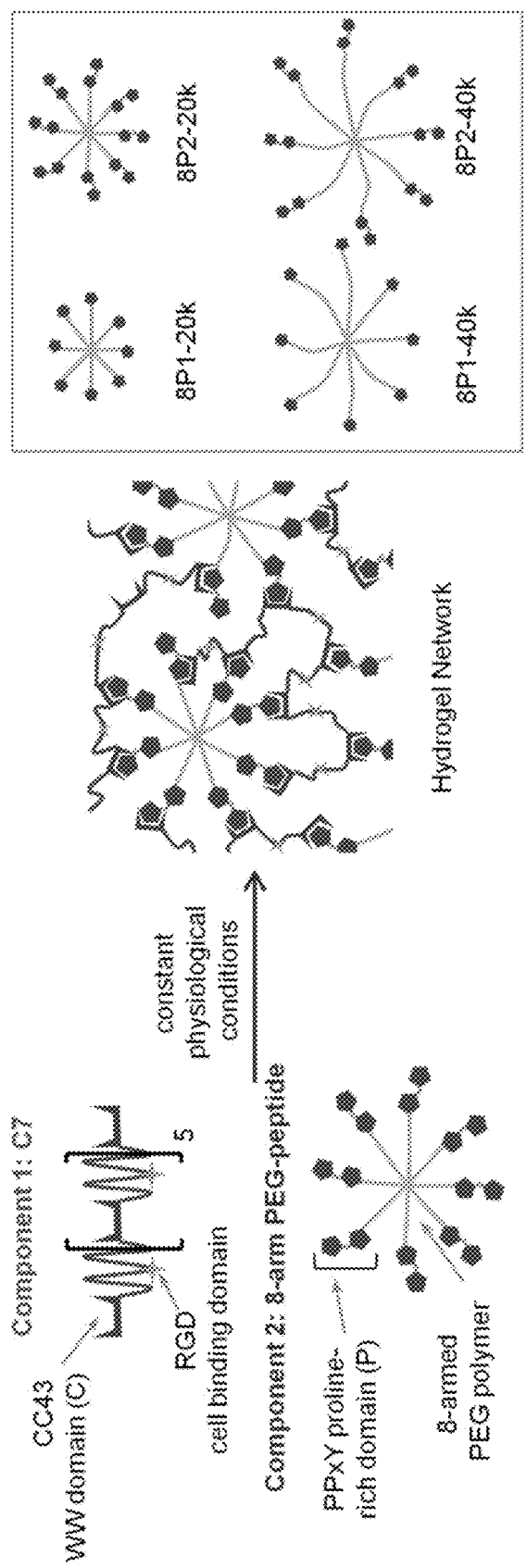
FIG. 10 shows a schematic of MITCH-PEG hydrogel formation according to an exemplary embodiment of the invention. Component 1 is a recombinant protein copolymer bearing CC43 WW domains (denoted as C) and RGD cell-binding domains. Component 2 is an 8-arm PEG-peptide conjugate bearing complementary proline-rich peptide domains (denoted as P). Simple mixing of the two components results in hydrogel network formation. Inset shows variants of the 8-arm PEG-peptide conjugate, created by varying domain repeat (P1 for one domain or P2 for two domains) and the PEG molecular weight (20 kDa or 40 kDa).
Figure 11A:
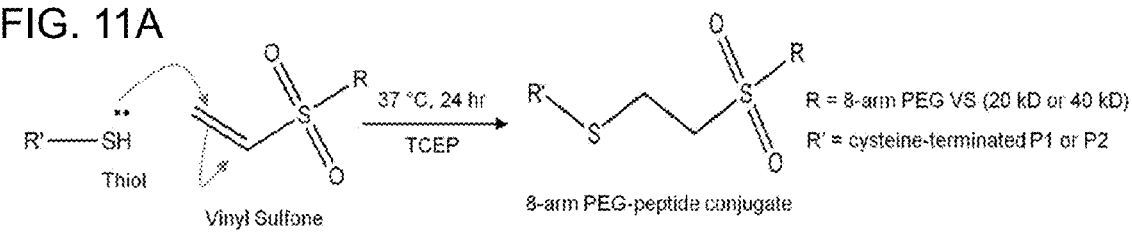
FIGS. 11A-C show characterization of peptide conjugation to PEG according to an exemplary embodiment of the invention.
Figure 11B:
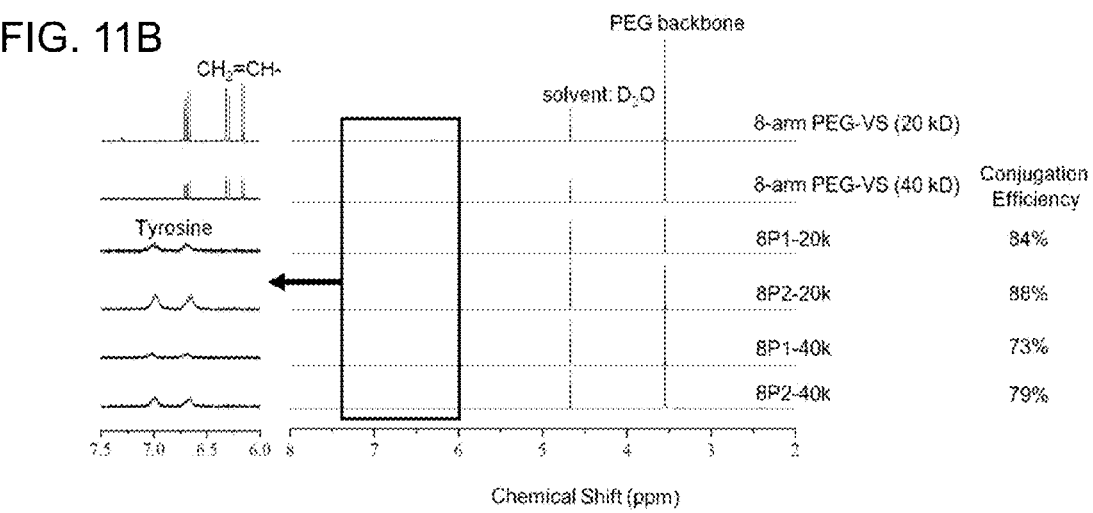
Figure 11C:
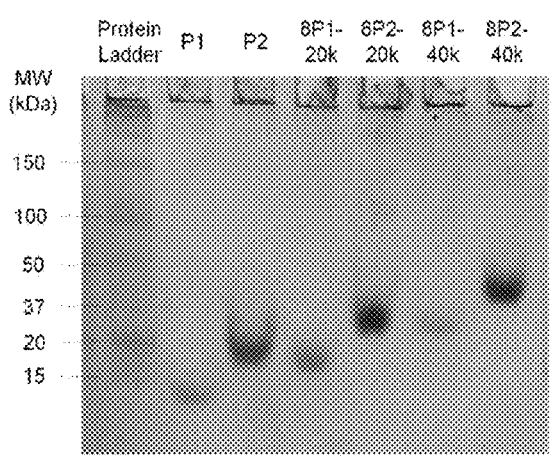

Inspired by our previously reported Mixing-Induced Two-Component Hydrogel (MITCH) system,[1, 7, 23] these materials (coined MITCH-PEG) also comprise two soluble polymers that assemble into hydrogel networks by specific molecular recognition between WW and proline-rich peptide domains upon simple mixing (FIG. 10). While the original MITCH system was designed from two, linear, engineered proteins, the MITCH-PEG system described here includes a single, linear, engineered protein (termed C7) and a multi-armed, peptide-modified polyethylene glycol (PEG). The C7 protein contains seven repeats of a computationally derived WW domain [1, 24] interspersed with a hydrophilic, random coil peptide sequence [7, 25] (FIG. 9). PEG is a highly hydrophilic, FDA-approved polymer that is readily decorated with peptides via covalent bioconjugation. To explore the potential tuning of hydrogel properties through avidity effects, an 8-arm PEG was decorated with either a single proline-rich peptide (termed P1) or a double repeat of the proline-rich peptide (P2). We believed that separating the two proline-rich binding peptides within the P2 sequence with a tetraglycine spacer would provide conformational flexibility to avoid steric hindrance upon binding to a single C domain. We further believed that this tetraglycine spacer would be too short to accommodate binding of two C domains simultaneously. Thus, while the P1 and P2 domains both bind to only a single C domain at a given time with a 1:1 stoichiometry, the P2 domain should have a higher effective binding strength compared to the P1 domain due to avidity. A Michael-type addition was chosen to bioconjugate the P1 or P2 peptides onto vinyl sulfone-terminated, 8-arm PEG (PEG-VS). This reaction between thiols and vinyl sulfones is a rapid and highly selective reaction that allows the conjugation of cysteine-containing compounds to be performed under aqueous physiological conditions.[26, 27] Reaction of cysteine-terminated P1 or P2 peptides with either 20 kDa or 40 kDa 8-arm PEG-VS (FIG. 11A), followed by purification by solvent extraction, generated four variants of 8-arm-PEG-peptide conjugates with high degrees of substitution (73-88% by NMR) (FIG. 11B). Success of the purification was characterized by SDS-PAGE, where only a single molecular weight species was observed for each purified product (FIG. 11C).

3.2. Mechanical Properties of MITCH-PEG are a Function of Component Molecular Weight and Avidity-Controlled Binding Strength Bulk mechanical properties of hydrogels depend on crosslinking density, which in noncovalent physical hydrogels is dictated by the individual polymer molecular weights, as well as the number and strength of crosslinking binding interactions per polymer unit. [28, 29] Star-shaped PEG-VS of various degrees of polymerization and arm numbers are available commercially, providing an off-the-shelf selection of molecular weights and functionality. We used 8-arm-PEG-VS with molecular weights of 20 kDa and 40 kDa as precursors to conjugation. The 4-arm counterparts failed to meet the critical functionality for forming a percolating gel network, as mixing with C7 produced viscous solutions with loss moduli (G") predominating the storage moduli (G') (data not shown).

Figures 12A, 12B, 12C:
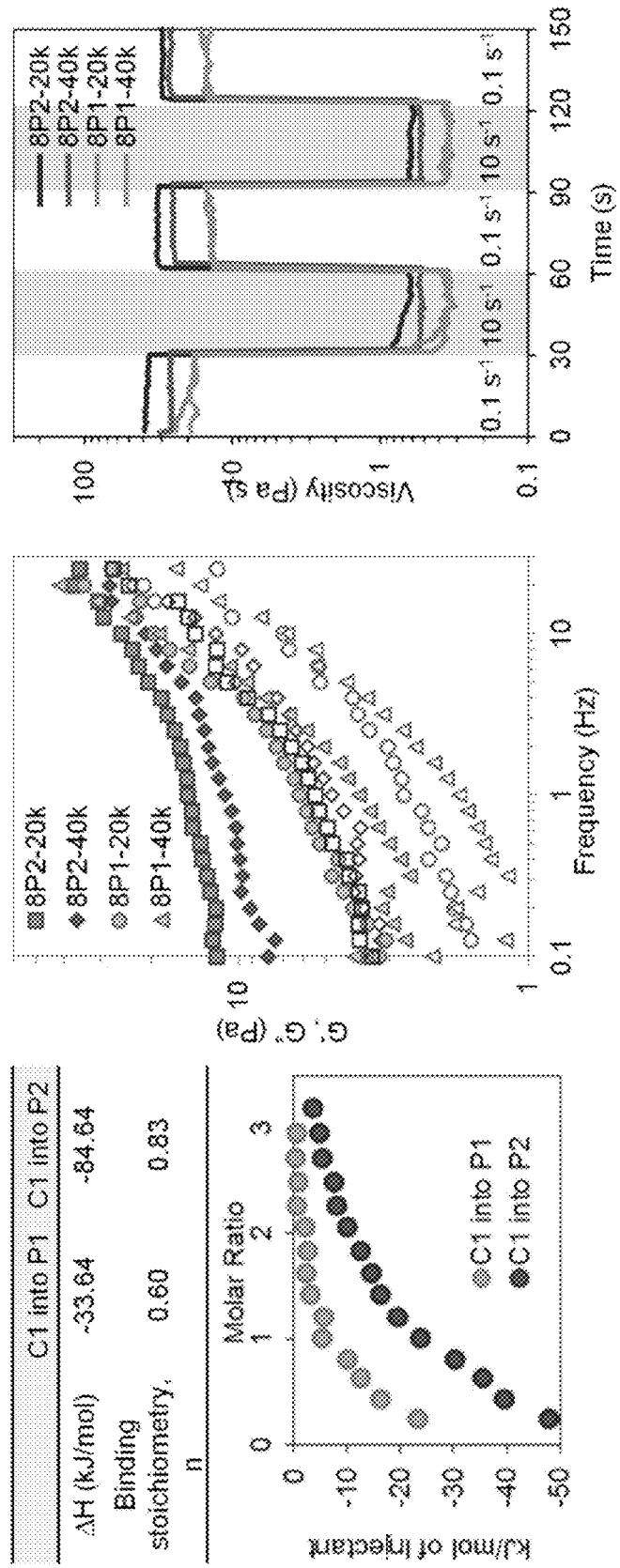
FIGS. 12A-C show dependence of hydrogel shear moduli and thixotropy on crosslinking strength and molecular weight between crosslinks according to an exemplary embodiment of the invention.

To tune the strength of peptide binding without investing in extensive peptide mutagenesis and screening, we take advantage of avidity effects, a multimerization strategy commonly used in antibody engineering to create high-affinity diabodies and triabodies.[30] As confirmation of our avidity peptide design, isothermal titration calorimetry (ITC) revealed that P2 binding with the complementary CC43 WW domain (denoted C1) had an exothermic binding enthalpy greater than two times that of P1-C1 binding (FIG. 12A). The ITC data also confirmed that the tetraglycine linker introduced to confer rotational freedom to the two P domains in P2 was sufficiently short to preclude two C1 domains from binding simultaneously, as no significant changes in binding stoichiometry were detected (FIG. 12A). The increase in C1:P2 binding energy is thus a consequence of prolonged binding duration as a single C1 domain dissociates and re-associates between the two adjacent P domains. In subsequent experimental design and analysis, each pendant peptide group (P1 or P2) in the 8-arm PEG-peptide conjugates was treated as one P unit regardless of multivalency.

Mixing of C7 with permutations of PEG molecular weight (20 kDa or 40 kDa) and binding strength (P1 or P2) creates four hydrogel variants (denoted 8P1-20k, 8P2-20k, 8P1-40k, and 8P2-40k). As expected, decreasing the PEG-peptide molecular weight or increasing the PEG-peptide binding strength resulted in stiffer hydrogels (FIG. 12B). 8P2-20k, with shorter arm length and stronger binding, exhibited the highest storage modulus (G'=15.0 Pa at 10% w/v and a C:P ratio of 1:1). At the same concentration and C:P ratio, 8P1-40k had the lowest storage modulus (G'=3.9 Pa).

Preformed MITCH-PEG hydrogels exhibited thixotropy, or the ability to shear-thin and self-heal. When subjected to linear shearing under alternating low and high shear rates, the materials responded by assuming high and low viscosity values in an instantaneous (<1 s) and reversible fashion (FIG. 12C). This sharp yielding transition under high shear is a consequence of transient unbinding between P and C peptides, while reformation of the P-C physical network junctions upon shear removal enables rapid self-healing. MITCH-PEG are thus ideal for injectable applications, where the hydrogels must yield and flow as low-viscosity materials under modest hand pressure and then recover the gel state immediately post-injection to prevent cargo sedimentation or diffusion into off-target tissue sites.

3.3. VEGF Delivery from MITCH-PEG with Tunable Kinetics

MITCH-PEG is an effective vehicle for controlled drug delivery due to several attributes. First, the mixing protocol of MITCH-PEG gelation supports growth factor incorporation in its bioactive format without exposing the growth factor to covalent crosslinkers or changes in pH, temperature, or ionic strength. Second, hydrogel mesh size, a key determinant of molecular diffusivity within a network, is easily tunable through appropriate selection of 8-arm-PEG-peptide conjugate.

Crosslinking density dictating hydrogel stiffness is inextricably linked to network mesh size. Therefore, drugs loaded through simple encapsulation in MITCH-PEG diffuse with decreasing mobility in stiffer hydrogel formulations. We used fluorescently-labeled dextran drug analogs and employed a spectroscopic technique called Fluorescence Recovery After Photobleaching (FRAP) [21] as an inexpensive, high throughput method for mapping diffusivity as a function of hydrogel mesh size and cargo molecular weight. A high intensity laser was focused onto a defined volume in the hydrogel where fluorescent dextran had been homogenously encapsulated, resulting in photobleaching. Subsequent diffusion of surrounding unbleached dextran molecules into the photobleached area produced time-dependent fluorescence recovery profiles (FIG. 13A) from which diffusivity constants of the encapsulated dextran molecules were computed (FIG. 13b,c). Diffusivity constants not only decreased with molecular weight, as expected, but also depended on PEG arm length (20 kDa vs. 40 kDa) and peptide binding strength (P1 vs. P2) in the same order as trends in hydrogel stiffness. Consequently, slowest and fastest diffusion corresponded to diametrically opposite formulations 8P2-20k and 8P1-40k, respectively. Diffusivity constants were also computed for dextran diffusing in growth factor-reduced Matrigel and rat-tail Type I collagen (2.5 mg/mL), two common cell transplantation matrices with comparable storage moduli as MITCH-PEG.[23, 31] displayed decreased Diffusivity was significantly lower in MITCH-PEG compared to both Matrigel and Type I collagen (FIGS. 13B-C).

Figure 14A:
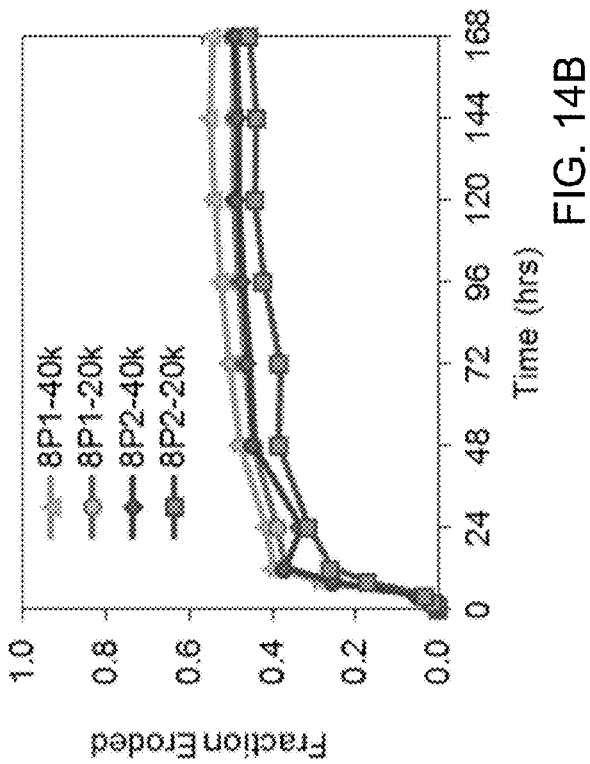
FIG. 14A-C show hinetics of hydrogel erosion and dextran and Vascular Endothelial Growth Factor (VEGF) release according to an exemplary embodiment of the invention.
Figure 14B:
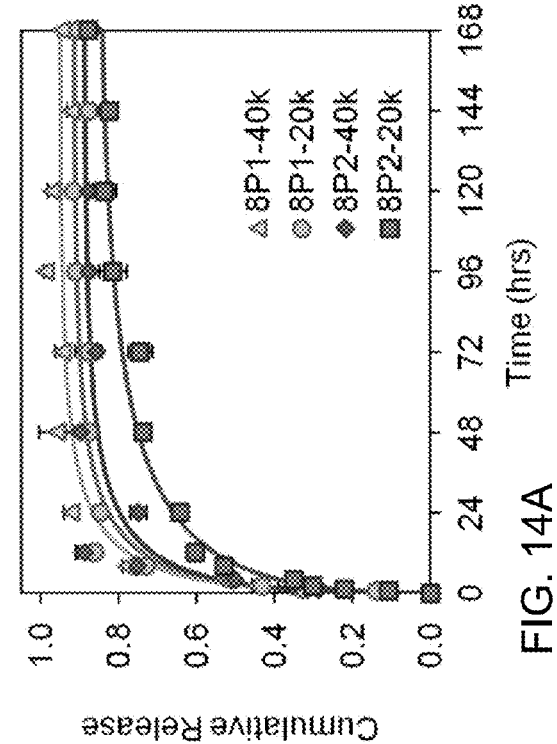
Figure 14C:
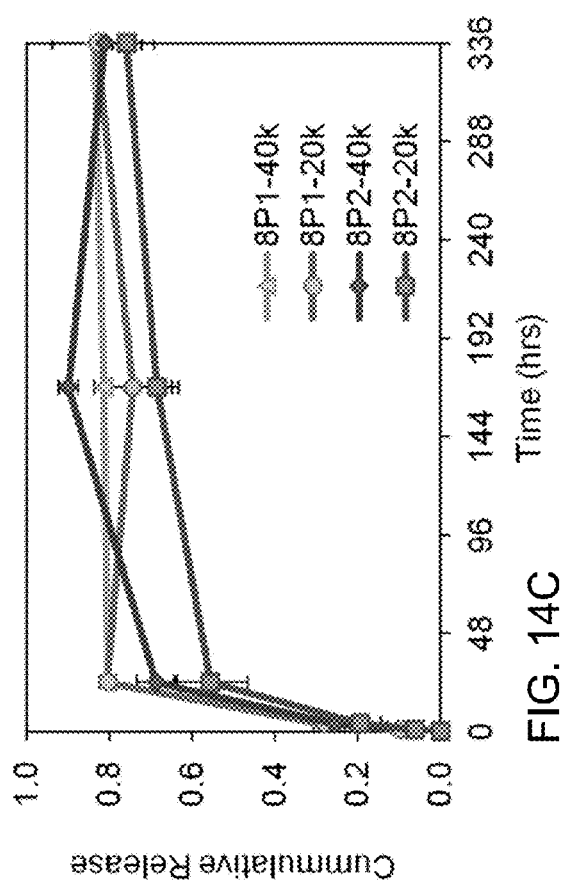

While FRAP experiments are material and time efficient, macro-diffusivity determinants such as hydrogel swelling, degradation, and initial burst release from the gel surface are not factored into the analysis. As such, actual bulk release profiles over longer timescales cannot be quantitatively predicted from FRAP data.[32] Release experiments by bulk gel immersion and sampling were therefore performed using the 20 kDa dextran drug analog (FIG. 14A), chosen for its comparable Stokes radius to that of VEGF.[33] The kinetics of drug delivery from a hydrogel into a medium is dependent on the loss of matrix material,[34] which in physical hydrogels such as MITCH-PEG occurs predominantly by surface erosion rather than internal degradation of matrix polymers. Since surface erosion is a function of crosslinking binding strength and density, the overall rates of matrix material loss obeyed the same trend as hydrogel stiffness (FIG. 14B). Material was lost steadily after an initial phase of rapid loss, driven in the first few hours of hydrogel submersion by dilution into the medium. The resulting bulk release curves of dextran were consistent with the underlying trends in hydrogel mechanical properties, mesh size, and erosion rates, with 8P2-20k and 8P1-40k corresponding to the slowest and fastest delivery rates, respectively (FIG. 14A).

In a previous hindlimb ischemia study, correlational mapping between VEGF concentration and angiogenic sprouting revealed a two-phase profile of high initial availability and low subsequent amounts as the optimal VEGF distribution for normal revascularization.[35] Recombinant human VEGF$_{165}$ released from MITCH-PEG into a medium of PBS was detectable by anti-VEGF monoclonal antibody in sandwich ELISA for up to 14 days (FIG. 14C), indicating the preservation of native tertiary structure. The 8P2-20k hydrogel formulation fulfilled this biphasic release criteria for both VEGF (FIG. 5c) and 20 kDa dextran (FIG. 14A), and was therefore selected as the carrier for subsequent in vitro cell culture and in vivo hindlimb ischemia experiments.

Figure 15B:
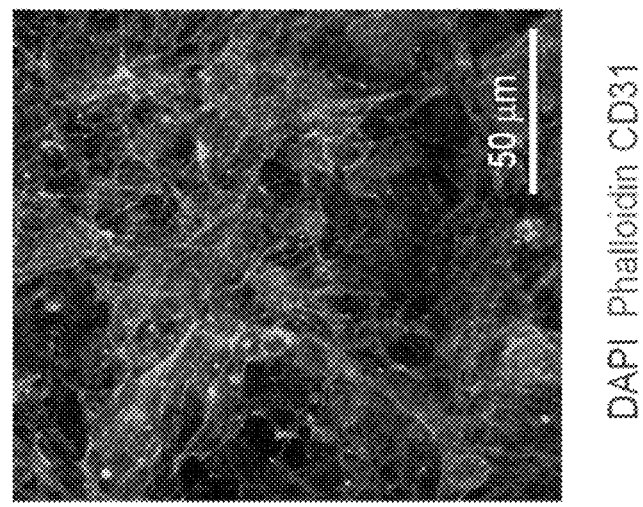
FIG. 15A-B show according to an exemplary embodiment of the invention in FIG. 15A bioluminescence imaging (BLI) quantification of acute human induced pluripotent stem cell-derived endothelial cell (hiPSC-EC) viability following in vitro injection. Pre-encapsulation of hiPSC-ECs (Fluc+) in MITCH improved post-injection viability relative to injected cells suspended in PBS,* $p<0.05$.
Figure 15A:
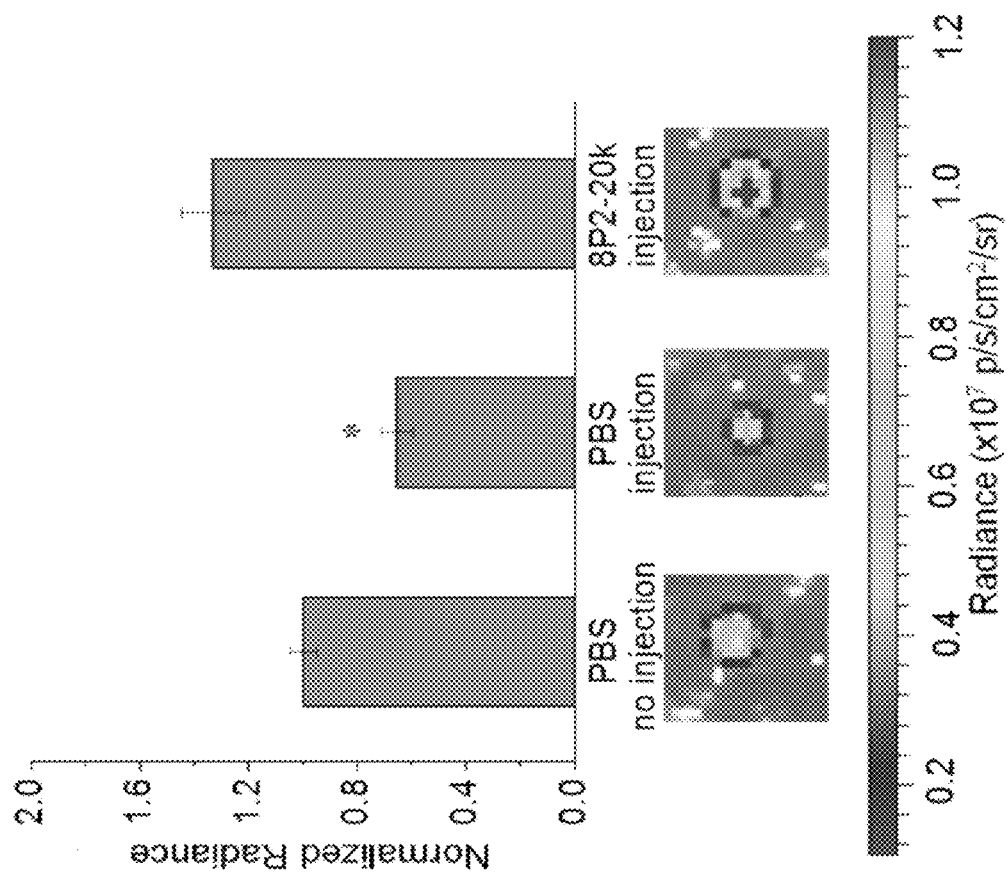

3.4. MITCH-PEG Improves Acute Post-Injection Viability of hiPSC-ECs In Vitro During high-shear flow in narrow capillaries or syringe needles, shear zones in thixotropic hydrogels have been observed to localize as narrow bands near the capillary wall while a broad central zone experiences negligible shear.[14, 15] Cells transported within the central plug are thus shielded from detrimental mechanical forces, thereby improving cell survival during the injection process. We therefore hypothesized that the thixotropic MITCH-PEG hydrogel would be able to enhance the viability of human induced pluripotent stem cell-derived endothelial cells (hiPSC-ECs) exposed to syringe injection compared to cell delivery in saline alone. To facilitate non-invasive monitoring of cell viability, hiPSC-ECs were stably transduced with a double fusion reporter construct encoding firefly-luciferase (Fluc) and enhanced green fluorescent protein (eGFP) under a constitutive ubiquitin promoter, as previously reported.[12] As expected, hiPSC-ECs delivered through a 28 G syringe needle at a flow rate of ~0.5 mL/min experienced a significant loss in cell viability when delivered in saline alone. In contrast, pre-encapsulation of the hiPSC-ECs within the 8P2-20k hydrogels prior to syringe delivery resulted in no loss of cell viability (FIG. 15A).

The recombinant DNA technology used to create the C7 component allows both crosslinking peptides and RGD cell-binding domains to be incorporated into the same protein polymer. As such, beyond structural protection, MITCH-PEG materials are capable of maintaining cell-matrix adhesion through integrin binding, an essential survival signal for endothelial cells (ECs).[36, 37] ECs deprived of integrin signaling rapidly undergo anoikis, a form of programmed cell death commonly experienced by transplanted cells upon matrix detachment.[38, 39] Cells encapsulated in 8P2-20k remained proliferative over 4 days of in vitro culture (FIG. 15B), implying material cytocompatibility and provision of a pro-survival microenvironment. Visualization of F-actin by confocal microscopy revealed well-spread cytoskeletal stress fiber morphologies, which serve as indirect evidence for integrin binding and focal adhesion formation (FIG. 15B).[40, 41]

3.5. Co-Delivery of hiPSC-ECs and VEGF in MITCH-PEG Improves Tissue Regeneration and Reduces Necrosis in the Ischemic Calf Muscle Treatment of murine hindlimb ischemia by hiPSC-EC injection was motivated by the need for a minimally invasive and enduring therapy for PAD.[12] When delivered in liquid medium, hiPSC-EC were found to induce capillary formation by secreting angiogenic cytokines while directly incorporating into expanding vascular networks.[12] As symptomatic relief generally correlates with the number of viable donor cells,[42, 43] improving post-transplantation cell survival would solve a major bottleneck in cell regenerative therapy. Treatment of donor cells with pro-survival factors is one strategy for boosting viability.[16, 17] VEGF has a range of well-documented pro-survival and pro-proliferation effects on endothelial cells.[44] In the current study, luciferase-positive hiPSC-ECs were co-injected with VEGF intramuscularly into the ischemic calf of non-obese diabetic severe combined immune deficient (NOD SCID) mice immediately following femoral artery ligation either using 8P2-20k as a delivery vehicle or delivery in phosphate-buffered saline (PBS).

Superficially, the affected hindpaw digits of mice receiving hiPSC-ECs and VEGF co-delivered within MITCH-PEG developed sporadic necrosis of the nails only, while the mice receiving hiPSC-ECs and VEGF co-delivered within PBS were observed to have partial or full digit necrosis with subsequent self-amputation. To evaluate the extent of inflammation, necrosis, and regeneration, skeletal muscle tissues were isolated and cryosectioned for histologic evaluation two weeks post-injection. Sections from non-injured muscle tissue served as a control. Histology scores indicated that hiPSC-ECs and VEGF co-delivered within MITCH-PEG resulted in minimal inflammation and virtually no necrosis of affected skeletal muscle, while allowing for development of a viable, robust regenerative response by the myofibers (FIG. 16A-C). Interestingly, injection of 8P2-20k into the ischemic site alone (without encapsulated hiPSC-ECs or VEGF)

resulted in higher levels of both necrosis and regeneration compared to delivery of PBS alone.

Figure 16F:
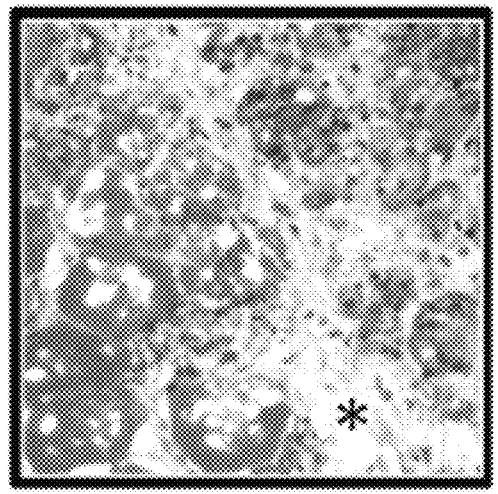
Figure 16E:
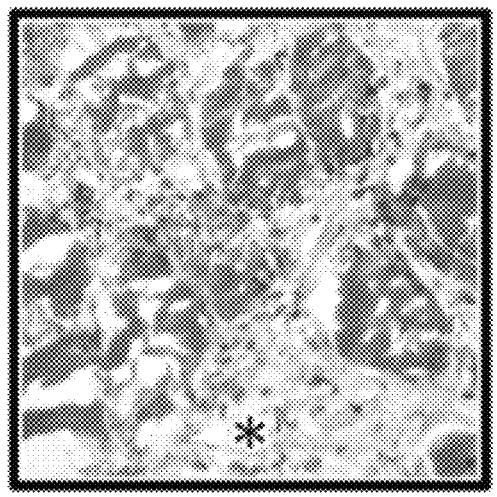

Representative histological slices confirm the pathologist scoring. In the control mice (no ischemic injury), the skeletal muscle is histologically normal, characterized by myofibers with a roughly angular shape and delineated cell membranes enclosing homogenous, eosinophilic (red) sarcoplasm; sarcoplasm with few or no clear spaces (i.e. glycogen accumulation); nuclei that are flattened and dark with eccentric location at the periphery of the myofiber; and a minimal amount of connective tissues between myofibers, resulting in close packing of the myofibers (FIG. 16D). In the ischemic mice with PBS delivery, there are changes consistent with inflammation and myofiber necrosis (FIG. 16E). The inflammation is characterized by expansion of the connective tissues between myofibers (black asterisk) due to poorly-staining edema fluid and loose, disorganized collagen deposition (i.e. early fibrosis). The expanded connective tissue also contains some neutrophils and macrophages (i.e. nucleated inflammatory cells). The myofiber necrosis is characterized by swelling of myofibers with increased cell diameter and loss of angular shape, hypereosinophilia (deeper red) of the sarcoplasm, a "moth-eaten" fragmentation appearance of the sarcoplasm, presence of centralized clear spaces in the sarcoplasm (i.e. glycogen accumulation, which is indicative of cellular stress and injury), loss of cell membrane integrity, and loss of nuclei. In the ischemic mice receiving the 8P2-20k MITCH-PEG injections, the changes are similar to that for PBS injection except that some myofibers have survived the ischemia (lower right corner) and show an early regenerative response (FIG. 16F). The surviving myofibers are much smaller and contain smaller amounts of glycogen (i.e. small clear spaces) compared with the necrotic myofibers. The nuclei are more round and plump and located centrally, both indicative of a regenerative response.

Figure 16H:
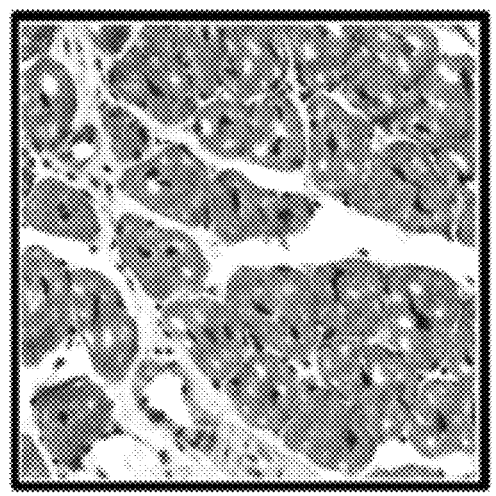
Figure 16G:
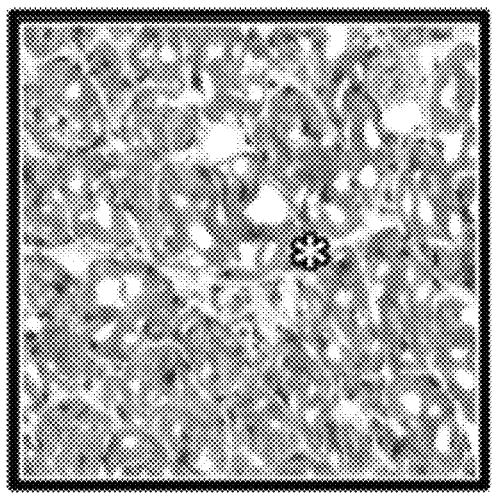

In the ischemic mice that received co-delivery of hiPSC-ECs and VEGF using a PBS carrier, there are milder inflammatory changes, a robust but still early myofiber regenerative response, and no evidence for necrosis (FIG. 16G). The inflammation is composed of much less edema, small scattered amounts of collagen deposition, and few inflammatory cells in the connective tissues (white asterisk) compared to the mice injected with the PBS carrier or the MITCH-PEG carrier alone. The myofiber regeneration appears more robust than in the mice receiving only the MITCH-PEG carrier, with the myofibers appearing larger; however, the response is still quite early—myofiber shape and size is quite variable, there is substantial glycogen accumulation (large central clear spaces) inside the sarcoplasm, and the nuclei remain centralized and ovoid/plump in shape. Finally, in the ischemic mice that received co-delivery of hiPSC-ECs and VEGF using the MITCH-PEG carrier, there is only minimal inflammation present, the regenerative response is more mature, and there is no necrosis evident (FIG. 16H). The inflammation comprises of minimal amounts of fibrosis with minimal edema and occasional inflammatory cells in the connective tissues. The myofibers all appear in a more mature stage of regeneration, the features of which include more uniform myofiber shape and size, the presence of smaller amounts of glycogen (smaller, scattered clear spaces) in the sarcoplasm, and multiple central nuclei that are more condensed and flattened.

Taken together, these data suggest that co-delivery of hiPSC-ECs and VEGF using a novel, injectable MITCH-PEG carrier can enhance the therapeutic, regenerative potential of these cells. Furthermore, these data support the more detailed preclinical study of the MITCH-PEG delivery system within animal models of ischemic disease and injury.

4. Conclusions

We present a biomimetic strategy to control hydrogel mechanical properties and drug release kinetics by designing avidity peptides that control the hydrogel physical crosslinking. The avidity peptides, which presented two binding domains in close proximity, more than doubled the effective enthalpy of binding compared to a single domain alone. These avidity peptides were bioconjugated to a multi-armed PEG molecule to enable spontaneous hetero-assembly with a linear, engineered protein through physical, molecular recognition of the peptide structure. This Mixing-Induced Two-Component Hydrogel (MITCH) strategy is able to encapsulate viable hiPSC-ECs and bioactive VEGF without the use of chemical crosslinkers or any changes in temperature, pH, or ionic concentration. The crosslinking density in these MITCH-PEG materials was tuned both by altering the PEG molecular weight and by exploiting peptide avidity. As expected, increases in crosslinking density resulted in stiffer hydrogels with slower diffusion, surface erosion, and bulk release kinetics. These materials may be well suited for regenerative medicine applications that involve direction injection of stem cell-derived therapies. As a proof of principle, hiPSC-ECs remained proliferative when encapsulated and cultured within MITCH-PEG. Furthermore, pre-encapsulation of hiPSC-ECs within MITCH-PEG was found to sustain cell viability when subjected to injection through a 28 G syringe needle. In a hindlimb ischemia injury model, co-delivery of hiPSC-ECs with VEGF from MITCH-PEG reduced inflammation and necrosis while improving muscle regeneration compared to co-delivery from saline. Taken together, these data suggest that these injectable materials address several challenges in stem cell-based therapeutics by providing a matrix that protects cells from damage during syringe needle injection, presenting an integrin ligand to promote cell adhesion and to prevent anoikis, and enabling the co-delivery and sustained release of bioactive pro-survival factors. These results warrant future preclinical studies into the biocompatibility and biodistribution of MITCH-PEG and its degradation products in models of ischemic injury and disease.

REFERENCES

[1] C. T. Wong Po Foo, J. S. Lee, W. Mulyasasmita, A. Parisi-Amon, S. C. Heilshorn, Two-component protein-engineered physical hydrogels for cell encapsulation, Proc Natl Acad Sci USA, 106 (2009) 22067-22072.

[2] H. D. Lu, M. B. Charati, I. L. Kim, J. A. Burdick, Injectable shear-thinning hydrogels engineered with a self-assembling Dock-and-Lock mechanism, Biomaterials, 33 (2012) 2145-2153.

[3] H. D. Lu, D. E. Soranno, C. B. Rodell, I. L. Kim, J. A. Burdick, Secondary Photocrosslinking of Injectable Shear-Thinning Dock-and-Lock Hydrogels, Advanced Healthcare Materials, 2 (2013) 1028-1036.

[4] F. Ito, K. Usui, D. Kawahara, A. Suenaga, T. Maki, S. Kidoaki, H. Suzuki, M. Taiji, M. Itoh, Y. Hayashizaki, T. Matsuda, Reversible hydrogel formation driven by protein-peptide-specific interaction and chondrocyte entrapment, Biomaterials, 31 (2010) 58-66.

[5] T. Z. Grove, C. O. Osuji, J. D. Forster, E. R. Dufresne, L. Regan, Stimuli-Responsive Smart Gels Realized via Modular Protein Design, Journal of the American Chemical Society, 132 (2010) 14024-14026.

[6] J. Wang, J. Zhang, X. Zhang, H. Zhou, A protein-based hydrogel for in vitro expansion of mesenchymal stem cells, PLoS One, 8 (2013) e75727.

[7] W. Mulyasasmita, J. S. Lee, S. C. Heilshorn, Molecular-level engineering of protein physical hydrogels for predictive sol-gel phase behavior, Biomacromolecules, 12 (2011) 3406-3411.

[8] S. Hong, P. R. Leroueil, I. J. Majoros, B. G. Orr, J. R. Baker, Jr., M. M. Banaszak Holl, The binding avidity of a nanoparticle-based multivalent targeted drug delivery platform, Chem Biol, 14 (2007) 107-115.

[9] A. Barnard, D. K. Smith, Self-assembled multivalency: dynamic ligand arrays for high-affinity binding, Angew Chem Int Ed Engl, 51 (2012) 6572-6581.

[10] D. Grunstein, M. Maglinao, R. Kikkeri, M. Collot, K. Barylyuk, B. Lepenies, F. Kamena, R. Zenobi, P. H. Seeberger, Hexameric supramolecular scaffold orients carbohydrates to sense bacteria, J Am Chem Soc, 133 (2011) 13957-13966.

[11] N. F. Huang, J. Okogbaa, A. Babakhanyan, J. P. Cooke, Bioluminescence imaging of stem cell-based therapeutics for vascular regeneration, Theranostics, 2 (2012) 346-354.

[12] A. J. Rufaihah, N. F. Huang, S. Jame, J. C. Lee, H. N. Nguyen, B. Byers, A. De, J. Okogbaa, M. Rollins, R. Reijo-Pera, S. S. Gambhir, J. P. Cooke, Endothelial cells derived from human iPSCS increase capillary density and improve perfusion in a mouse model of peripheral arterial disease, Arterioscler Thromb Vasc Biol, 31 (2011) e72-79.

[13] B. A. Aguado, W. Mulyasasmita, J. Su, K. J. Lampe, S. C. Heilshorn, Improving viability of stem cells during syringe needle flow through the design of hydrogel cell carriers, Tissue Eng Part A, 18 (2012) 806-815.

[14] C. Yan, M. E. Mackay, K. Czymmek, R. P. Nagarkar, J. P. Schneider, D. J. Pochan, Injectable solid peptide hydrogel as a cell carrier: effects of shear flow on hydrogels and cell payload, Langmuir, 28 (2012) 6076-6087.

[15] B. D. Olsen, J. A. Kornfield, D. A. Tirrell, Yielding Behavior in Injectable Hydrogels from Telechelic Proteins, Macromolecules, 43 (2010) 9094-9099.

[16] M. A. Laflamme, K. Y. Chen, A. V. Naumova, V. Muskheli, J. A. Fugate, S. K. Dupras, H. Reinecke, C. Xu, M. Hassanipour, S. Police, C. O'Sullivan, L. Collins, Y. Chen, E. Minami, E. A. Gill, S. Ueno, C. Yuan, J. Gold, C. E. Murry, Cardiomyocytes derived from human embryonic stem cells in pro-survival factors enhance function of infarcted rat hearts, Nat Biotechnol, 25 (2007) 1015-1024.

[17] H. Haider, M. Ashraf, Strategies to promote donor cell survival: combining preconditioning approach with stem cell transplantation, J Mol Cell Cardiol, 45 (2008) 554-566.

[18] S. M. Ryan, G. Mantovani, X. Wang, D. M. Haddleton, D. J. Brayden, Advances in PEGylation of important biotech molecules: delivery aspects, Expert Opin Drug Deliv, 5 (2008) 371-383.

[19] H. Sugimoto, Y. Hamano, D. Charytan, D. Cosgrove, M. Kieran, A. Sudhakar, R. Kalluri, Neutralization of circulating vascular endothelial growth factor (VEGF) by anti-VEGF antibodies and soluble VEGF receptor 1 (sFlt-1) induces proteinuria, J Biol Chem, 278 (2003) 12605-12608.

[20] G. von Degenfeld, A. Banfi, M. L. Springer, R. A. Wagner, J. Jacobi, C. R. Ozawa, M. J. Merchant, J. P. Cooke, H. M. Blau, Microenvironmental VEGF distribution is critical for stable and functional vessel growth in ischemia, FASEB J, 20 (2006) 2657-2659.

[21] P. Jonsson, M. P. Jonsson, J. O. Tegenfeldt, F. Hook, A method improving the accuracy of fluorescence recovery after photobleaching analysis, Biophys J, 95 (2008) 5334-5348.

[22] A. J. Rufaihah, N. F. Huang, J. Kim, J. Herold, K. S. Volz, T. S. Park, J. C. Lee, E. T. Zambidis, R. Reijo-Pera, J. P. Cooke, Human induced pluripotent stem cell-derived endothelial cells exhibit functional heterogeneity, Am J Transl Res, 5 (2013) 21-35.

[23] A. Parisi-Amon, W. Mulyasasmita, C. Chung, S. C. Heilshorn, Protein-engineered injectable hydrogel to improve retention of transplanted adipose-derived stem cells, Adv Healthc Mater, 2 (2013) 428-432.

[24] W. P. Russ, D. M. Lowery, P. Mishra, M. B. Yaffe, R. Ranganathan, Natural-like function in artificial WW domains, Nature, 437 (2005) 579-583.

[25] W. A. Petka, J. L. Harden, K. P. McGrath, D. Wirtz, D. A. Tirrell, Reversible hydrogels from self-assembling artificial proteins, Science, 281 (1998) 389-392.

[26] M. P. Lutolf, J. A. Hubbell, Synthesis and physicochemical characterization of end-linked poly(ethylene glycol)-co-peptide hydrogels formed by Michael-type addition, Biomacromolecules, 4 (2003) 713-722.

[27] M. P. Lutolf, G. P. Raeber, A. H. Zisch, N. Tirelli, J. A. Hubbell, Cell-responsive synthetic hydrogels, Advanced Materials 15 (2003) 888-892.

[28] P. J. Flory, Molecular size distributions in three dimensional polymers. I. Gelation., J Am Chem Soc., 63 (1941) 3083-3090.

[29] W. H. Stockmayer, Theory of molecular size distribution and gel formation in branched-chain polymers, J Chem Phys, 11 (1943) 45-55.

[30] A. Todorovska, R. C. Roovers, O. Dolezal, A. A. Kortt, H. R. Hoogenboom, P. J. Hudson, Design and application of diabodies, triabodies and tetrabodies for cancer targeting, J Immunol Methods, 248 (2001) 47-66.

[31] M. H. Zaman, L. M. Trapani, A. L. Sieminski, D. Mackellar, H. Gong, R. D. Kamm, A. Wells, D. A. Lauffenburger, P. Matsudaira, Migration of tumor cells in 3D matrices is governed by matrix stiffness along with cell-matrix adhesion and proteolysis, Proc Natl Acad Sci USA, 103 (2006) 10889-10894.

[32] F. Brandl, F. Kastner, R. M. Gschwind, T. Blunk, J. Tessmar, A. Gopferich, Hydrogel-based drug delivery systems: comparison of drug diffusivity and release kinetics, J Control Release, 142 (2010) 221-228.

[33] V. Eremina, J. A. Jefferson, J. Kowalewska, H. Hochster, M. Haas, J. Weisstuch, C. Richardson, J. B. Kopp, M. G. Kabir, P. H. Backx, H. P. Gerber, N. Ferrara, L. Barisoni, C. E. Alpers, S. E. Quaggin, VEGF inhibition and renal thrombotic microangiopathy, N Engl J Med, 358 (2008) 1129-1136.

[34] Y. Fu, W. J. Kao, Drug release kinetics and transport mechanisms of non-degradable and degradable polymeric delivery systems, Expert Opin Drug Deliv, 7 (2010) 429-444.

[35] E. A. Silva, D. J. Mooney, Effects of VEGF temporal and spatial presentation on angiogenesis, Biomaterials, 31 (2010) 1235-1241.

[36] S. Stromblad, D. A. Cheresh, Integrins, angiogenesis and vascular cell survival, Chem Biol, 3 (1996) 881-885.

[37] F. Re, A. Zanetti, M. Sironi, N. Polentarutti, L. Lanfrancone, E. Dejana, F. Colotta, Inhibition of anchorage-dependent cell spreading triggers apoptosis in cultured human endothelial cells, J Cell Biol, 127 (1994) 537-546.

[38] E. Chavakis, S. Dimmeler, Regulation of endothelial cell survival and apoptosis during angiogenesis, Arterioscler Thromb Vasc Biol, 22 (2002) 887-893.

[39] J. B. Michel, Anoikis in the cardiovascular system: known and unknown extracellular mediators, Arterioscler Thromb Vasc Biol, 23 (2003) 2146-2154.

[40] F. G. Giancotti, E. Ruoslahti, Integrin signaling, Science, 285 (1999) 1028-1032.
[41] S. I. Fraley, Y. Feng, R. Krishnamurthy, D. H. Kim, A. Celedon, G. D. Longmore, D. Wirtz, A distinctive role for focal adhesion proteins in three-dimensional cell motility, Nat Cell Biol, 12 (2010) 598-604.
[42] A. Le Huu, A. Paul, L. Xu, S. Prakash, D. Shum-Tim, Recent advancements in tissue engineering for stem cell-based cardiac therapies, Ther Deliv, 4 (2013) 503-516.
[43] Z. Raval, D. W. Losordo, Cell therapy of peripheral arterial disease: from experimental findings to clinical trials, Circ Res, 112 (2013) 1288-1302.
[44] N. Ferrara, H. P. Gerber, J. LeCouter, The biology of VEGF and its receptors, Nat Med, 9 (2003) 669-676.

2. Injectable Hydrogels with In Situ Double Network Formation for Cell Transplantation

Abstract

Cell transplantation via direct cell injection at the target site is a minimally invasive and clinically preferred strategy for treating various injuries and degenerative diseases. The therapeutic success of the functional recovery critically hinges on the survival and subsequent maintenance of the transplanted cells. We previously designed a recombinant protein polymer system that forms a mixing-induced two-component hydrogel (MITCH), which is shear-thinning and cell-protective during syringe injection. However, MITCH was completely resorbed in vivo within two weeks and had a shear modulus of ~10 Pa, which may be too compliant for many therapeutic applications. To address these limitations, we designed an injectable hydrogel that undergoes two different physical crosslinking mechanisms. The first crosslinking step occurs ex vivo through peptide-based molecular recognition to encapsulate cells within a physical hydrogel, while the second crosslinking step occurs in situ through a thermal phase transition to form a reinforcing network. Specifically, the molecular recognition takes place between a star-shaped peptide-polyethylene glycol (PEG) copolymer binding to an engineered recombinant protein, while the thermal phase transition is rendered via a thermo-responsive poly(N-isopropylacrylamide) (PNIPAM) segment tethered to the PEG. At room temperature, the physical hydrogel is shear-thinning and self-healing to facilitate gentle cell encapsulation and transplantation by syringe injection. At body temperature, the hydrogel forms a secondary network resulting in a 10-fold increase in shear modulus and significantly reduced erosion rates and prolonged retention time. Human adipose-derived stromal cells (hASCs) exposed to hand-injection through a 28-gauge syringe needle were significantly protected from disruptive mechanical forces when encapsulated within the hydrogel compared to injection of cells in medium alone (93±4% vs. 69±5% cell viability, respectively). At body temperature, the hASCs remained proliferative and became well-spread in three-dimensional cultures for two weeks. In vivo subcutaneous injection of hASCs within the hydrogel to a murine model demonstrated prolonged gel retention as well as cell retention due to the presence of double networks. These results suggest that in situ formation of a reinforcing network within an already existing hydrogel can enhance mechanical properties and retention time, and thereby improving long-term cell protection and providing support towards functional tissue regeneration.

EXPERIMENTAL SECTION

Material Synthesis and Hydrogel Preparation.

The C7 recombinant protein polymer was cloned, synthesized, and purified as reported previously. Briefly, the DNA sequence encoding the C7 block copolymer was cloned into the pET-15b vector (Novagen) and transformed into the BL21 (DE3)pLysS *Escherichia coli* host strain (Life Technologies). The protein was expressed following isopropyl β-D-1-thiogalactopyranoside (IPTG) induction, purified by affinity chromatography via the specific binding of N-terminal polyhistidine tag to Ni-nitrilotriacetic acid resin (Qiagen), dialyzed against phosphate-buffered saline (PBS), and concentrated by diafiltration across Amicon Ultracel filter units (Millipore).

8-arm polyethylene glycol vinyl sulfone (8-arm PEG-VS) with nominal molecular weights of 20,000 g/mol were purchased from Nanocs (Boston, Mass.). Peptides P1 (EYPPYP-PPPYPSGC, 1563 g/mol) were purchased through custom peptide synthesis from Genscript Corp (Piscataway, N.J., USA). All other chemicals were purchased from Sigma-Aldrich (Milwaukee, Wis.) unless otherwise noted. Amine-terminated PNIPAM was fractionated by dissolving it in acetone and stepwise precipitated by addition of hexanes. After collecting the high molecular weight fraction, it has a weight average molecular weight (Mw) of 10650 g/mol with a polydispersity index (PDI) of 1.2. A Michael-type addition of amine-terminated PNIPAM to 8-arm PEG-VS was first conducted at a ratio of amine:VS=1:8 in a Schlenk tube at pH 9.5 and 0.5 M triethylamine at 25° C. for 24 h. Then the rest unreacted arms of PEG-VS was further reacted with excessive P1 in the presence of tris(2-carboxyethyl)phosphine (TCEP). This PEG-PNIPAM-P1 copolymer solution was lyophilized, washed with chloroform to remove unreacted PEG, and then dialyzed. For comparison, PEG-P1 copolymer was synthesized by reacting 8-arm PEG-VS with excessive P1 and purified as described above. The chemical structures were confirmed by $^1$H Nuclear Magnetic Resonance (NMR) spectrometry, acquired on a Varian Inova 500 MHz NMR spectrometer using deuterium oxide as a solvent. To determine the Mw and PDI, gel permeation chromatography (GPC) was carried out at room temperature in tetrahydrofuran (THF) as the eluent at a flow rate of 1.0 mL/min using a Viscotek chromatograph and a Viscotek S3580 refractive index detector (Houston, Tex.) and standard monodisperse polystyrenes for calibration.

Figure 17:
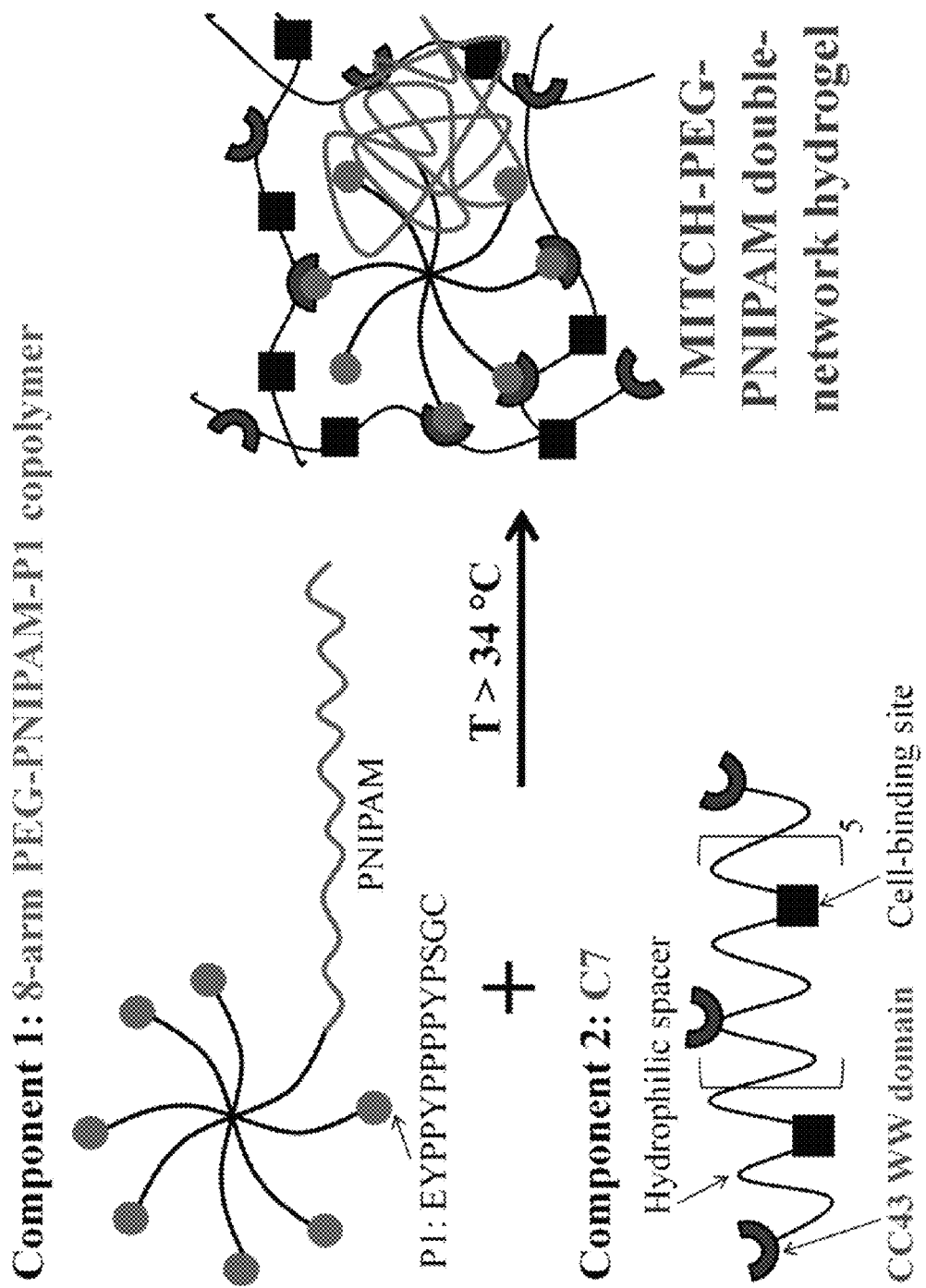
FIG. 17 shows according to an exemplary embodiment of the invention a schematic of MITCH-PEG-PNIPAM double-network hydrogel formation. Component 1 is a 8-arm PEG with theoretically 1 arm conjugated with PNIPAM chains and other 7 arms conjugated with proline-rich peptide (denoted as P) domains. Component 2 is a recombinant protein copolymer bearing CC43 WW (denoted as C) domains and RGD cell-binding domains connected by hydrophilic spacers. Simple mixing of the two components results in primary hydrogel network formation because of C to P specific binding at a 1:1 stoichiometry. At body temperature, which is higher than the lower critical solution temperature (LCST) of 34° C., a secondary network formation occurs due to a thermal phase transition of PNIPAM chains which form a reinforcing network.

Each WW domain in C7 was treated as one C unit and each pendant peptide group in the PEG-PNIPAM-P1 copolymer was treated as one P unit. MITCH-PEG-PNIPAM hydrogels were formed by mixing C7 and PEG-PNIPAM-P1 copolymer to achieve a final concentration of 10% w/v and a C:P ratio of 1:1 (FIG. 17). Similarly, MITCH-PEG hydrogels were formed by mixing C7 and PEG-P1 copolymer to achieve the same final concentration of 10% w/v and C:P ratio of 1:1. PEG-P1 and PEG-PNIPAM-P1 copolymer were also mixed at weight ratios of 30/70, 50/50, and 30/70 and then mixed with C7 to prepare mixtures of 30/70, 50/50, and 30/70 MITCH-PEG/MITCH-PEG-PNIPAM hydrogels, respectively.

Rheological Characterizations.

Dynamic oscillatory rheology experiments were performed on a stress-controlled rheometer (AR-G2, TA instrument, New Castle, Del.) using a 25 mm diameter cone-plate geometry. Samples were loaded immediately onto the rheometer and a humidity chamber was secured in place to prevent dehydration. Frequency sweeps at 25 and 37° C. were performed at 5% constant strain to obtain storage modulus G' and loss modulus G". Shear-thinning and self healing properties of the gel samples were characterized by measuring linear viscosities ($\eta$) under a time sweep mode, at alternating low and high shear rates of 0.1 $s^{-1}$ and 10 $s^{-1}$, respectively, for 30 s each and a total of 150 s.

Fluorescence Recovery after Photobleaching (FRAP) Diffusivity Measurement.

FRAP measurement was performed using dextran (MW=20, 40, and 70 kDa) conjugated to fluorescein isothiocyanate (FITC) (Invitrogen). Dextran was individually mixed with various hydrogel formulations (gel volume=30 µL, concentration=10% w/v, C:P ratio=1:1) at a final dextran concentration of 4 mg/mL, and the total fluorescence intensity was visualized at 37° C. using a Leica TCS SP5 confocal microscope at low light intensity. Photobleaching was done by exposing a 100×100 µm spot in the field of view to high intensity laser light. A series of images were taken every three seconds for five minutes to track the recovery of fluorescence. Control experiments were also performed using PBS, rat-tail Type I collagen (2 mg/mL, BD Biosciences), and growth-factor-reduced Matrigel (BD Biosciences) as diffusion media, prepared according to manufacturers' protocols. The resulting fluorescence recovery profiles were modeled by Fickian diffusion according to a previously reported method to calculate dextran diffusivities.[21].

Hydrogel Erosion Kinetics.

Hydrogels were formed in a circular silicone mold (diameter=4 mm, height=2 mm) within a 24-well plate (n≥3). The mixture was allowed to undergo sol-gel phase transition for 15 min at 37° C. in a humidified incubator, after which 1.5 mL of PBS was added to each well. Sampling volumes of 100 µL were obtained from the PBS supernatant and wells were replenished with 100 µL of fresh PBS over a period of 14 days. Gel erosion kinetics were studied by using absorbance spectroscopy at 280 nm (SpectraMax M2 Spectrophotometer, Molecular Devices) to measure the amount of protein released into the supernatant at each time point.

In Vitro Cell Injection and Quantification of Viability.

hASCs were harvested from human lipoaspirate from the flank and thigh regions by suction assisted liposuction. hASCs were transduced with lentivirus particles expressing the firefly luciferase gene (Qiagen). hASCs were cultured in Dulbecco's modified Eagle's medium (DMEM) supplemented with 10% fetal bovine serum (FBS) and 100 IU/ml penicillin/streptomycin at 37° C. and 5% atmospheric CO2. Cells were expanded and passaged by trypsinization for subsequent use in in vitro cell studies. All in vitro injection experiments were performed with 30 µl gel volume containing 5×$10^4$ cells. Cell suspension (5 µl) was first mixed with the 8-arm PEG-PNIPAM-P1 copolymer solution (20% w/v in PBS) and PBS before further mixing with C7 (10% w/v in PBS). The volumes of PEG-PNIPAM-P1 copolymer solution and C7 were adjusted to achieve a final C:P ratio of 1:1 at a total hydrogel concentration of 10% w/v. For cell injection studies, the final mixing step with C7 was performed in the barrel of a 28 G insulin syringe using a syringe pump (SP220I; World Precision Instruments) at a flow rate of 1 mL/min. The mixture was allowed to gel for 5 min before injecting into a circular silicone mold (diameter=4 mm, height=2 mm) within a 24-well plate (n≥4). Cell viability was determined using LIVE/DEAD viability/cytotoxicity kit (Invitrogen) at days 1, 4, 7, and 14 post-injection. Separate images from two channels were taken for viable cells with green fluorescence and nonviable cells with red fluorescence using a Leica TCS SP5 confocal microscope. Cell viability or the percentage of green cells was calculated from the number of green cells divided by the total number of cells. Cells were also fixed and stained with were fixed with 4% paraformaldehyde, permeabilized with 0.2% Triton X-100 solution in PBS, and stained with rhodamine phalloidin (1:300, Life Technologies) and 4',6-diamidino-2-phenylindole (DAPI, 1 µg $mL^{-1}$, Life Technologies). Images were collected using the Leica confocal microscope by creating z-stacks of greater than 200 µm depth into the hydrogel with 2.4 µm intervals between slices and then compressed into a maximum projection image.

In Vivo Transplantation and Bioluminescence Imaging.

All experiments followed protocols approved by the Stanford Administrative Panel on Laboratory Animal Care. NIH guidelines for the care and use of laboratory animals (NIH Publication #85-23 Rev. 1985) were observed. To track the material retention, C7 was labeled with Cyanine5.5 NHS ester, which is a near-infrared emitting dye (Lumiprobe) according to the manufacturer's protocol. For in vivo transplantation, athymic nude mice (25-30 g, male, Charles River Laboratories) were anesthetized with isoflurane, and hydrogel samples (30 µl, prepared as described above) were hand-injected subcutaneously via an insulin syringe with a 28-gauge needle. hASCs$^{Fluc+}$ resuspended at the same concentration in saline (30 µl) were also injected as controls. To minimize location specific bias, injection sites were randomized and rotated across the four injection sites per mouse. To monitor cell viability and distribution, bioluminescence imaging (BLI) was performed with an IVIS imaging system (Xenogen Corp.), and data was acquired with LivingImage™ software (Xenogen Corp.) on days 0, 3, 7, and 14. Before imaging, mice were anesthetized with 2% isoflurane/air. Reporter probe D-luciferin was administered via intraperitoneal injection at a dose of 350 mg/kg body weight. Bioluminescent images were acquired at 5-min intervals with an exposure time of 30 sec. For each image acquisition, a gray scale body surface image was collected, followed by an overlay of the pseudo-colored image of photon counts from active luciferase within the mouse. Image acquisition continued until all samples had reached peak intensity (5-30 min). Signal intensity for each sample was quantified as total flux (photons/sec) within a region of interest at peak intensity. Fluorescence images of Cyanine5.5 dye were also taken with an exposure time of 0.5 s at each time point and their intensities were quantified using the same software. All values were normalized to day 0.

Statistical Analysis.

All data are presented as mean±standard deviation. Statistical comparisons were performed by one-way analysis of variance (ANOVA) followed by Tukey post hoc test. Values were considered to be significantly different when the p value was <0.05.

Results

Figure 18:
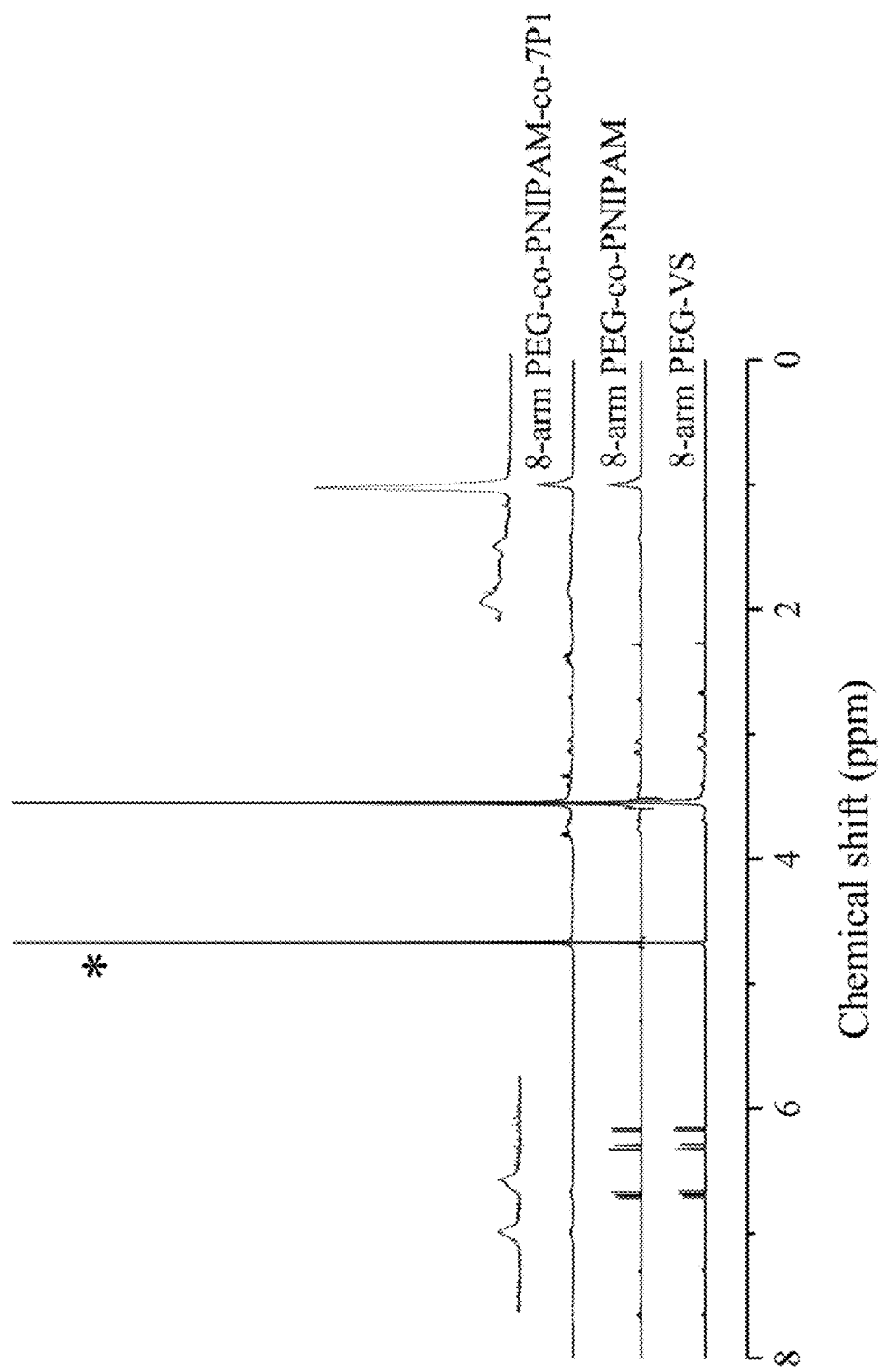
FIG. 18 shows according to an exemplary embodiment of the invention $^1$H NMR spectra ($D_2O$) of the 8-arm PEG-VS, 8-arm PEG-PNIPAM, and 8-arm PEG-PNIPAM-P1 copolymer. * denotes the solvent peak.
Figure 19:
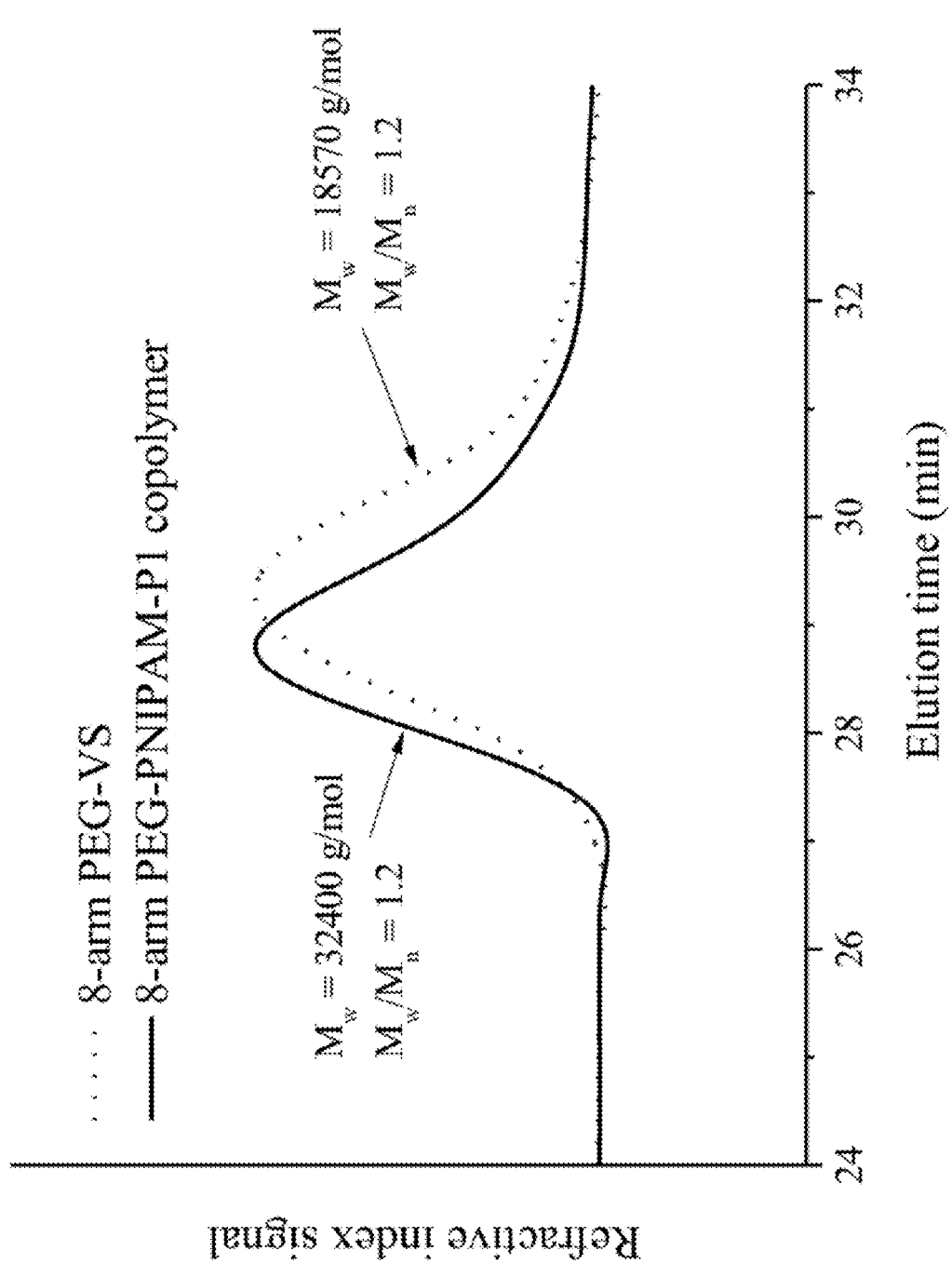
FIG. 19 shows according to an exemplary embodiment of the invention GPC traces for 8-arm PEG-VS and 8-arm PEG-PNIPAM-P1 copolymer using THF as a solvent.

Michael-type addition between amines or thiols and vinyl sulfones (VS) is a rapid and highly selective reaction that allows the conjugation of both PNIPAM and P1 peptide to PEG-VS to be performed under aqueous conditions. This two-step reaction was efficient with high degrees of conjugation (>70%) (FIG. 18). GPC curves indicated that the copolymers remained narrow molecular weight distributions and were purified with no traces of PNIPAM chain residues (FIG. 19).

Figure 20:
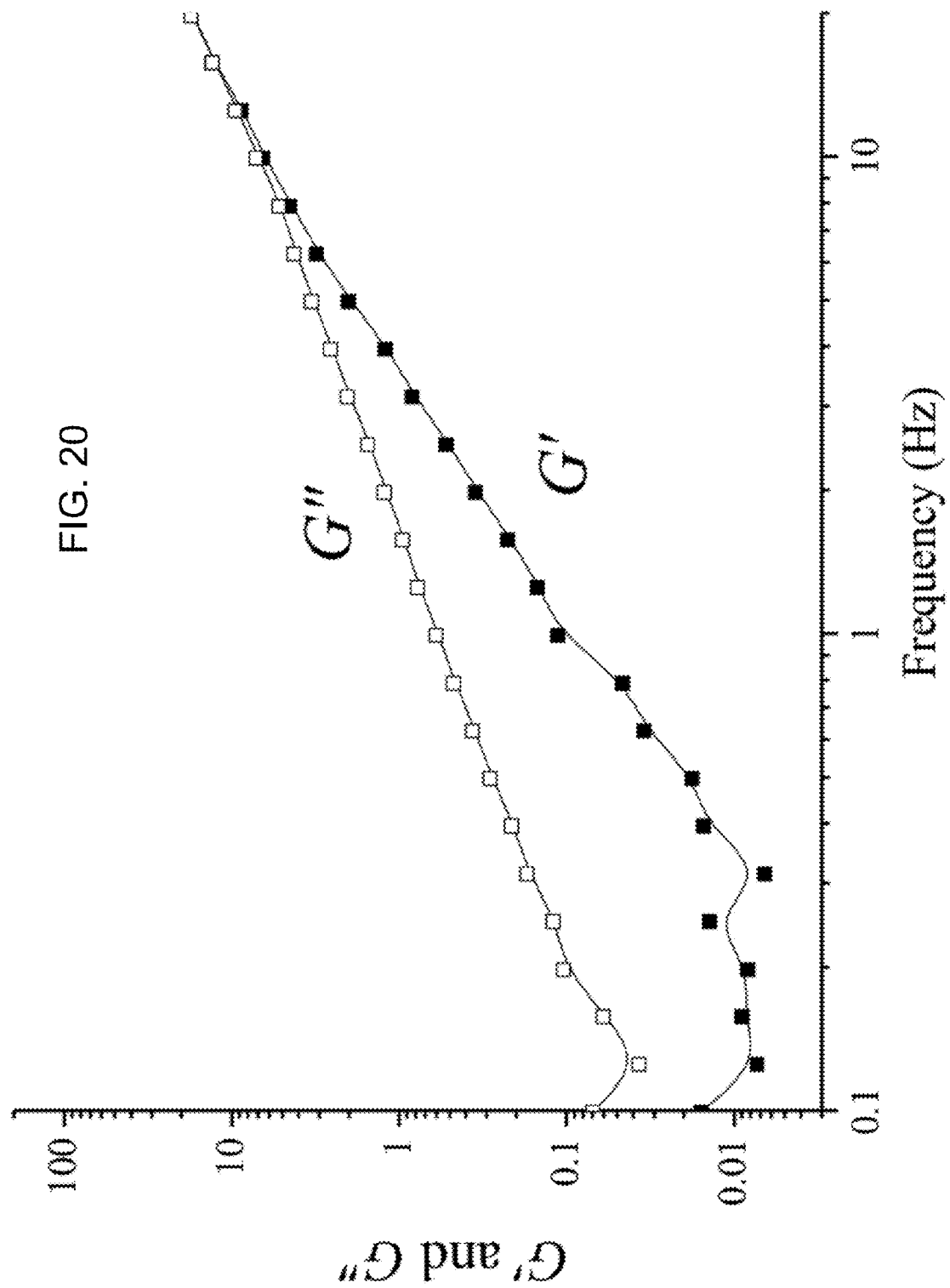
FIG. 20 shows according to an exemplary embodiment of the invention storage and loss moduli (G' and G") of 10 wt % 8-arm PEG-PNIPAM-P1 copolymer in water (without addition of C7 hetero-assembly protein partner) as a function of frequency at 25° C.

Rheological characterization demonstrates that MITCH-PEG-PNIPAM has a lower critical solution temperature (LCST) of ~34° C. To confirm the effect of PNIPAM on hydrogel mechanical properties, MITCH-PEG hydrogels were created as a control using C7 mixed with PEG-P1 copolymer with eight arms of PEG-VS all conjugated with P1 peptide. At body temperature, the shear modulus of the network increased an order of magnitude from ~10 Pa for MITCH-PEG hydrogel to ~100 Pa for MITCH-PEG-PNIPAM hydrogel as a result of the formation of a secondary PNIPAM physical network within the already existing MITCH hetero-assembled network (FIG. 21A). By mixing MITCH-PEG with MITCH-PEG-PNIPAM, we achieved a hydrogel with an intermediate modulus of ~70 Pa at a ratio of 30/70. Before mixing, PEG-PNIPAM-P1 copolymer exhibit viscoelastic behavior with shear moduli (G') smaller than loss moduli (G") with the presence of entanglements at higher frequencies, as indicated the crossover point (FIG. 20). After mixing of the two components, all hydrogels demonstrates curves characteristic of elastic networks formed by physical crosslinking, with G' consistently greater than G", confirming the gelation upon mixing the two components (FIG. 21B). A clear contrast is seen at body temperature, where the MITCH-PEG-PNIPAM hydrogel has a 10-fold increase in shear modulus, indicating that a secondary network of PNIPAM is formed above its LCST. To further confirm the formation of double networks, we measured hydrogel diffusivity which was highly pertinent to network mesh size or crosslinking density. By conducting fluorescence recovery after photobleaching (FRAP) using a fluorescently-labeled dextran, we found that MITCH-PEG-PNIPAM hydrogel had significantly slower diffusion than MITCH-PEG, indicating smaller mesh size for the double network hydrogel (FIG. 21C). All three hetero-assembled hydrogels diffused significantly slower compared to Matrigel and Type I collagen (2.5 mg/mL). Hydrogel erosion kinetics also showed that the MITHC-PEG-PNIPAM with the double network was eroded into the medium much slower than MITCH-PEG, consistent with hydrogel mesh size and diffusivity (FIG. 21D).

By measuring linear viscosity at alternative shear rates, we showed that MITCH-PEG-PNIPAM hydrogels exhibited shear-thinning behavior, or thixotropy, with much lower viscosity at higher shear rates at both room and body temperatures (FIG. 22A). The MITCH-PEG-PNIPAM hydrogels responded to the shifts of shear rates almost instantaneously and reversibly because of sharp yielding transition under high shear and rapid reformation of the physical network junctions upon shear removal. Interestingly, the stiffening effect from PNIPAM network exists at both shear rates at physiological temperature. Therefore, the MITCH-PEG-PNIPAM hydrogels with the ability to shear-thin and self-heal are ideal for injectable applications, where the hydrogels must be able to flow under hand pressure to facilitate easy injection and recover the gel state immediately post-injection. After confirming the formation of the physical hydrogels by molecular recognition and the stiffening effect from PNIPAM network, we tested the cytocompatibility and cell protective properties of the MITCH-PEG-PNIPAM hydrogels for potentially improving cell transplantation efficiency. We injected hASCs within this hydrogel through a 28 G syringe needle using a syringe pump at a flow rate of 1 mL/min and measured their acute viability using LIVE-DEAD assay. We found that right after injection, 93±4% of the hASCs were still alive within the hydrogel with minimal cell death (FIGS. 22B-C). This value is similar to non-injected controls. In a clear contrast, when the cells were injected in a saline solution, a considerable percentage of cells died immediately, resulting in a significantly lower viability of 69±5%. This result suggests the cell protective capability of the hydrogel during syringe injection.

We hypothesized that cell encapsulation within the hydrogel provided mechanical protection that prevents the damage caused by the extensional flow, which was found to be the major contributor to acute cell death. Moreover, our shear-thinning hydrogels are able to form a layer of shear-thinned fluid near the needle walls that allows the rest of the intact hydrogel to slip through the needle. This "plug flow" profile protects the cells in the broad central plug from the damaging shear forces.

Figure 23:
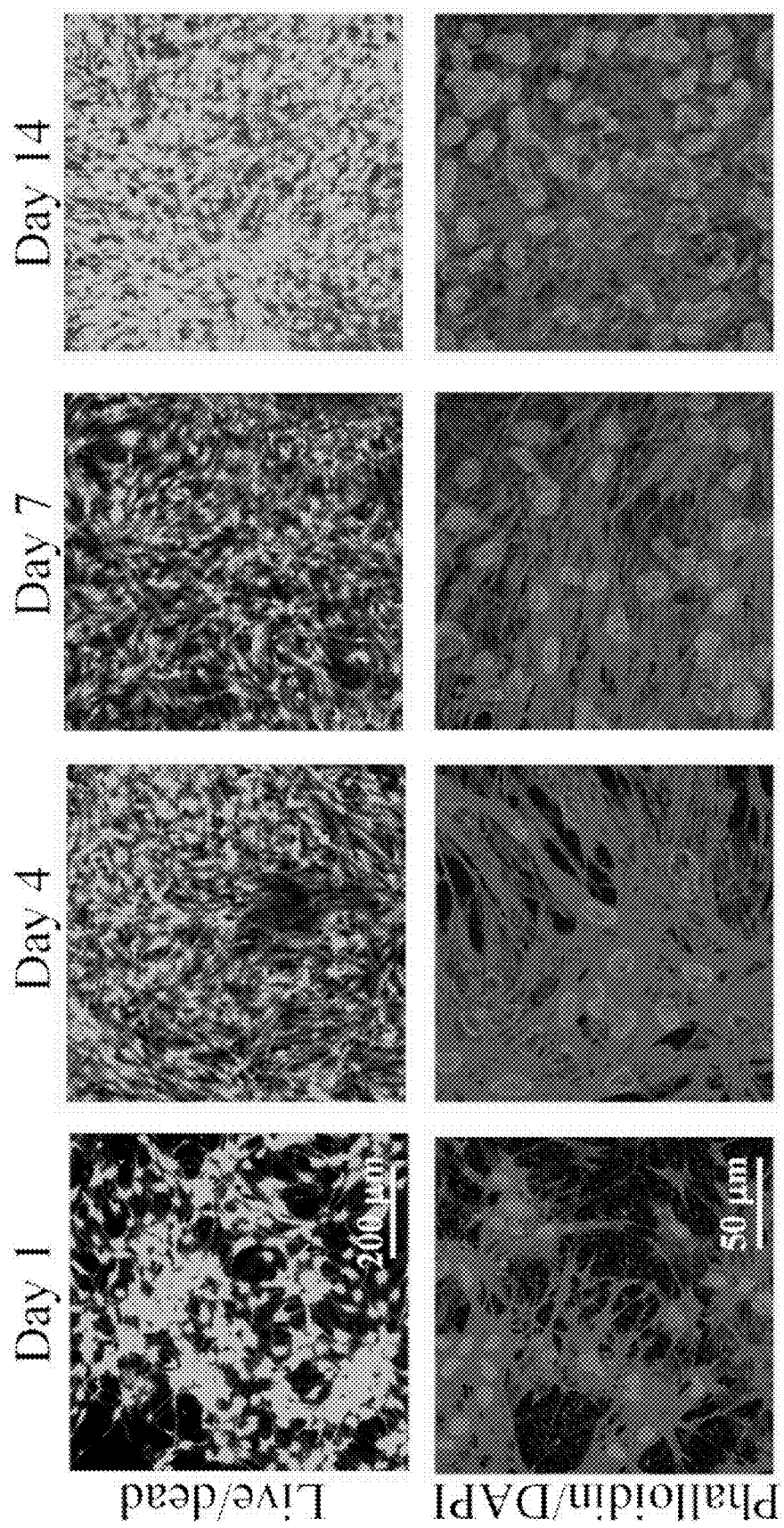
FIG. 23 shows according to an exemplary embodiment of the invention three-dimensional (3D) culture of hASCs within MITCH-PEG-PNIPAM hydrogels. Confocal fluorescence images of hASC morphology at days 1, 4, 7, and 14 post-injection stained with LIVE/DEAD assay (green/red, respectively, top row) and DAPI (blue) for cell nuclei and rhodamine phalloidin (red) for F-actin cytoskeleton (bottom row).
Figure 24A:
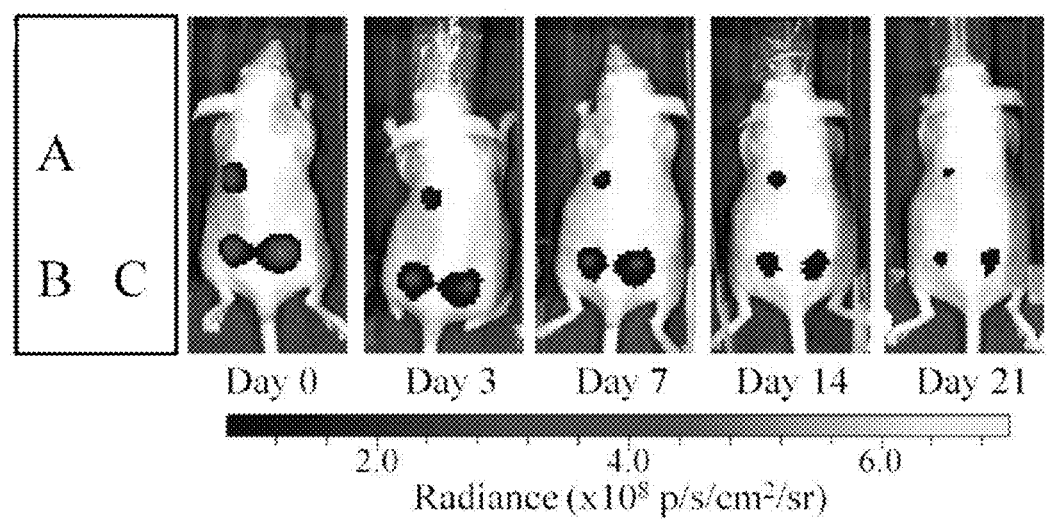
FIGS. 24A-B show according to an exemplary embodiment of the invention material retention after in vivo subcutaneous injection of hASCs within MITCH-PEG, MITCH-PEG-PNIPAM, and 30/70 MITCH-PEG/MITCH-PEG-PNIPAM hydrogels.
Figure 24B:
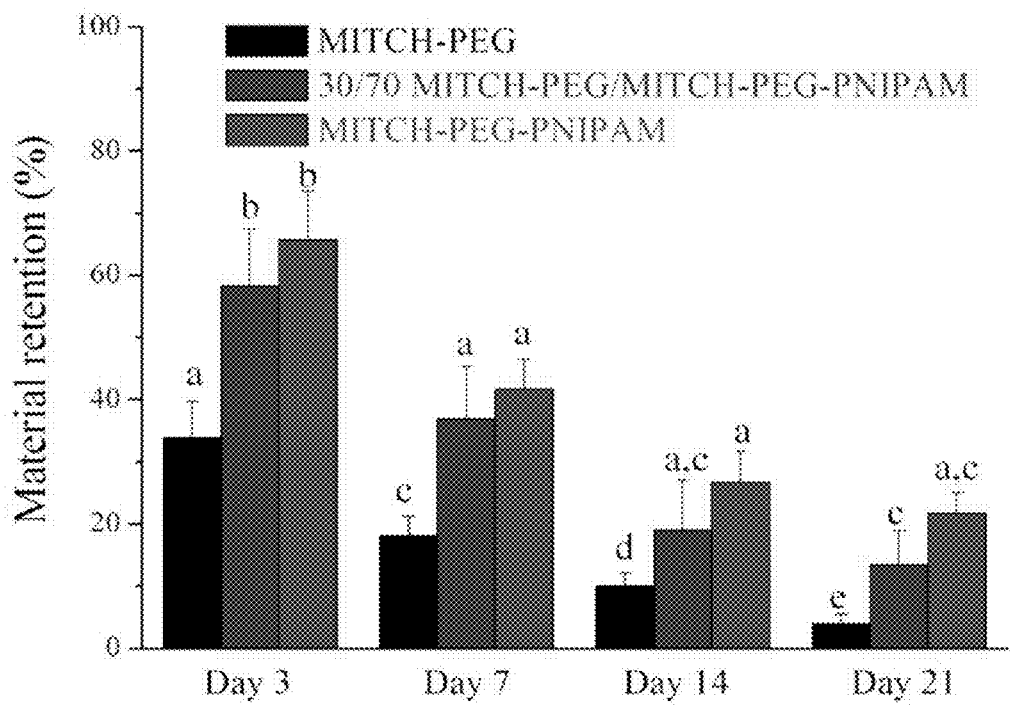
Figure 25A:
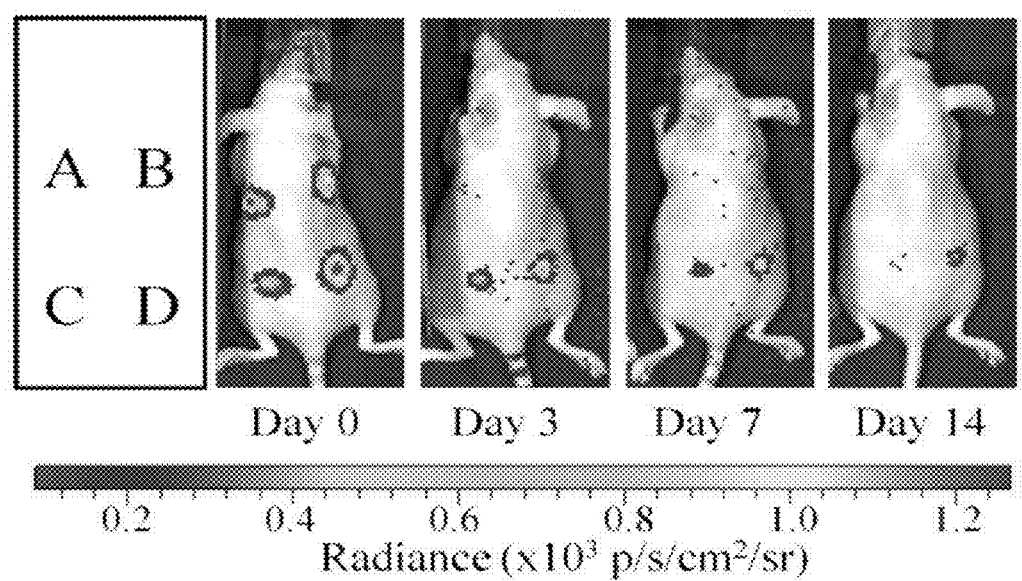
FIGS. 25A-B show according to an exemplary embodiment of the invention cell retention after in vivo subcutaneous injection of hASCs within MITCH-PEG, MITCH-PEG-PNIPAM, and 30/70 MITCH-PEG/MITCH-PEG-PNIPAM hydrogels.
Figure 25B:
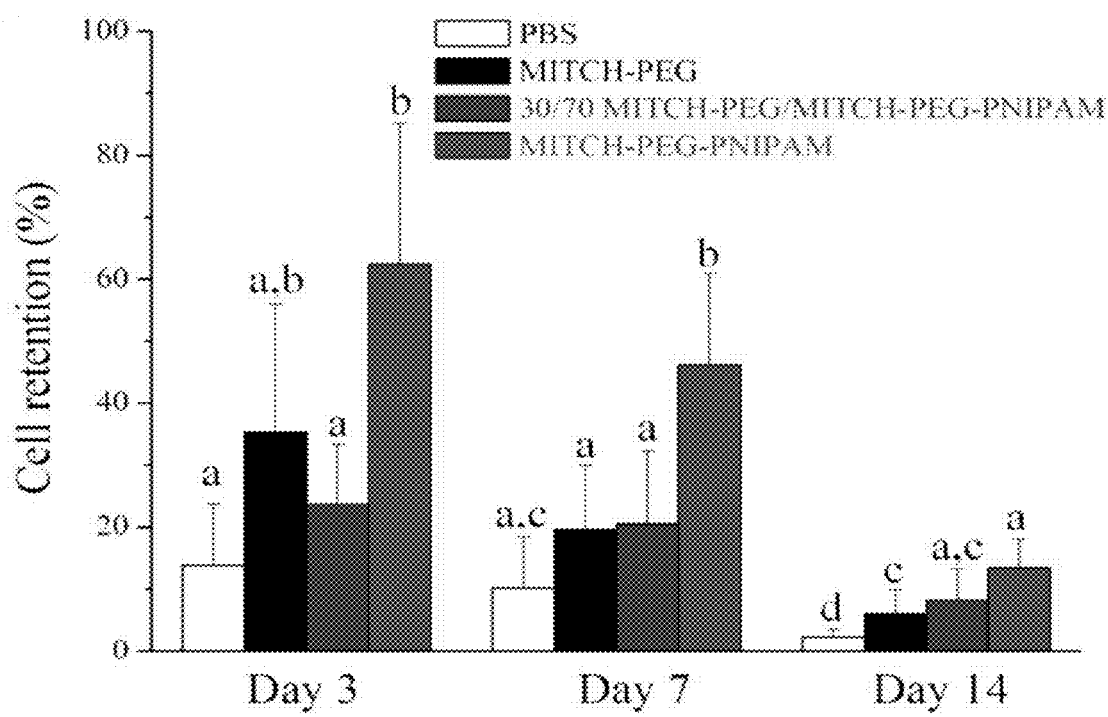

We further cultured hASCs within the 3D MITCH-PEG-PNIPAM hydrogels for 14 days post-injection, and quantified cell viability and morphologies. All hASCs remained proliferative and minimal cells were found dead within the hydrogel (FIG. 23). Cells exhibited spread-out morphologies with distinct actin filaments in 3D projection images. To study transplantation ability, both cells and hydrogels were tracked in vivo. hASCs$^{Fluc+}$ were injected subcutaneously into nude mice immediately following encapsulation in MITCH-PEG-PNIPAM hydrogels conjugated with a fluorescent dye. The cell encapsulating hydrogels were easily injectable under hand injection force and recovered as compact gel structures, which were visible as small nodules at the injection sites. Fluorescence intensities were quantified as indicators of material retention. MITCH-PEG hydrogels were mostly disappeared at the injection sites over 21 days. Significantly higher percentage of material retention was found for MITCH-PEG-PNIPAM than MITCH-PEG hydrogels, consistent with hydrogel diffusivity and erosion results (FIG. 24). The presence of viable hASCs was tracked and quantified for 14 days post-injection using BLI following intraperitoneal delivery of D-luciferin. hASCs injected within MITCH-PEG hydrogels or PBS were mostly undetectable at day 7 post-injection, possibly due to hydrogel erosion and cell migration and/or death. Encouragingly, the MITCH-PEG-PNIPAM hydrogels showed significantly better cell retentive properties with ~50% cells viable at day 7 post-injection and ~20% at day 14 post-injection, the improvement greater than 2-fold for MITCH-PEG hydrogels and 5-fold for saline controls (FIG. 25).

CONCLUSIONS

We have developed a new version of MITCH to address the problem of post-transplantation cell death and potentially eliminate a major bottleneck in cell replacement and regenerative therapy, as clinical outcome is contingent on the number of viable donor cells. This new MITCH-PEG-PNIPAM hydrogel retains the shear-thinning and self-healing properties from peptide-based molecular recognition components to encapsulate cells, while the conjugated PNIPAM chains form a second crosslinking step at physiological temperature to create a reinforcing network with 10-fold stiffer mechanical properties. Acute viability of hASCs immediately following encapsulation within MITCH-PEG-PNIPAM hydrogels and injection through 28 G syringe needle was significantly improved relative to injection within saline alone, suggesting the cell protective ability of the hydrogel from needle shearing during injection. Both material and cell retention after in vivo subcutaneous injection were significantly enhanced due to the presence of PNIPAM secondary network. This new hydrogel with in situ forming double networks offer better tunability on mechanical properties to potentially improve cell transplantation efficiency and long-term cell protection and cell functions for various tissue engineering applications.

What is claimed is:

1. A viscoelastic hydrogel, comprising: a protein hetero-assembled with a polymer, wherein the protein cannot self-assemble with itself, wherein the polymer cannot self-assemble with itself, wherein the protein includes a first association sequence (1stA) and a first spacer (1stSp), wherein the polymer includes a second association sequence (2ndA) and a second spacer (2ndSp), wherein the first association sequence and the second association sequence are physically cross-linked to interact with each other with a 1:1 known and specific stoichiometry to form a three dimensional scaffold, wherein the protein is represented by $\{1stA(1stSp)\}_x 1stA$, where x is $\geq 2$, and the polymer is represented by $\{2ndA(2ndSp)\}_y 2ndA$, where $y \geq 2$.

2. The viscoelastic hydrogel as set forth in claim 1, wherein the protein is represented by $\{1stA(1stSp)_m\}_x 1stA$, where m is 1 to 50, and x is 2 to 15; and the polymer is represented by $\{2ndA(2ndSp)\}_y 2ndA$, where y is 2 to 64.

3. The viscoelastic hydrogel as set forth in claim 1, wherein the first association sequence is a WW protein sequence.

4. The viscoelastic hydrogel as set forth in claim 1, wherein the second association sequence is 1, 2, 3 or 4 repeats of a polyproline-rich peptide sequence in series.

5. The viscoelastic hydrogel as set forth in claim 1, wherein the second spacer is a branched polyethylene glycol.

6. The viscoelastic hydrogel as set forth in claim 1, wherein the second spacer is a linear polyethylene glycol.

7. The viscoelastic hydrogel as set forth in claim 4, wherein the second spacer has a molecular range in the order of 10-200 kDa.

8. The viscoelastic hydrogel as set forth in claim 1, wherein the second spacer is a polypeptide or a polysaccharide.

9. The viscoelastic hydrogel as set forth in claim 1, wherein the second spacer is a biopolymer alginate.

10. The viscoelastic hydrogel as set forth in claim 1, wherein the polymer comprises a copolymer block of a stimuli-responsive polymer.

11. The viscoelastic hydrogel as set forth in claim 1, wherein the polymer comprises a copolymer block, wherein the copolymer block is a poly(n-isopropylacrylamide) and the resulting hydrogel contains 0-10 wt/vol % of poly(n-isopropylacrylamide).

* * * * *

SEQUENCE LISTING

<160> NUMBER OF SEQ ID NOS: 10

<210> SEQ ID NO 1
<211> LENGTH: 34
<212> TYPE: PRT
<213> ORGANISM: Artificial Sequence
<220> FEATURE:
<223> OTHER INFORMATION: Computationally derived
<220> FEATURE:
<221> NAME/KEY: MISC_FEATURE
<222> LOCATION: (1)..(34)
<223> OTHER INFORMATION: See Figure 3.
<300> PUBLICATION INFORMATION:
<301> AUTHORS: Russ, W.P., Lowery, D.M., Mishra, P., Yaffe, M.B., & Ranganathan R
<302> TITLE: Natural-like function in artificial WW domains
<303> JOURNAL: Nature
<304> VOLUME: 437
<306> PAGES: 579-83
<307> DATE: 2005

<400> SEQUENCE: 1

Arg Leu Pro Ala Gly Trp Glu Gln Arg Met Asp Val Lys Gly Arg Pro
1               5                   10                  15

Tyr Phe Val Asp His Val Thr Lys Ser Thr Thr Trp Glu Asp Pro Arg
            20                  25                  30

Pro Glu

<210> SEQ ID NO 2
<211> LENGTH: 34
<212> TYPE: PRT
<213> ORGANISM: Unknown
<220> FEATURE:
<223> OTHER INFORMATION: Natural WW domain also called Nedd4.3 Kanelis,
      V., Rotin D. & Forman-Kay, JD (2001) Solution structure of a Nedd4
      WW domain-ENaC peptide complex, Nat Struct Biol 8: 407-12.
<220> FEATURE:
<221> NAME/KEY: MISC_FEATURE
<222> LOCATION: (1)..(34)
<223> OTHER INFORMATION: See Figure 3.
<300> PUBLICATION INFORMATION:
<301> AUTHORS: Kanelis, V, Rothin, D., & Forman-Kay, J.D.
<302> TITLE: Solution structure of a Nedd4 WW domain ENaC peptide
      complex
<303> JOURNAL: Nat. Struct. Biol.
<304> VOLUME: 8
<306> PAGES: 407-12
<307> DATE: 2001

<400> SEQUENCE: 2

Pro Leu Pro Pro Gly Trp Glu Glu Arg Thr His Thr Asp Gly Arg Val
1               5                   10                  15

Phe Phe Ile Asn His Asn Ile Lys Lys Thr Gln Trp Glu Asp Pro Arg
            20                  25                  30

Met Gln

<210> SEQ ID NO 3
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: See Figure 3.
<300> PUBLICATION INFORMATION:
<301> AUTHORS: Russ, W.P., Lowery, D.M., Mishra, P., Yaffe M.B., & Ranganathan R.
<302> TITLE: Natural-like function in artificial WW domains
<303> JOURNAL: Nature
<304> VOLUME: 437

```
<306> PAGES: 579-583
<307> DATE: 2005
<313> RELEVANT RESIDUES IN SEQ ID NO: (1)..(13)

<400> SEQUENCE: 3

Glu Tyr Pro Pro Tyr Pro Pro Pro Pro Tyr Pro Ser Gly
1               5                   10

<210> SEQ ID NO 4
<211> LENGTH: 45
<212> TYPE: PRT
<213> ORGANISM: Artificial Sequence
<220> FEATURE:
<223> OTHER INFORMATION: Artificial sequence.
<220> FEATURE:
<221> NAME/KEY: MISC_FEATURE
<222> LOCATION: (1)..(45)
<223> OTHER INFORMATION: Combines a repeated set of hydrophilic spacers
      AGAGAGPEG with a fibronectin-derived RGDS cell-adhesion sequence.
      See Fig. 3.
<300> PUBLICATION INFORMATION:
<301> AUTHORS: Shen, W., Kornfield, JA, Tirrell, DA
<302> TITLE: Structure and mechanical properties of artificial protein
      hydrogels assembled through aggregation of leucine zipper peptide
      domains
<303> JOURNAL: Soft Matter
<304> VOLUME: 3
<306> PAGES: 99-107
<307> DATE: 2007
<313> RELEVANT RESIDUES IN SEQ ID NO: (1)..(9)
<300> PUBLICATION INFORMATION:
<301> AUTHORS: Petka, W.A., Harden, J.L., McGrath, K.P., Wirtz, D.,
      Tirrell, DA.
<302> TITLE: Reversible Hydrogels from Self-Assembling Artificial
      Proteins
<303> JOURNAL: Science
<304> VOLUME: 281
<306> PAGES: 389-392
<307> DATE: 1998-07-17
<313> RELEVANT RESIDUES IN SEQ ID NO: (1)..(9)
<300> PUBLICATION INFORMATION:
<301> AUTHORS: Guler, M.O., Hsu, L., Soukasene, S., Harrington, D.A.,
      Hulvat, J.F., Stupp, S.I.
<302> TITLE: Presentation of RGDS Epitopes on Self-Assembled Nanofibers
      of Branched Peptide Amphiphiles
<303> JOURNAL: Biomacromoleculses
<304> VOLUME: 7
<305> ISSUE: 6
<306> PAGES: 1855-1863
<307> DATE: 2006-05-19
<313> RELEVANT RESIDUES IN SEQ ID NO: (18)..(21)

<400> SEQUENCE: 4

Ala Gly Ala Gly Ala Gly Pro Glu Gly Ala Gly Ala Gly Ala Gly Pro
1               5                   10                  15

Glu Gly Arg Gly Asp Ser Ala Gly Pro Glu Gly Ala Gly Ala Gly Ala
            20                  25                  30

Gly Pro Glu Gly Ala Gly Ala Gly Ala Gly Pro Glu Gly
            35                  40                  45

<210> SEQ ID NO 5
<211> LENGTH: 45
<212> TYPE: PRT
<213> ORGANISM: Artificial Sequence
<220> FEATURE:
<223> OTHER INFORMATION: Artifical sequence
<220> FEATURE:
<221> NAME/KEY: MISC_FEATURE
<222> LOCATION: (1)..(45)
<223> OTHER INFORMATION: Combines repeated set of hydrophilic spacers
      AGAGAGPEG with a laminin-1 derived YIGSR binding protein sequence.
      See Figure 3
```

```
<400> SEQUENCE: 5

Ala Gly Ala Gly Ala Gly Pro Glu Gly Ala Gly Ala Gly Ala Gly Pro
1               5                   10                  15

Glu Gly Tyr Ile Gly Ser Arg Gly Pro Glu Gly Ala Gly Ala Gly Ala
            20                  25                  30

Gly Pro Glu Gly Ala Gly Ala Gly Ala Gly Pro Glu Gly
        35                  40                  45

<210> SEQ ID NO 6
<211> LENGTH: 18
<212> TYPE: PRT
<213> ORGANISM: Artificial Sequence
<220> FEATURE:
<223> OTHER INFORMATION: Artifical sequence
<220> FEATURE:
<221> NAME/KEY: MISC_FEATURE
<222> LOCATION: (1)..(19)
<223> OTHER INFORMATION: Previously described hydrophilic spacer
      AGAGAGPEG repeated twice. See Figure 3.

<400> SEQUENCE: 6

Ala Gly Ala Gly Ala Gly Pro Glu Gly Ala Gly Ala Gly Ala Gly Pro
1               5                   10                  15

Glu Gly

<210> SEQ ID NO 7
<211> LENGTH: 33
<212> TYPE: PRT
<213> ORGANISM: Escherichia coli
<220> FEATURE:
<221> NAME/KEY: MISC_FEATURE
<222> LOCATION: (1)..(33)
<223> OTHER INFORMATION: 6xHis tag produced as part of the recombinant
      protein production process in Escherichia coli .  See Fig 3.

<400> SEQUENCE: 7

Met Gly Ser Ser His His His His His His Ser Ser Gly Leu Val Pro
1               5                   10                  15

Arg Gly Ser Ser Ser Gly His Ile Asp Asp Asp Asp Lys Val Asp Gly
            20                  25                  30

Thr

<210> SEQ ID NO 8
<211> LENGTH: 253
<212> TYPE: PRT
<213> ORGANISM: Artificial Sequence
<220> FEATURE:
<223> OTHER INFORMATION: Artifical sequence for a hydrogel
<220> FEATURE:
<221> NAME/KEY: MISC_FEATURE
<222> LOCATION: (1)..(253)
<223> OTHER INFORMATION: Engineered sequence: N-terminal 6xHis Tag, WW
      Domain CC43, GTLDEL, Hydrophilic Spacer 1- RGDS site, ELLDGT, 1x
      to 5x repeated series of: [WW Domain CC43, GTLDEL, Hydrophobic
      Spacer 1-RGDS site, ELLDGT), WW Domain CC43, GTLE: see Fig. 3
<220> FEATURE:
<221> NAME/KEY: REPEAT
<222> LOCATION: (125)..(215)
<223> OTHER INFORMATION: Repeated between 1-5 times.  That is 1x, 2x,
      3x, 4x, and 5x are taught

<400> SEQUENCE: 8

Met Gly Ser Ser His His His His His His Ser Ser Gly Leu Val Pro
1               5                   10                  15

Arg Gly Ser Ser Ser Gly His Ile Asp Asp Asp Asp Lys Val Asp Gly
            20                  25                  30
```

```
Thr Arg Leu Pro Ala Gly Trp Glu Gln Arg Met Asp Val Lys Gly Arg
            35                  40                  45

Pro Tyr Phe Val Asp His Val Thr Lys Ser Thr Thr Trp Glu Asp Pro
 50                  55                  60

Arg Pro Glu Gly Thr Leu Asp Glu Leu Ala Gly Ala Gly Ala Gly Pro
 65                  70                  75                  80

Glu Gly Ala Gly Ala Gly Ala Gly Pro Glu Gly Arg Gly Asp Ser Ala
                85                  90                  95

Gly Pro Glu Gly Ala Gly Ala Gly Ala Gly Pro Glu Gly Ala Gly Ala
            100                 105                 110

Gly Ala Gly Pro Glu Gly Glu Leu Leu Asp Gly Thr Arg Leu Pro Ala
            115                 120                 125

Gly Trp Glu Gln Arg Met Asp Val Lys Gly Arg Pro Tyr Phe Val Asp
            130                 135                 140

His Val Thr Lys Ser Thr Thr Trp Glu Asp Pro Arg Pro Glu Gly Thr
145                 150                 155                 160

Leu Asp Glu Leu Ala Gly Ala Gly Ala Gly Pro Glu Gly Ala Gly Ala
                165                 170                 175

Gly Ala Gly Pro Glu Gly Arg Gly Asp Ser Ala Gly Pro Glu Gly Ala
            180                 185                 190

Gly Ala Gly Ala Gly Pro Glu Gly Ala Gly Ala Gly Ala Gly Pro Glu
            195                 200                 205

Gly Glu Leu Leu Asp Gly Thr Arg Leu Pro Ala Gly Trp Glu Gln Arg
            210                 215                 220

Met Asp Val Lys Gly Arg Pro Tyr Phe Val Asp His Val Thr Lys Ser
225                 230                 235                 240

Thr Thr Trp Glu Asp Pro Arg Pro Glu Gly Thr Leu Glu
                245                 250

<210> SEQ ID NO 9
<211> LENGTH: 253
<212> TYPE: PRT
<213> ORGANISM: Artificial Sequence
<220> FEATURE:
<223> OTHER INFORMATION: Artificial hydrogel component
<220> FEATURE:
<221> NAME/KEY: MISC_FEATURE
<222> LOCATION: (1)..(253)
<223> OTHER INFORMATION: Engineered sequence: N-terminal 6xHis tag ,
      WW Domain N39, GTLDEL, Hydrophilic spacer 1-RDGS site, Hyrdophilic
      spacer 2, ELLDGT, 1x to 5x repeated (WW Domain N39, GTLDEL,
      Hyrdophilic spacer 1-RDGS site, ELLDGT), WW Domain N39, GTLE:
      see Fig. 3
<220> FEATURE:
<221> NAME/KEY: REPEAT
<222> LOCATION: (125)..(214)
<223> OTHER INFORMATION: Repeated from 1 to 5 times.  That is 1x, 2x,
      3x, 4x, and 5x are taught

<400> SEQUENCE: 9

Met Gly Ser Ser His His His His His Ser Ser Gly Leu Val Pro
 1               5                  10                  15

Arg Gly Ser Ser Ser Gly His Ile Asp Asp Asp Asp Lys Val Asp Gly
                20                  25                  30

Thr Pro Leu Pro Pro Gly Trp Glu Arg Thr His Thr Asp Gly Arg
            35                  40                  45

Val Phe Phe Ile Asn His Asn Ile Lys Lys Thr Gln Trp Glu Asp Pro
 50                  55                  60

Arg Met Gln Gly Thr Leu Asp Glu Leu Ala Gly Ala Gly Ala Gly Pro
```

-continued

```
                65                  70                  75                  80
        Glu Gly Ala Gly Ala Gly Ala Gly Pro Glu Gly Arg Gly Asp Ser Ala
                        85                  90                  95

Gly Pro Glu Gly Ala Gly Ala Gly Ala Gly Pro Glu Gly Ala Gly Ala
                    100                 105                 110

Gly Ala Gly Pro Glu Gly Glu Leu Leu Asp Gly Thr Pro Leu Pro Pro
                    115                 120                 125

Gly Trp Glu Glu Arg Thr His Thr Asp Gly Arg Val Phe Phe Ile Asn
                130                 135                 140

His Asn Ile Lys Lys Thr Gln Glu Asp Pro Arg Met Gln Gly Thr Leu
        145                 150                 155                 160

Asp Glu Leu Ala Gly Ala Gly Ala Gly Pro Glu Gly Ala Gly Ala Gly
                        165                 170                 175

Ala Gly Pro Glu Gly Arg Gly Asp Ser Ala Gly Pro Glu Gly Ala Gly
                    180                 185                 190

Ala Gly Ala Gly Pro Glu Gly Ala Gly Ala Gly Ala Gly Pro Glu Gly
                    195                 200                 205

Glu Leu Leu Asp Gly Thr Pro Leu Pro Pro Gly Trp Glu Glu Arg Thr
                    210                 215                 220

His Thr Asp Gly Arg Val Phe Phe Ile Asn His Asn Ile Lys Lys Thr
        225                 230                 235                 240

Gln Trp Glu Asp Pro Pro Arg Met Gln Gly Thr Leu Glu
                        245                 250

<210> SEQ ID NO 10
<211> LENGTH: 136
<212> TYPE: PRT
<213> ORGANISM: Artificial Sequence
<220> FEATURE:
<223> OTHER INFORMATION: Artificial hydrogel component
<220> FEATURE:
<221> NAME/KEY: MISC_FEATURE
<222> LOCATION: (1)..(136)
<223> OTHER INFORMATION: Engineered sequence: N-terminal 6xHis Tag,
      Polyproline-rich Peptide PPxY, GTLDEL, Hydrophilic spacer 2,
      ELLDGT, 1x to 7x repeated (Polyproline-rich Peptide PPxY, GTLDEL,
      Hydrophilic spacer 2, ELLDGT), Polyproline-rich Peptide PPxY,
      GTLE: see Fig.
<220> FEATURE:
<221> NAME/KEY: REPEAT
<222> LOCATION: (77)..(119)
<223> OTHER INFORMATION: Repeated from 1 to 7 times.  That is, 1x, 2x,
      3x, 4x, 5x, 6x, and 7x are taught

<400> SEQUENCE: 10

Met Gly Ser Ser His His His His His His Ser Ser Gly Leu Val Pro
        1               5                   10                  15

Arg Gly Ser Ser Ser Gly His Ile Asp Asp Asp Asp Lys Val Asp Gly
                    20                  25                  30

Thr Glu Tyr Pro Pro Tyr Pro Pro Pro Tyr Pro Ser Gly Gly Thr
                        35                  40                  45

Leu Asp Glu Leu Ala Gly Ala Gly Ala Gly Pro Glu Gly Ala Gly Ala
                    50                  55                  60

Gly Ala Gly Pro Glu Gly Glu Leu Leu Asp Gly Thr Glu Tyr Pro Pro
        65                  70                  75                  80

Tyr Pro Pro Pro Tyr Pro Ser Gly Gly Thr Leu Asp Glu Leu Ala
                        85                  90                  95
```

-continued

```
Gly Ala Gly Ala Gly Pro Glu Gly Ala Gly Ala Gly Ala Gly Pro Glu
            100                 105                 110

Gly Glu Leu Leu Asp Gly Thr Glu Tyr Pro Pro Tyr Pro Pro Pro Pro
        115                 120                 125

Tyr Pro Ser Gly Gly Thr Leu Glu
    130                 135
```